US008168611B1

(12) United States Patent
Perrin et al.

(10) Patent No.: US 8,168,611 B1
(45) Date of Patent: *May 1, 2012

(54) COMPOSITIONS, KITS AND METHODS FOR NUTRITION SUPPLEMENTATION

(75) Inventors: Philippe Perrin, Paris (FR); Guillaume Herry, Hoboken, NJ (US); Cecile Boyer-Joubert, Fontenay Aux Roses (FR)

(73) Assignee: Chemo S.A. France, Sevres (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/248,428

(22) Filed: Sep. 29, 2011

(51) Int. Cl.
*A01N 43/04* (2006.01)
(52) U.S. Cl. .......... 514/52; 514/168; 514/251; 514/276; 514/458; 514/474; 514/725
(58) Field of Classification Search .................... 514/52, 514/168, 251, 276, 458, 474, 725
See application file for complete search history.

(56) References Cited

U.S. PATENT DOCUMENTS

| 2,699,429 A | 1/1955 | Lowenstein |
|---|---|---|
| 3,160,564 A | 12/1964 | Hanus |
| 3,608,083 A | 9/1971 | Bunnell |
| 3,846,550 A | 11/1974 | Akrongold |
| 4,009,265 A | 2/1977 | Howard |
| 4,124,710 A | 11/1978 | Descamps |
| 4,224,319 A | 9/1980 | Marcadet |
| 4,251,550 A | 2/1981 | Proctor |
| 4,374,082 A | 2/1983 | Hochschild |
| 4,407,821 A | 10/1983 | Mendy |
| 4,431,634 A | 2/1984 | Ellenbogen |
| 4,526,793 A | 7/1985 | Ingenbleek et al. |
| 4,544,559 A | 10/1985 | Gil |
| 4,547,488 A | 10/1985 | Merkel |
| 4,614,663 A | 9/1986 | Rule |
| 4,619,829 A | 10/1986 | Motschan |
| 4,710,387 A | 12/1987 | Uiterwaal et al. |
| 4,740,373 A | 4/1988 | Kesselman et al. |
| 4,803,087 A | 2/1989 | Karinen |
| 4,804,535 A | 2/1989 | Kesselman et al. |
| 4,810,726 A | 3/1989 | Bistrian et al. |
| 4,814,102 A | 3/1989 | Baur et al. |
| 4,851,431 A | 7/1989 | Yehuda |
| 4,863,898 A | 9/1989 | Ashmead et al. |
| 4,900,566 A | 2/1990 | Howard |
| 4,940,658 A | 7/1990 | Allen et al. |
| 4,945,083 A | 7/1990 | Jansen |
| 4,976,960 A | 12/1990 | Grossman et al. |
| 5,000,975 A | 3/1991 | Tomarelli |
| 5,013,569 A | 5/1991 | Rubin |
| 5,059,622 A | 10/1991 | Sears |
| 5,108,767 A | 4/1992 | Mulchandani et al. |
| 5,116,819 A | 5/1992 | Trimbo et al. |
| 5,169,891 A | 12/1992 | Brown |
| 5,210,133 A | 5/1993 | O'Lenick |
| 5,215,750 A | 6/1993 | Keane |
| 5,215,754 A | 6/1993 | Valorose |
| 5,221,544 A | 6/1993 | Sweeney et al. |
| 5,221,668 A | 6/1993 | Henningfield et al. |
| 5,223,285 A | 6/1993 | DeMichele |
| 5,278,329 A | 1/1994 | Anderson |
| 5,326,569 A | 7/1994 | Acosta et al. |
| 5,340,315 A | 8/1994 | Kaye |
| 5,340,594 A | 8/1994 | Barclay |
| 5,374,560 A | 12/1994 | Allen et al. |
| 5,407,957 A | 4/1995 | Kyle et al. |
| 5,422,127 A | 6/1995 | Dube et al. |
| 5,438,017 A | 8/1995 | Allen |
| 5,444,054 A | 8/1995 | Garleb |
| 5,457,055 A | 10/1995 | Allen et al. |
| 5,492,938 A | 2/1996 | Kyle et al. |
| 5,494,678 A | 2/1996 | Paradissis et al. |
| 5,514,382 A | 5/1996 | Sultenfuss |
| 5,545,411 A | 8/1996 | Chancellor |
| 5,550,146 A | 8/1996 | Acosta et al. |
| 5,556,644 A | 9/1996 | Chandra |
| 5,563,126 A | 10/1996 | Allen et al. |
| 5,569,458 A | 10/1996 | Greenberg |
| 5,571,441 A | 11/1996 | Andon |
| 5,574,065 A | 11/1996 | Trimbo |
| 5,585,134 A | 12/1996 | Cummings et al. |
| 5,589,468 A | 12/1996 | Lin et al. |
| 5,591,446 A | 1/1997 | Melnik |

(Continued)

FOREIGN PATENT DOCUMENTS

CN 101095433 A 1/2008
(Continued)

OTHER PUBLICATIONS

Feltrin et al, Am J Clin Nutr, 2008, 87, 1181-1187.*
Puritan (2011).*
PairOB (2011).*
VitaMed(2011).*
Lauricidin (2011).*
Kagan et al., 44(8) Biochem. Pharmacol. 1637-1649 (1992).
Kang-Yoon et al., 56 Am. J. Clin. Nutr. 548-58 (1992).
Kharb, 93(1) Euro. J. Obstet. Gynecol. Reprod. Biol. 37-39 (2000).
Kim, 57(10) Nutr. Reviews 314-21 (1999).
King, 71 (SUDD.) Am. J. Clin. Nutr. 1334S-43S (2000).
Kishi et al., 48 Diabetes 2045-2051 (1999).
Kumik et al., Annals of pharmacotherapy, vol. 37(11 ):1603-06 (2003).

(Continued)

*Primary Examiner* — Jeffrey S. Lundgren
*Assistant Examiner* — Ibrahim D Bori
(74) *Attorney, Agent, or Firm* — Don J. Pelto, Esquire; Sheppard, Mullin, Richter & Hampton LLP

(57) ABSTRACT

The present invention relates to compositions, kits and methods for the administration of various vitamin, mineral and nutrient compositions, and in a specific embodiment, the compositions, kits and methods may utilize or include twelve carbon chain fatty acids and/or twelve carbon chain acylglycerols, vitamin D, iodine, vitamin B1, vitamin B6, vitamin B12, vitamin B2, vitamin B9, vitamin B3, vitamin E, vitamin A, vitamin C, iron, zinc, copper, magnesium, omega 3 fatty acids and one or more pharmaceutically acceptable carriers.

5 Claims, No Drawings

U.S. PATENT DOCUMENTS

| | | |
|---|---|---|
| 5,601,860 A | 2/1997 | Lien |
| 5,612,060 A | 3/1997 | Alexander |
| 5,626,884 A | 5/1997 | Lockett |
| 5,631,290 A | 5/1997 | Almond |
| 5,635,199 A | 6/1997 | Trimbo et al. |
| 5,641,814 A | 6/1997 | Martin |
| 5,648,380 A | 7/1997 | Martin |
| 5,658,956 A | 8/1997 | Martin |
| 5,658,957 A | 8/1997 | Martin |
| 5,660,842 A | 8/1997 | Petschow |
| 5,663,208 A | 9/1997 | Martin |
| 5,686,429 A | 11/1997 | Lin et al. |
| 5,707,670 A | 1/1998 | Mehansho et al. |
| 5,709,888 A | 1/1998 | Gil et al. |
| 5,714,472 A | 2/1998 | Gray et al. |
| 5,723,446 A | 3/1998 | Gray et al. |
| 5,770,215 A | 6/1998 | Moshyedi |
| 5,780,451 A | 7/1998 | DeMichele et al. |
| 5,795,873 A | 8/1998 | Allen |
| 5,866,106 A | 2/1999 | Papay |
| 5,869,084 A | 2/1999 | Paradissis et al. |
| 5,874,392 A | 2/1999 | Halvorson et al. |
| 5,898,036 A | 4/1999 | McLeod |
| 5,914,129 A | 6/1999 | Mauskop |
| 5,922,704 A | 7/1999 | Bland |
| 5,922,766 A | 7/1999 | Acosta et al. |
| RE36,288 E | 8/1999 | Lin et al. |
| 5,932,624 A | 8/1999 | Herbert |
| 5,948,443 A | 9/1999 | Riley |
| 5,965,162 A | 10/1999 | Fuisz et al. |
| 5,976,548 A | 11/1999 | Hsia |
| 5,976,568 A | 11/1999 | Riley |
| 5,985,339 A | 11/1999 | Kamarei |
| 5,997,915 A | 12/1999 | Bailey |
| 6,013,665 A | 1/2000 | DeMichele et al. |
| 6,034,130 A | 3/2000 | Wang et al. |
| 6,036,992 A | 3/2000 | Borror et al. |
| 6,039,978 A | 3/2000 | Bangs et al. |
| 6,042,849 A | 3/2000 | Richardson |
| 6,048,846 A | 4/2000 | Cochran |
| 6,054,128 A | 4/2000 | Wakat |
| 6,090,414 A | 7/2000 | Passwater et al. |
| 6,093,425 A | 7/2000 | Kamarei |
| 6,099,871 A | 8/2000 | Martinez |
| 6,102,706 A | 8/2000 | Khoo et al. |
| 6,103,756 A | 8/2000 | Gorsek |
| 6,130,244 A | 10/2000 | DeMichele et al. |
| 6,136,345 A | 10/2000 | Grimmett et al. |
| 6,136,859 A | 10/2000 | Henriksen |
| 6,139,872 A | 10/2000 | Walsh |
| 6,159,505 A | 12/2000 | Piper |
| 6,207,651 B1 | 3/2001 | Allen |
| 6,214,373 B1 | 4/2001 | Snowden |
| 6,218,192 B1 | 4/2001 | Altura et al. |
| 6,228,388 B1 | 5/2001 | Paradissis et al. |
| 6,245,360 B1 | 6/2001 | Markowitz |
| 6,255,341 B1 | 7/2001 | DeMichele et al. |
| 6,258,846 B1 | 7/2001 | Hermelin et al. |
| 6,261,609 B1 | 7/2001 | Cates, II |
| 6,297,224 B1 | 10/2001 | Allen |
| 6,299,896 B1 | 10/2001 | Cooper et al. |
| 6,352,713 B1 | 3/2002 | Kirschner et al. |
| 6,361,800 B1 | 3/2002 | Cooper et al. |
| 6,383,471 B1 | 5/2002 | Chen |
| 6,383,543 B1 | 5/2002 | Reznik |
| 6,410,281 B1 | 6/2002 | Barclay |
| 6,440,450 B1 | 8/2002 | Han |
| 6,444,218 B2 | 9/2002 | Han et al. |
| 6,447,809 B1 | 9/2002 | Krumhar et al. |
| 6,451,341 B1 | 9/2002 | Slaga et al. |
| 6,451,567 B1 | 9/2002 | Barclay |
| 6,488,956 B1 | 12/2002 | Paradissis et al. |
| 6,495,177 B1 | 12/2002 | deVries et al. |
| 6,500,472 B2 | 12/2002 | Uchida et al. |
| 6,528,496 B1 | 3/2003 | Allen et al. |
| 6,565,891 B1 | 5/2003 | Chandra |
| 6,569,445 B2 | 5/2003 | Manning et al. |
| 6,572,888 B2 | 6/2003 | Byrd |
| 6,572,903 B1 | 6/2003 | Fuhr et al. |
| 6,576,253 B2 | 6/2003 | Manning et al. |
| 6,579,544 B1 | 6/2003 | Rosenberg |
| 6,607,900 B2 | 8/2003 | Bailey et al. |
| 6,660,293 B2 | 12/2003 | Giordano et al. |
| 6,753,350 B1 | 6/2004 | Hansen et al. |
| 6,777,391 B1 | 8/2004 | Kratky et al. |
| 6,814,983 B2 | 11/2004 | Giordano et al. |
| 6,818,228 B1 | 11/2004 | Walsdorf et al. |
| 6,849,613 B2 | 2/2005 | Prasad |
| 6,866,873 B2 | 3/2005 | Stern |
| 6,914,073 B2 | 7/2005 | Boulos et al. |
| 6,977,167 B2 | 12/2005 | Barclay |
| 7,390,509 B2 | 6/2008 | Giordano et al. |
| 7,422,758 B2 | 9/2008 | Block et al. |
| 7,704,542 B2 | 4/2010 | Bydlon et al. |
| 2001/0028897 A1 | 10/2001 | Hammerly |
| 2001/0029267 A1 | 10/2001 | Kuchan et al. |
| 2001/0046533 A1 | 11/2001 | Bailey |
| 2002/0004069 A1 | 1/2002 | Oppenheim et al. |
| 2002/0006959 A1 | 1/2002 | Henderson |
| 2002/0015742 A1 | 2/2002 | Jackson |
| 2002/0025310 A1 | 2/2002 | Bland |
| 2002/0031576 A1 | 3/2002 | Barrett-Reis et al. |
| 2002/0034543 A1 | 3/2002 | Kirschner et al. |
| 2002/0044961 A1 | 4/2002 | Kirschner et al. |
| 2002/0044969 A1 | 4/2002 | Harden |
| 2002/0045606 A1 | 4/2002 | Reddy |
| 2002/0058702 A1 | 5/2002 | Wang |
| 2002/0077315 A1 | 6/2002 | Leung et al. |
| 2002/0099020 A1 | 7/2002 | Abbruzzese et al. |
| 2002/0102330 A1 | 8/2002 | Schramm et al. |
| 2002/0110599 A1 | 8/2002 | Auweter et al. |
| 2002/0110632 A1 | 8/2002 | Nunes et al. |
| 2002/0119181 A1 | 8/2002 | Muszynska |
| 2002/0132035 A1 | 9/2002 | Tamarkin et al. |
| 2002/0132219 A1 | 9/2002 | McCleary |
| 2002/0136711 A1 | 9/2002 | Cochran |
| 2002/0137796 A1 | 9/2002 | Schade et al. |
| 2002/0138874 A1 | 9/2002 | Mukerji et al. |
| 2002/0142025 A1 | 10/2002 | Hageman |
| 2002/0172721 A1 | 11/2002 | Boulos et al. |
| 2002/0187205 A1 | 12/2002 | Paradissis et al. |
| 2002/0192265 A1 | 12/2002 | Manning et al. |
| 2002/0192310 A1 | 12/2002 | Bland et al. |
| 2003/0026860 A1 | 2/2003 | Lasekan et al. |
| 2003/0049352 A1 | 3/2003 | Mehansho et al. |
| 2003/0050341 A1 | 3/2003 | Bydlon et al. |
| 2003/0060509 A1 | 3/2003 | Elswyk |
| 2003/0068372 A1 | 4/2003 | Kirschner et al. |
| 2003/0077254 A1 | 4/2003 | Ramaekers |
| 2003/0077340 A1 | 4/2003 | Rao et al. |
| 2003/0078298 A1 | 4/2003 | Rao et al. |
| 2003/0082754 A1 | 5/2003 | Mukerji et al. |
| 2003/0086981 A1 | 5/2003 | Seiki et al. |
| 2003/0099753 A1 | 5/2003 | Yang |
| 2003/0104078 A1 | 6/2003 | Barrett-Reis |
| 2003/0104596 A1 | 6/2003 | Mukerji et al. |
| 2003/0108594 A1 | 6/2003 | Manning et al. |
| 2003/0113409 A1 | 6/2003 | Strassmann et al. |
| 2003/0144353 A1 | 7/2003 | Saebo et al. |
| 2003/0148418 A1 | 8/2003 | Pyntikov |
| 2003/0157144 A1 | 8/2003 | Mukerji et al. |
| 2003/0206969 A1 | 11/2003 | Nidamarty et al. |
| 2003/0215501 A1 | 11/2003 | Myatt et al. |
| 2004/0013784 A1 | 1/2004 | Costa |
| 2004/0013787 A1 | 1/2004 | Theuer |
| 2004/0022922 A1 | 2/2004 | Rutenberg |
| 2004/0038912 A1 | 2/2004 | Michelet et al. |
| 2004/0043043 A1 | 3/2004 | Schlyter |
| 2004/0071825 A1 | 4/2004 | Lockwood |
| 2004/0076664 A1 | 4/2004 | Bonura |
| 2004/0082536 A1 | 4/2004 | Cooper et al. |
| 2004/0096478 A1 | 5/2004 | Whippie et al. |
| 2004/0096522 A1 | 5/2004 | Lazarev |
| 2004/0097404 A1 | 5/2004 | Kessler et al. |
| 2004/0122246 A1 | 6/2004 | Sparso |
| 2004/0142017 A1 | 7/2004 | Luebbers |
| 2004/0151757 A1 | 8/2004 | Heirler |

| | | |
|---|---|---|
| 2004/0156882 A1 | 8/2004 | Davenport |
| 2004/0171152 A1 | 9/2004 | Price et al. |
| 2004/0202765 A1 | 10/2004 | McMahon et al. |
| 2004/0213853 A1 | 10/2004 | Byard et al. |
| 2004/0213857 A1 | 10/2004 | Soldati et al. |
| 2004/0214791 A1 | 10/2004 | Auestad et al. |
| 2004/0219188 A1 | 11/2004 | Comer et al. |
| 2004/0234579 A1 | 11/2004 | Finke |
| 2004/0253227 A1 | 12/2004 | Martin |
| 2004/0253320 A1 | 12/2004 | Nijhawan |
| 2005/0042329 A1 | 2/2005 | Chmura et al. |
| 2005/0058690 A1 | 3/2005 | Burgher et al. |
| 2005/0064014 A1 | 3/2005 | Finot et al. |
| 2005/0064068 A1 | 3/2005 | Shukla et al. |
| 2005/0070484 A1 | 3/2005 | Neu et al. |
| 2005/0100613 A1 | 5/2005 | Giordano et al. |
| 2005/0112211 A1 | 5/2005 | Gervais et al. |
| 2005/0136130 A1 | 6/2005 | Lang |
| 2005/0142124 A1 | 6/2005 | Kaiser |
| 2005/0170479 A1 | 8/2005 | Weaver et al. |
| 2005/0181058 A1 | 8/2005 | Hefel |
| 2005/0186296 A1 | 8/2005 | Palu et al. |
| 2005/0191368 A1 | 9/2005 | Harvey |
| 2005/0208179 A1 | 9/2005 | Albrecht et al. |
| 2005/0214383 A1 | 9/2005 | Bubnis et al. |
| 2005/0215640 A1 | 9/2005 | Baxter et al. |
| 2005/0226948 A1 | 10/2005 | Lee et al. |
| 2005/0240434 A1 | 10/2005 | Wooten et al. |
| 2005/0244510 A1 | 11/2005 | Smith |
| 2005/0249823 A1 | 11/2005 | Murphy et al. |
| 2005/0271791 A1 | 12/2005 | Wright |
| 2005/0277694 A1 | 12/2005 | Stock et al. |
| 2006/0024385 A1 | 2/2006 | Pedersen |
| 2006/0034916 A1 | 2/2006 | Giordano et al. |
| 2006/0051455 A1 | 3/2006 | Andersen et al. |
| 2006/0051462 A1 | 3/2006 | Wang |
| 2006/0057186 A1 | 3/2006 | Heller |
| 2006/0068038 A1 | 3/2006 | Harvey |
| 2006/0078593 A1 | 4/2006 | Strozier et al. |
| 2006/0083824 A1 | 4/2006 | Manning et al. |
| 2006/0088574 A1 | 4/2006 | Manning |
| 2006/0099693 A1 | 5/2006 | Kobzeff et al. |
| 2006/0115555 A1 | 6/2006 | Foulger |
| 2006/0165630 A1 | 7/2006 | Rubinstenn et al. |
| 2006/0165735 A1 | 7/2006 | Abril et al. |
| 2006/0188607 A1 | 8/2006 | Schramm |
| 2006/0210611 A1 | 9/2006 | Immig et al. |
| 2006/0217385 A1 | 9/2006 | Edwards et al. |
| 2006/0217386 A1 | 9/2006 | Edwards et al. |
| 2006/0240150 A1 | 10/2006 | Delaney et al. |
| 2006/0247310 A1 | 11/2006 | Shinohara et al. |
| 2006/0251722 A1 | 11/2006 | Bandak |
| 2006/0280776 A1 | 12/2006 | Koide |
| 2006/0280840 A1 | 12/2006 | Robertson |
| 2006/0286258 A1 | 12/2006 | Petschow et al. |
| 2007/0026049 A1 | 2/2007 | Auestad |
| 2007/0065556 A1 | 3/2007 | Martin |
| 2007/0098849 A1 | 5/2007 | Barrett-Reis et al. |
| 2007/0104741 A1 | 5/2007 | Murty |
| 2007/0104856 A1 | 5/2007 | Standal et al. |
| 2007/0116802 A1 | 5/2007 | Germano |
| 2007/0135376 A1 | 6/2007 | Henderson |
| 2007/0166411 A1 | 7/2007 | Anthony et al. |
| 2007/0190209 A1 | 8/2007 | Sinnott |
| 2007/0196436 A1 | 8/2007 | Abrahamse et al. |
| 2007/0207132 A1 | 9/2007 | Speelmans et al. |
| 2007/0212448 A1 | 9/2007 | Ohmori et al. |
| 2007/0218169 A1 | 9/2007 | Meiri-Bendek et al. |
| 2007/0253941 A1 | 11/2007 | Naidu et al. |
| 2007/0269493 A1 | 11/2007 | Lang |
| 2007/0281993 A1 | 12/2007 | Rozen |
| 2007/0292493 A1 | 12/2007 | Brierre |
| 2008/0003330 A1 | 1/2008 | Rueda et al. |
| 2008/0014315 A1 | 1/2008 | DeLease |
| 2008/0026063 A1 | 1/2008 | Ueda et al. |
| 2008/0026108 A1 | 1/2008 | Subramanian et al. |
| 2008/0038367 A1 | 2/2008 | Saloum |
| 2008/0038410 A1 | 2/2008 | Giordano |
| 2008/0044487 A1 | 2/2008 | Bruheim et al. |
| 2008/0058418 A1 | 3/2008 | D'Angelo et al. |
| 2008/0064635 A1 | 3/2008 | Rueda et al. |
| 2008/0096964 A1 | 4/2008 | Subramanian et al. |
| 2008/0102137 A1 | 5/2008 | Guffey |
| 2008/0152725 A1 | 6/2008 | Giordano et al. |
| 2008/0166466 A1 | 7/2008 | Palmano et al. |
| 2008/0182894 A1 | 7/2008 | Takino et al. |
| 2008/0193393 A1 | 8/2008 | Dayan |
| 2008/0193624 A1 | 8/2008 | Shulman et al. |
| 2008/0226757 A1 | 9/2008 | Morazzoni et al. |
| 2008/0233245 A1 | 9/2008 | White et al. |
| 2008/0268095 A1 | 10/2008 | Herzog |
| 2008/0274175 A1 | 11/2008 | Schramm et al. |
| 2008/0305096 A1 | 12/2008 | Verdegem et al. |
| 2008/0311100 A1 | 12/2008 | Manissier et al. |
| 2008/0317725 A1 | 12/2008 | Baum |
| 2009/0004281 A1 | 1/2009 | Nghiem et al. |
| 2009/0023678 A1 | 1/2009 | Murthy |
| 2009/0041914 A1 | 2/2009 | Rosevear |
| 2009/0068190 A1 | 3/2009 | Bortz |
| 2009/0074883 A1 | 3/2009 | Gupta |
| 2009/0117056 A1 | 5/2009 | Hodal, Jr. |
| 2009/0137459 A1 | 5/2009 | Gil Hernandez et al. |
| 2009/0143301 A1 | 6/2009 | Olson et al. |
| 2009/0186096 A1 | 7/2009 | Kritzman et al. |
| 2009/0192226 A1 | 7/2009 | Neu et al. |
| 2009/0220477 A1 | 9/2009 | Brown |
| 2009/0252853 A1 | 10/2009 | Gil Hernandez et al. |
| 2009/0306222 A1 | 12/2009 | Burton et al. |
| 2009/0311367 A1 | 12/2009 | Perry |
| 2010/0016430 A1* | 1/2010 | Long ............................ 514/558 |
| 2010/0021573 A1 | 1/2010 | Gonzalez et al. |
| 2010/0041622 A1 | 2/2010 | Bromley et al. |
| 2010/0055187 A1 | 3/2010 | Ahn |
| 2010/0055197 A1 | 3/2010 | Le-Henand et al. |
| 2010/0092604 A1 | 4/2010 | Mulder et al. |
| 2010/0094246 A1 | 4/2010 | Le-Henand et al. |
| 2010/0098779 A1 | 4/2010 | Balzer et al. |
| 2010/0113294 A1 | 5/2010 | Venkataraman et al. |
| 2010/0124587 A1 | 5/2010 | Heuer et al. |
| 2010/0129493 A1 | 5/2010 | Monster et al. |
| 2010/0129510 A1 | 5/2010 | Mulder et al. |
| 2010/0136168 A1 | 6/2010 | McHaney et al. |
| 2010/0143533 A1 | 6/2010 | Chang et al. |
| 2010/0150994 A1 | 6/2010 | Kotyla |
| 2010/0152107 A1 | 6/2010 | Le-Henand et al. |
| 2010/0159029 A1 | 6/2010 | Lang |
| 2010/0233280 A1 | 9/2010 | Driscoll |
| 2010/0247564 A1 | 9/2010 | Lee et al. |
| 2010/0247632 A1 | 9/2010 | Dong et al. |
| 2010/0255064 A1 | 10/2010 | Andersen et al. |
| 2010/0260836 A1* | 10/2010 | Giordano et al. ............. 424/456 |
| 2010/0266626 A1 | 10/2010 | Andersen et al. |
| 2010/0272660 A1 | 10/2010 | Malle |
| 2010/0291157 A1 | 11/2010 | L'europa |
| 2010/0292330 A1 | 11/2010 | Pan et al. |
| 2010/0316735 A1 | 12/2010 | Belliston |
| 2010/0317734 A1 | 12/2010 | Folan et al. |
| 2011/0008308 A1 | 1/2011 | Taylor et al. |
| 2011/0008388 A1 | 1/2011 | Navarro et al. |
| 2011/0020443 A1 | 1/2011 | Liu et al. |
| 2011/0045050 A1 | 2/2011 | Elbayoumi et al. |
| 2011/0064783 A1 | 3/2011 | Bang-Madsen et al. |
| 2011/0064860 A1 | 3/2011 | Lamb et al. |

FOREIGN PATENT DOCUMENTS

| | | |
|---|---|---|
| CN | 101322554 A | 12/2008 |
| CN | 101675804 A | 3/2010 |
| CN | 101675805 A | 3/2010 |
| CN | 101675806 A | 3/2010 |
| DE | 20116346 U1 | 1/2002 |
| EP | 0482715 | 4/1992 |
| EP | 682879 A1 | 11/1995 |
| EP | 696453 A2 | 2/1996 |
| EP | 696453 A3 | 6/1996 |
| EP | 0891719 | 1/1999 |
| EP | 1330957 A2 | 7/2003 |
| EP | 1366676 A1 | 12/2003 |
| EP | 2052727 A2 | 4/2009 |

| | | | |
|---|---|---|---|
| EP | 2305046 | A2 | 4/2011 |
| FR | 2829692 | A1 | 3/2003 |
| GB | 364503 | A | 1/1932 |
| GB | 431130 | A | 7/1935 |
| GB | 459657 | A | 1/1937 |
| GB | 660611 | A | 11/1951 |
| GB | 773622 | A | 5/1957 |
| GB | 822127 | A | 10/1959 |
| GB | 975387 | A | 11/1964 |
| GB | 2113521 | A | 8/1983 |
| JP | 2003012554 | A | 1/2003 |
| JP | 2003159028 | A | 6/2003 |
| WO | 9600584 | A1 | 1/1996 |
| WO | 9602988 | A1 | 10/1996 |
| WO | 9806277 | A1 | 2/1998 |
| WO | 9821953 | A2 | 5/1998 |
| WO | 9828978 | A1 | 7/1998 |
| WO | 9907419 | | 2/1999 |
| WO | 9953777 | A1 | 10/1999 |
| WO | 9966804 | A1 | 12/1999 |
| WO | 0020602 | A2 | 4/2000 |
| WO | 0020603 | A1 | 4/2000 |
| WO | 0212882 | A2 | 2/2002 |
| WO | 02076436 | A2 | 10/2002 |
| WO | 2004060487 | A1 | 7/2004 |
| WO | 2006087156 | A1 | 8/2006 |
| WO | 2006127934 | A2 | 11/2006 |
| WO | 2008039522 | A1 | 4/2008 |
| WO | 2008132713 | A1 | 11/2008 |
| WO | 2008147228 | A1 | 12/2008 |
| WO | 2008148552 | A2 | 12/2008 |
| WO | 2008154178 | A1 | 12/2008 |
| WO | 2009005351 | A1 | 1/2009 |
| WO | 2009017462 | A2 | 2/2009 |
| WO | 2010003790 | A1 | 1/2010 |
| WO | 2010018418 | A1 | 2/2010 |
| WO | 2010019598 | A1 | 2/2010 |
| WO | 2010030600 | A2 | 3/2010 |
| WO | 2010057804 | A1 | 5/2010 |
| WO | 2010079468 | A2 | 7/2010 |
| WO | 2010085149 | A1 | 7/2010 |
| WO | 2010125516 | A1 | 11/2010 |
| WO | 2011007102 | A1 | 1/2011 |
| WO | 2011031601 | A2 | 3/2011 |
| WO | 2011031602 | A1 | 3/2011 |

OTHER PUBLICATIONS

Llurba et al., 37(4) Free Radic. Biol. Med. 557-70 (2004).
Lee et al., 58(3} Eur. J. Clin. Nutr. 481-7 (2004).
Lemke et al., 44 J. Lipid Res. 1591-1600 (2003).
Lips et al., 86 J. Clin. Endocrinol. Metab. 1212-21 (2001).
Cheruku et al., Am J Clin Nutr 76:608-613 (2002).
Locksmith et al., 91(6) Obstet. Gynecol. 1027-34 (1998).
Laidlaw et al., Am J Clin Nutr 77: 37-42(2003).
Makoff, 25 Miner. Electrolyle Metab. 349-51 (1999).
Mares-Perlman et al., 153(5) Amer. J. Epidemiol. 424-432 (2001).
Martek Product Specifications Dhasco®-T, , V1-5/05, 2005.
Neuringer et al., Nutrition Reviews 44(9):285-294 (1986).
Mayne, 10 J. FASEB 690-701 (1996).
McNamara et al., vol. 75(4-5):237-57 (2006).
DiStefano et al., Gastroenterol vol. 122(7):1793-1799 (2002).
Milczarek et al., 210 Mol. Cell. Biochem. 65-73 (2000).
Monique et al., Am J Clin Nutr 71: 285S-291S (2000).
Morris et al., 13 J. Trace Elements Med. Biol. 57-61 (1999).
Moser-Veillon et al., 52 Am. J. Clin. Nutr. 135-41 (1990).
Myatt & Cui, 122(4) Histochem. Cell. Biol. 369-82 (2004).
Naude et al., 40(12) Journal of Clinical Pharmacology. 1447-51, (abstract only) (2000).
Notice of Failure to Comply with Ex Parte Reexamination Request Filing Requirements, Jul. 27, 2009.
Omenn et al., 334(18) New Eng. J. Med. 1150-1155 (1996).
Order granting motion to stay litigation pending reexamination, Nov. 24, 2009.
Order Granting Reexamination, Oct. 23, 2009.
Otto et al., vol. 69 (3):237-243 (2003).
Parfrey, 23 Advances in Nephrology 311-330 (1994).
PDR for Nutritional Supplements, selected pages, 2001.
Pediatric Dental Health, May 22, 2004.
Perna et al., 25 Mineral and Electrolyle Metabolism 95-99 (1999).
Perspectives in Nutrition, selected pages, 5th Edition, 2002.
Physicians Desk Reference, 1999 Edition, Vitafol-PN Caplet Product, (1999).
Plaintiffs Reply Brief in Support to Plaintiffs Motion for Preliminary Injunction as to Patent Claims, filed Sep. 2, 2009.
Plaintiffs Reply Brief in Support to Plaintiffs Motion for Preliminary Injunction as to Trademark Claims, filed Sep. 2, 2009.
Porkkala-Sarataho et al., 20 Arterioscler. Thromb. Vase. Biol. 2087-2093 (2000).
Rapp et al., 41 Invest. Ophthalmol. Vis. Sci. 1200-1209 (2000).
Reply to Notice of Failure to Comply with Ex Parte Reexamination Request Fling Requirements, Aug. 13, 2009.
Rioux et al., Acta Paediatrica, vol. 95(2):137-144 (2006).
Robinson et al., 94 Circulation 2743-48 (1996).
Rock et al., 96(7) J. Amer. Diet. Assoc. 693-702 (1996).
Rudich et al., 42 Dabetologia 949-957 (1999).
Schacky et al., Ann. of Internal Medicine 130:554-562 (1999).
Schlaich et al., 153 Atheroscelerosis 383-389 (2000).
Scholl et al., (146)(2) Amer. J. Epidem. 134-41 (1997).
Vitafol-PN Caplet Product, Physicians Desk Reference (1999).
Francois et al., Am. J. Clin. Nutr. 67(2): 301-8 (1998).
Lieberman et al., Alternative & Complementary Therapies 12(6): 310-314 (Dec. 2006).
Allman et al., Med. J. Australia 150: 130-33 (1999).
Anderson et al., Am. J. Clin. Nutr. 54: 909-916 (1991).
Anderson, Diabetes & Metabolism 26: 22-27 (2000).
Bazzarre et al., 12(2) J. Amer. Coil. Nutr. 162-69 (1993).
Berendschot et al., 41 Invest. Ophthalmol. Vis. Sci. 3322-3326 (2000).
Bernstein et al., 72 Exp. Eye Res. 215-223 (2001).
Seager, 50 J. Pharm. Pharmacol. 375-82 (1998).
Select—OB™ Product Insert, Jul. 2005.
Shah et al., 18(1) Amer. J. Kidney Dis. 84-90 (1991).
Shah et al., Am. J. Kidney Diseases 20(1): 42-49 (1992).
Shankar et al., Amer. J. Clin. Nutr. 68: 447S-463S (1998).
Day et al., Circulation 107: 2601-2606 (2003).
Shearer, The Lancet 345:229-34 (1995).
Shechter et al., 102 Circulation 2353-58 (2000).
Sifakis et al., 900 Ann. N.Y. Acad. Sci. 125-36 (2000).
Srinivas et al., 68(6) Indian J. Pediatr. 519-22 (2001).
Stampfer et al., 328 New Eng. J. Med. 1444-49 (1993).
Stein et al., 3 Blood Purification 52-62 (1985).
Stevens et al., Physiology & Behavior, vol. 59:915-920 (1996).
Stoll, Journal of Nutrition, vol. 87(3):193-198(2002).
Story et al., 27(1) Crit. Care Med. 220-23 (1999).
The VITATOPS Trial Study Group, 13 Cerebrovasc. Dis. 120-26 (2002).
Uauy et al., 67 Amer. J. Clin. Nutr. 9528-9598 (1998).
Van Der Put et al., Exp. Biol. Med. 116(4) 243-70 (2001).
Viitafol® product insert, Jul. 1997.
Zima et al., 17(4) Blood Purif. 182-86 (1999).
Vincent, Sports Medicine 33(3):213-30 (2003).
Vitafol® Syrup product label, 1997.
Vitafol®-PN product insert, Apr. 1997.
Vos, 161 Arch. Intern. Med. 774-75 (2001).
Weigel et al., 12 Cont. Clin. Trials 378-94 (1991).
Woods et al., 185(1 IAM. J. Obstet. Gvnecol. 5-10 (2001).
Yang et al., 13(4) Biomed. Environ. Sci. 280-86 (2000).
Young et al., Reprod. Nutr. Dev. vol. 45 :549-558 (2005).
Zacharski et al., 139(2) Amer. Heart J. 337-345 (2000).
Zile et al., 131(3) J. Nutr. 705-08 (2001).
1st Reexamination Request, Jul. 14, 2009.
2nd Reexamination Request, Sep. 18, 2009.
Amine et at, J, Nutrition, 101: 927-936 (1971).
Lapido, 72 (Supp.) Amer. J. Clin. Nutr. 280S-90S (2000).
Agus et al., 17 Crit. Care Clin. 175-87 (2001).
Black, 85(2)(Supp.) Brit. J. Nutr. S193-S97 (2001).
Blumberg et al., 20(5) Clin. Nephrol. 244-50 (1983).
Bostom et al., 49(1) Kidney Int. 147-52 (1996).
Bothwell, 72(SUDD.) AM. J. Clin. Nutr. 257S-64S (2000).
Braguer et al., 57 Nephron 192-96 (1991).

Burk, 3 Biological Activity of Selenium 53-70 (1983).
Burton et al., Ann. NY Acad. Sci. 7-22 (1998).
Carr et al., 87 Circ. Res. 349-354 (2000).
Cattaneo, 32(Supp 1) Ann. Med. 46-52 (2000).
Christian et al., 130(11) J. Nutr. 2675-82 (2000).
Smuts et al., The American College of Obstetricians and Gynecologists 101(3):469-479 (2003).
O'Neil-Cutting et al., JAMA 255:1468-1470 (1986).
Dawson-Hughes et al., 337 New Eng. J. Med. 670-76 (1997).
Defalco et al., 27 Clin. Exp. Obstet. Gvnecol. 188-90 (2000).
Defendant's Brief in Opposition to Plaintiffs Motion for Preliminary Injunction, filed Aug. 25, 2009.
Descombes et al., 24(10) Artificial Organs 773-78 (2000).
Dierkes et al., 11(2) J. Renal Nutr. 67-72 (2001).
Easterbauer et al., Free Rad. Biol. Med. 341-390 (1992).
Eskes, 27 Clin Exp. Obstet. Gynecol. 157-67 (2000).
Everett Laboratories, Inc.'s Complaint against River's Edge Pharmaceuticals, LLC, filed Jul. 14, 2009.
Everett Laboratories, Inc.'s Notice of Motion for Preliminary Injunction as to Trademark Claims, filed Jul. 31, 2009.
Everett Laboratories, Inc.'s Notice of Motion for Preliminary Injunction as to Patent Claims, filed Jul. 31, 2009.
Facchinetti et al., European review for medical and pharmacological sciences 9(1):41-48 (2005).
Francois et al., AM J Clin Nutr., 77:226-33 (2003).
Frank et al., 70(4) Int. J. Vitam. Nutr. Res. 159-66 (2000).
Parker et al., AM J Psychiatry 163(6):969-978 '(2006).

Groff et al., Advanced Nutrition and Human Metabolism 341 (2d ed. 1996).
Haberland et al., 113(2) Amer. Heart J. 573-577 (1987).
Hanratty et al., 85 Heart 326-330 (2001).
Helland et al., Pediatrics 111:39-44 (2003).
Heller et al., 276 J. Biol. Chem. 40-47 (2001).
Henkin et al., 91 Amer. J. Med. 239-246 (1991).
Henkin et al., 91(3) AM. J. Med. 239-46 (1991).
Henning et al., 95(9) Medizin. Klinik 477-81 (2000).
Henriksen et al., 3(2) Arteriosclerosis 149-159 (1983).
Holben et al., 99(7) Journal of the American Dietetic Assoc. 836-843 (1999).
Hoogeveen et al., 101 Circulation 1506-1511 (2000).
Horrocks et al., Pharmacological Research 40(3): 211-225 (1999).
House et al., 45(1) A8ALO J. 94-97 (1999).
Hu et al., JAMA, vol. 287 (14); 1815-1821 (2002).
Huang et al., 275(23) J. Biol. Chem. 17399-17406 (2000).
Islam et al., 150 Astherosclerosis 217-224 (2000).
Jergensen et al., LIPIDS 31(1): 99-105 (1996).
Jaarsveld et al., 99(1) Res. Comm. Mol. Pathol. Pharmacol. 69-80 (1988).
Javaid et al., The Lancet 367(9504): 36-43 (2006).
Wagner et al., Pediatrics 122(5):1142-1152 (2008).
Wagner et al., Pediatrics 123(1):197 (2009).
Vieth et al., Am. J. Clin. Nutr. 73:288-294 (2001).

* cited by examiner

COMPOSITIONS, KITS AND METHODS FOR NUTRITION SUPPLEMENTATION

FIELD OF THE INVENTION

The present invention relates to various vitamin, nutrient and mineral compositions and kits for nutritional supplementation and methods of administration of compositions and kits for nutitional supplementation in, for example, subjects in physiologically stressful states, such as occur during pregnancy, lactation, or in need thereof.

BACKGROUND OF THE INVENTION

Nutrition plays a critical role in maintaining good health. Proper nutrition prevents dietary deficiencies, and also protects against the development of disease. When the body faces physiological stress, proper nutrition plays an increasingly important role. For example, pregnancy and lactation are among the most nutritionally volatile and physiologically stressful periods and processes in the lifetimes of women. Vitamin and mineral needs are almost universally increased during these natural processes. Increased vitamin and mineral needs during these times are almost always due to elevated metabolic demand, increased plasma volume, increased levels of blood cells, decreased concentrations of nutrients, and decreased concentrations of nutrient-binding proteins.

When increased nutrient needs occur during pregnancy, lactation, or any other physiologically stressful state, nutritional supplementation serves a vital role in maintaining good health. Nutritional supplementation is especially pertinent to women contemplating conceiving a child because optimizing specific nutrients before, during, and after the physiological processes of pregnancy or lactation can have profound, positive, and comprehensive impacts upon the overall wellness of the developing and newborn child as well as on the safety and health of the mother. The present invention provides compositions, kits and methods designed to supplement the nutritional needs of individuals in physiologically stressful states.

Supplementation with certain vitamins and minerals serves a role in protecting against disease and contributes to the overall health of the mother and developing child. Specifically, vitamins, nutrients and minerals such as twelve carbon chain fatty acids and/or twelve carbon chain acylglycerols (such as lauric acid and monolaurin respectively) vitamin D, iodine, vitamin B1, vitamin B6, vitamin B12, vitamin B2, vitamin B9, vitamin B3, vitamin E, vitamin A, vitamin C, iron, zinc, copper, magnesium, and omega 3 fatty acids such as docosahexaenoic acid (DHA), play integral roles in physiological mechanisms that serve to prevent, treat and/or alleviate the occurrence or negative effects of some diseases.

Indeed, for example, twelve carbon chain fatty acids or twelve carbon chain acylglycerols such as lauric acid and monolaurin have bactericidal, antiviral, antifungal and thus overall anti-infectious benefits. Lieberman et al., ALTERNATIVE & COMPLEMENTARY THERAPIES, 310-314 (December 2006). In addition, twelve carbon chain fatty acids or twelve carbon chain acylglycerols such as lauric acid and monolaurin are provided in mothers milk and thus may provide such beneficial effects to an infant. There is not, however, a nutritional supplement for example, prenatal and pregnant women, that provides an exogenous supplementation of these compounds in a multiple nutritional supplement.

Iodine also provides nutritional benefits as it is an essential component of the thyroid hormones that are involved in the regulation of various enzymes and metabolic processes, such as thyroxine and triiodothyronine. Indeed, iodine deficiency disorders (IDD) include mental retardation, hypothyroidism, goiter, cretinism, and varying degrees of other growth and developmental abnormalities which can be a result from inadequate thyroid hormone production from lack of sufficient iodine. See, for example, Food and Nutrition Board and Institute of Medicine, DIETARY REFERENCE INTAKES FOR VITAMIN A, VITAMIN K, ARSENIC, BORON, CHROMIUM, COPPER, IODINE, IRON, MANGANESE, MOLYBDENUM, NICKEL, SILICON, VANADIUM, AND ZINC (2001), page 260. Further, iodine is an important element in breast milk for infant nutrition. An adequate concentration of iodine in breast milk is essential to provide for optimal neonatal thyroid hormone stores and to prevent impaired neurological development in breast-fed neonates. In many countries of the world, low iodine content of the breast milk indicates less than optimum maternal and infant iodine nutrition. F. Azizi et al., CLIN ENDOCRINOL, 70(5):803-9 (2009). Multivitamin and multi nutritional supplements, for example for prenatal pregnant or breast-feeding women, are also lacking or deficient in the dosage amount of this important mineral.

In another example, there is a need for a nutritional supplement with increased vitamin D, in for example, a prenatal or dietary supplement, as recent research suggests that vitamin D has more positive physiological effects than previous thought, in for example prenatal and pregnant women. It has recently been determined that vitamin D has previously unknown roles in the enhancement of vascular function, defense against cancer, immuno-competence, blood pressure regulation and possessing the ability to enhance cellular insulin sensitivity in the human body. Due to the additional roles that vitamin D plays in the human body, it has recently been determined that higher daily vitamin D intake beyond current recommendations may be associated with better health outcomes. Indeed, studies suggest increasing the serum level of 25-hydroxyvitamin D, a beneficial derivative of vitamin D, to a 30 ng/ml serum range. A 30 ng/ml appears to be the most advantageous serum level in recent studies reviewing patient bone mineral density (BMD), lower extremity function, dental health, risk of falls, admission to nursing home, fractures, cancer prevention and incident hypertension. Bischoff-Ferrari H A, ADV EXP MED BIOL. 624:55-71 (2008). Effective and safe doses of vitamin D to bring serum levels of 25-hydroxyvitamin D up to a desirable level of 30 ng/ml is currently needed.

Lastly, a present problem with nutritional supplements that include multiple vitamins, nutrients and minerals is the ability to include all the components in one composition. Providing a single composition multivitamin and multinutrient supplement is an appealing feature because it improves patient compliance. Patients, and specifically for example, pregnant patients, often have nausua, and may have difficulty swallowing nutritional supplements. Compliance issues regarding taking multiple pills may therefore result. A one pill or one composition nutritional supplement that includes the beneficial vitamins, nutrients and minerals in appropriate dosage amounst would thus be beneficial for improving patient compliance in for example, pregnant women. A difficulty in the nutrition supplement market, however, is the ability to include multiple vitamins, minerals and nutrients of various water or fat solubilities in the needed dosage amounts all in one composition. For example, nuturional supplements that include fat soluble compounds such as DHA and water soluble vitamins such as B-complex vitamins and vitamin C, are often separated into multiple compositions. A supplement comprising multiple vitamins, nutrients and minerals blended to form a single composition, is thus currently needed. In a specific example, the single composition may be in the form of a gelcap. Patient compliance is also improved if a gelcap is used to administer the drug because of its soft and elastic nature, which makes it easier to swallow compared to a hard tablet or caplet.

A liquid gelcap also has numerous advantages. First, it retains many of the advantages of consumer acceptance and is easier to swallow due to the outer coating being a soft and elastic gelatin shell. Also, concentrated liquid compositions are well suited for encapsulation within a soft gelatin shell, creating flexibility that further assists in the capsule being easier to swallow. The active drug contained in the liquid form also provides advantages by dispersing the drug to the active site. For example, the active drug does not first have to dissolve in the gastrointestinal tract, thereby facilitating absorption of the pharmacologically active substance. See, for example, U.S. Pat. No. 6,689,382, which is expressly incorporated by reference herein. Other formulations take advantage of the liquid form by creating a sustained release gelatin capsule, thereby permitting the delivery of the drug in a controlled fashion. See, for example, U.S. Pat. Nos. 5,324,280 and 6,929,803, which are expressly incorporated by reference herein.

SUMMARY OF THE INVENTION

The present invention provides compositions and kits and methods of administering compositions and kits for both prophylactic and therapeutic nutritional supplementation. Specifically, for example, the present invention relates to novel compositions and kits of vitamins and minerals that can be used to supplement the nutritional deficiencies observed in patients throughout physiologically stressful states, which, in certain embodiments of the present invention, include prenatal, pregnant and breast-feeding women.

One embodiment of the present invention may include a nutritional supplement wherein multiple vitamins, minerals and nutrients are provided in one composition. In a specific embodiment, the composition may be a gelcap. In one embodiment of the present invention, the composition may comprise a twelve carbon chain fatty acid or twelve carbon chain acylglycerol, vitamin D, iodine, vitamin B1, vitamin B6, vitamin B12, vitamin B2, vitamin B9, vitamin B3, vitamin E, vitamin A, vitamin C, iron, zinc, copper, magnesium, omega 3 fatty acids and one or more pharmaceutically acceptable carriers.

In one embodiment of the present invention, vitamin D may be included in the form selected from one or more of the group consisting of vitamin D3 (calciol or cholecalciferol or colecalciferol), vitamin D2 (calciferol, ergocalciol, ergocalciferol, ercalciol, Deltalin or Viosterol), previtamin D2, ergosterol, calcitriol (1,25-dihydroxycholecalciferol), 7-dehydrocholesterol, vitamin D1, vitamin D4 (also known as 22-dihydroergocalciferol, 22,23-dihydroercalciol or (24S)-methylcalciol), vitamin D5 (also known as (24S)-Ethylcalciol or sitocalciferol), 7-dehydrositosterol, Lumisterol, 25-hydroxyvitamin D, all steroids that exhibit the biological activity of calciol, 25-fluorocalciol, (3S)-3-amino-3-deoxycalciol, 11α-acetoxycalciol, calcidiol (25-hydroxycholecalciferol or calcifediol), ercalcitriol, calcitetrol, tacalciol (tachysterol3), (5E)-isocalciol (isovitamin D3), Dihydroercalciol (dihydrotachysterol3), (1S)-Hydroxycalciol (also known as 1α-hydroxycholecalciferol or alfacaleidol), (24R)-Hydroxycalcidiol (also known as 24(R),25-dihydroxycholecalciferol), Ercalcidiol, Ercalcitriol, Ertacalciol, (5E)-(10S)-10,19-Dihydroercalciol (dihydrotachysterol2), (6Z)-Tacalciol (precalciferol or pre-vitamin D), and (22E)-(24R)-Ethyl-22,23-didehydrocalciol (vitamin D6).

In another embodiment, the compositions may include vitamin B1 in the form selected from one or more of the group consisting of thiamine, thiamine monophosphate, thiamine diphosphate, thiamine triphosphate, acetiamine, allithiamine, prosultiamine and S-acyl derivatives of thiamine such as benfotiamine, fursultiamine and salts and esters thereof. In another embodiment, the compositions may include vitamin B1 in the form selected from one or more of the group consisting of thiamine, thiamine monophosphate, thiamine diphosphate, thiamine triphosphate, acetiamine, allithiamine, prosultiamine and S-acyl derivatives of thiamine such as benfotiamine, fursultiamine and salts and esters thereof.

In another embodiment, the compositions may include vitamin A in the form selected from one or more of the group consisting of retinol acetate (retinyl acetate or vitamin A acetate), retinol (vitamin A alcohol), retinol palmitate (retinyl palmitate or vitamin A palmitate), retinoic acid (tretinoin), retinal, beta-cryptoxanthin, alpha-carotene, beta-carotene, gamma-carotene, and provitamin A carotenoids. In a specific embodiment, vitamin A may be included in the form of beta carotene.

In another embodiment, the compositions may include vitamin B9 in the form selected from one or more of the group consisting of folic acid, folinic acid, folacin, metafolin, and/or one or more natural isomers of folate including (6S)-tetrahydrofolic acid or a polyglutamyl derivative thereof, (6S,R)-tetrahydrofolic acid or a polyglutamyl derivative thereof, 5-methyl-(6S)-tetrahydrofolic acid or a polyglutamyl derivative thereof, 5-methyl-(6S,R)-tetrahydrofolic acid or a polyglutamyl derivative thereof, 5-formyl-(6S)-tetrahydrofolic acid or a polyglutamyl derivative thereof, 10-formyl-(6R)-tetrahydrofolic acid or a polyglutamyl derivative thereof, 5,10-methylene-(6R)-tetrahydrofolic acid or a polyglutamyl derivative thereof, 5,10-methenyl-(6R)-tetrahydrofolic acid or a polyglutamyl derivative thereof and 5-formimino-(6S)-tetrahydrofolic acid or a polyglutamyl derivative thereof and their salts and esters thereof. In another embodiment, the compositions may include vitamin B2 in the form selected from one or more of the group consisting of flavin mononucleotide (FMN), flavin adenine dinucleotide (FAD), riboflavin (also known as 7,8-dimethyl-10-((2R,3R,4S)-2,3,4,5-tetrahydroxypentyl)benzo[g]pteridine-2,4(3H,10H)— dione or lactoflavin) and riboflavin derivatives such as riboflavin-5'-monophosphate, riboflavin-5'-monobutyrate and riboflavin-5'-monopalmitate.

In another embodiment, the compositions may include vitamin B3 in the form selected from one or more of the group consisting of niacin (nicotinic acid or pyridine-3-carboxylic acid), and nicotinamide (niacinamide) and salts and esters thereof. In another embodiment, the compositions may include vitamin B6 in the form selected from one or more of the group consisting of pyridoxine, 3-hydroxy-4,5-bis(hydroxymethyl)-2-methylpyridine, 5'-deoxypyridoxal, 2-demethylpyridoxal(2-norpyridoxal), 2-propyl-2-norpyridoxal (2'-ethylpyridoxal), 6-methylpyridoxal, 2'-hydroxypyridoxal (2-hydroxymethyl-2-demethylpyridoxal or 2-hydroxymethyl-2-norpyridoxal), 4'-deoxypyridoxine 5'-phosphate, 5'-methylpyridoxal-5'-phosphate, pyridoxal N-oxide 5'-phosphate, Pyridoxal, Pyridoxamine, Pyridoxine-5'-phosphate (PNP), pyridoxal-5'-phosphate (PLP) and pyridoxamine-5'-phosphate (PMP), and their salts and chelates thereof. In another embodiment, the compositions may include vitamin B12 in the form selected from one or more of the group consisting of cobalamin, methylcobalamin, 5'-deoxyadenosylcobalamin (adenosylcobalamin or cobamamide), cyanocobalamin, hydroxycobalamin and mecobalamin.

In another embodiment, the compositions may include vitamin E in the form selected from one or more of the group consisting of alpha, beta, gamma, and delta tocopherols in its natural or synthetic (dl) forms; alpha, beta, gamma, and delta tocotrienols in its natural or synthetic (dl) forms, dl-alpha tocopheryl derivatives such as dl-alpha tocopheryl esters, dl-alpha-tocopheryl acetate or succinate and d-alpha-tocopheryl acetate or dl-alpha tocopheryl phosphates (such as Ester-E®). In another embodiment, the compositions may include vitamin C in the form selected from one or more of the group consisting of ascorbic acid, ascorbates (calcium or sodium ascorbate), dehydroascorbic acid and salts, ascorbyl palmitate, ascorbyl phosphates and salts (such as sodium or magnesium ascorbyl phosphate), ascorbyl tetraisopalmitate, tetrahexyldecyl ascorbate, ascorbyl sulfates and salts, acylated ascorbic acid derivatives (such as 6-O-acyl-2-O-alpha-D-glucopyranosyl-L-ascorbic acids), 6-bromo-6-deoxy-L-ascorbic acid, and ascorbate salts. In another embodiment, the compositions may include iron in the form selected from one or more of the group consisting of elemental iron, in the form of a salt, chelated form, non-chelated form, chelated to an amino acid, carbonyl iron, ferrous gluconate, ferrous fumarate, polysaccharide iron complex, elemental polysaccharide iron, polysaccharide iron, ferrous (II)-bis-glycinate chelate, ferrous asparto glycinate, ferrous bisglycinate, ferrous bisglycinate hydrochloride, ferrous bisglycinate, elemental ferrous bisglycinate, ferrous sulfate, ferronyl (micronized), as Iron Aid, iron protein succinylate, carbonyl iron, Sumalate iron, Heme iron complex, as Ferrochel amino acid chelate, Heme iron polypeptide as Proferrin-bovine source, as heme iron polypeptide (bovine source) as sodium iron EDTA (Ferrazone), ferric ammonium citrate, elemental iron, and ferric pyrophosphate.

In another embodiment, the compositions may include zinc in the form selected from one or more of the group consisting of elemental zinc, in the form of a salt, in a chelated form, in a non-chelated form, zinc acetate, zinc gluconate, zinc picolinate, zinc sulfate and zinc oxide. In another embodiment, the compositions may include copper in the form selected from one or more of the group consisting of elemental copper, in the form of a salt, in a chelated form, in a non-chelated form, cupric oxide, copper sulfate, copper gluconate, copper citrate, cupric acetate, alkaline copper carbonate, and copper salicylate. In another embodiment, the compositions may include magnesium in the form selected from one or more of the group consisting of elemental magnesium, in the form of a salt, in a chelated form, in a non-chelated form, magnesium acetate, magnesium carbonate, magnesium gluconate, magnesium chloride, magnesium citrate, magnesium silicate, magnesium stearate, magnesium sulfate, magnesium oxide, and magnesium chelated to an amino acid (magnesium glycinate, magnesium aspartate).

In another embodiment, the compositions may include omega 3 fatty acids in the form selected from one or more of the group consisting docosahexaenoic acid (DHA), eicosapentaenoic acid (EPA) and α-linolenic acid (ALA). In a specific embodiment of the present invention, omega 3 fatty acids may comprise DHA. In another embodiment, the source of DHA comprises one or more of the group consisting of animal, fish, plants, algae or microorganism production. In one specific embodiment, the source of DHA may be algae oil. In another specific embodiment, the source of DHA may be fish oil. In another embodiment, the source of DHA my be a mixture of algae oil and fish oil, in any appropriate proportion.

In another embodiment, the compositions may include twelve carbon chain fatty acids or twelve carbon chain acylglycerols comprising one or more of the group consisting of lauric acid, glycerol monolaurate (monolaurin), dilaurin, trilaurin, a twelve carbon chain monoacylglycerol, a twelve carbon chain unsaturated fatty acid, a diacylglycerol comprising at least one twelve carbon chain and a triacylglyceral comprising at least one twelve carbon chain.

In one embodiment of the present invention, the twelve carbon chain fatty acid or twelve carbon chain acylglycerol comprises lauric acid. In another specific embodiment, lauric acid may be derived from a natural or synthetic source or may be derived from a genetically modified or engineered source. In another embodiment, the source of lauric acid may be from one or more of the group consisting of algae oil, coconut oil, babassu oil, and palm kernel oil.

In another embodiment, the compositions may include iodine in the form selected from one or more of the group consisting of iodide, elemental iodine, iodized salt, Lugol's iodine, sodium iodide, potassium iodide, potassium iodate, nascent iodine, and Nano-Colloidal Detoxified Iodine.

In another embodiment, the compositions may include vitamin D in the form of vitamin D3 in an amount of about 400 I.U. to about 1600 I.U. or about 10 µg to about 40 µg. In a specific embodiment, vitamin D may be in the form of vitamin D3 and may be present in an amount of about 1000 I.U. or 25 µg.

In another embodiment, the compositions may include twelve carbon chain fatty acid or twelve carbon chain acylglycerols, or mixtures thereof, in an amount of about 30 mg to about 300 mg. In a specific embodiment, the twelve carbon chain fatty acids or twelve carbon chain acylglycerols may be derived from one or more selected from the group consisting of coconut oil and algae oil and may be present in a total amount of about 30 mg to about 300 mg.

In another specific embodiment, the twelve carbon chain fatty acid or twelve carbon chain acylglycerol may be lauric acid derived from one or more selected from the group consisting of coconut oil and algae oil and may be present in a total amount of about 60 mg. In another embodiment, the compositions may include iodine in an amount of about 100 µg to about 300 µg. In a specific embodiment, iodine may be present in an amount of about 200 µg. In another embodiment, the compositions may include vitamin B1 in an amount of about 0.8 mg to about 2.4 mg. In a specific embodiment, vitamin B1 may be present in an amount of about 1.6 mg. In another embodiment, the compositions may include vitamin B6 in an amount of about 1.2 mg to about 3.8 mg. In a specific embodiment, vitamin B6 may be present in an amount of about 2.5 mg. In another embodiment, the compositions may include vitamin B12 in an amount of about 6 µg to about 18 µg. In a specific embodiment, vitamin B12 may be present in an amount of about 12 µg. In another embodiment, the compositions may include vitamin B2 in an amount of about 0.9 mg to about 2.7 mg. In a specific embodiment, vitamin B2 may be present in an amount of about 1.8 mg. In another embodiment, the compositions may include vitamin B9 in an amount of about 0.5 mg to about 1.5 mg. In a specific embodiment, vitamin B9 may be present in an amount of about 1.0 mg. In another embodiment, the compositions may include vitamin E in an amount of about 5 I.U. to about 15 I.U. In another specific embodiment, vitamin E may be present in an amount of about 10 I.U. In another embodiment, the compositions may include vitamin A in the form of beta carotene and in an amount of about 550 I.U. to about 1650 I.U. or about 330 µg to about 990 µg. In a specific embodiment, vitamin A may be in the form of beta carotene and present in an amount of about 1100 I.U. or 660 µg. In another embodiment, the compositions may include vitamin C in an amount of about 6 mg to about 18 mg. In a specific embodiment, vitamin C may be present in an amount of about 12 mg. In another embodiment, the compositions may include vitamin B3 in the form of nicotinamide and in an amount of about 7.5 mg to about 22.5 mg. In a specific embodiment, vitamin B3 may be in the form of nicotinamide and present in an amount of about 15 mg.

In another embodiment, the compositions may include iron in an amount of about 13.5 mg to about 40.5 mg. In a specific embodiment, iron may be present in an amount of about 27 mg. In another embodiment, the compositions may include zinc in an amount of about 7.5 mg to about 22.5 mg. In a specific embodiment, zinc may be present in an amount of about 15 mg. In another embodiment, the compositions may include copper in an amount of about 1.0 mg to about 3.0 mg. In a specific embodiment, copper may be present in an amount of about 2.0 mg. In another embodiment, the compositions may include magnesium in an amount of about 2.5 mg to about 7.5 mg. In a specific embodiment, magnesium may be present in an amount of about 5 mg.

In another embodiment, the compositions may include DHA in an amount of about 100 mg to about 300 mg. In a specific embodiment, DHA may be present in an amount of about 200 mg.

In another embodiment, the compositions may include vitamin D in an amount of about 500 I.U. to about 1500 I.U., twelve carbon chain fatty acid and/or twelve carbon chain acylglycerols in an amount of about 30 mg to about 300 mg, iodine in an amount of about 100 μg to about 300 μg, vitamin B1 in an amount of about 0.8 mg to about 2.4 mg, vitamin B6 in an amount of about 1.2 mg to about 3.8 mg, vitamin B12 in an amount of about 6 μg to about 18 μg, vitamin B2 in an amount of about 0.9 mg to about 2.7 mg, vitamin B9 in an amount of about 0.5 mg to about 1.5 mg, vitamin E in an amount of about 5 I.U. to about 15 I.U., vitamin A in an amount of about 550 I.U. to about 1650 I.U., vitamin C in an amount of about 6 mg to about 18 mg, vitamin B3 in an amount of about 7.5 mg to about 22.5 mg, iron in an amount of about 13.5 mg to about 40.5 mg, zinc in an amount of about 7.5 mg to about 22.5 mg, copper in an amount of about 1.0 mg to about 3.0 mg, magnesium in an amount of about 2.5 mg to about 7.5 mg, and omega 3 fatty acids in an amount of about 100 mg to about 300 mg. In another embodiment, the compositions may include vitamin D in an amount of about 1000 I.U., twelve carbon chain fatty acid or twelve carbon chain acylglycerol comprising lauric acid amount of about 60 mg, iodine in an amount of about 200 μg, vitamin B1 in an amount of about 1.6 mg, vitamin B6 in an amount of about 2.5 mg, vitamin B12 in an amount of about 12 μg, vitamin B2 in an amount of about 1.8 mg, vitamin B9 in an amount of about 1.0 mg, vitamin E in an amount of about 10 I.U., vitamin A in an amount of about 1100 I.U., vitamin C in an amount of about 12 mg, vitamin B3 in an amount of about 15 mg, iron in an amount of about 27 mg, zinc in an amount of about 15 mg, copper in an amount of about 2.0 mg, magnesium in an amount of about 5 mg, and omega 3 fatty acids comprising DHA in an amount of about 200 mg.

In another specific embodiment, the compositions may be provided in a dosage form selected from one or more of the group consisting of a capsule, tablet, caplet, gel caplet (gelcap), syrup, a liquid composition, a concentrated powder, and a concentrated powder admixed with a liquid. In another specific embodiment, the compositions may be a dietary supplement. In another embodiment, the compositions may be a prescription prenatal vitamin.

One embodiment of the present invention may include a nutritional supplement wherein multiple vitamins, minerals and nutrients are provided in a kit. In a specific embodiment, the kits may comprise a first composition comprising one or more vitamins, minerals or nutrients selected from the group consisting of vitamin D, twelve carbon chain fatty acid or twelve carbon chain acylglycerol, iodine, vitamin B1, vitamin B6, vitamin B12, vitamin B2, vitamin B9, vitamin B3, vitamin E, vitamin A, vitamin C, iron, zinc, copper, magnesium and omega 3 fatty acids; and one or more pharmaceutically acceptable carriers; and a second composition comprising one or more vitamins, minerals or nutrients selected from the group consisting of vitamin D, twelve carbon chain fatty acid or twelve carbon chain acylglycerol, iodine, vitamin B1, vitamin B6, vitamin B12, vitamin B2, vitamin B9, vitamin B3, vitamin E, vitamin A, vitamin C, iron, zinc, copper, magnesium and omega 3 fatty acids; and one or more pharmaceutically acceptable carriers; wherein the first composition and the second composition collectively comprise vitamin D, lauric acid, iodine, vitamin B1, vitamin B6, vitamin B12, vitamin B2, vitamin B9, vitamin B3, vitamin E, vitamin A, vitamin C, iron, zinc, copper, magnesium and omega 3 fatty acids, and one or more pharmaceutically acceptable carriers.

In another embodiment of the present invention, the first composition and the second composition may collectively comprise vitamin D in an amount of about 500 I.U. to about 1500 I.U., twelve carbon chain fatty acid or twelve carbon chain acylglycerol in an amount of about 30 mg to about 300 mg, iodine in an amount of about 100 μg to about 300 μg, vitamin B1 in an amount of about 0.8 mg to about 2.4 mg, vitamin B6 in an amount of about 1.2 mg to about 3.8 mg, vitamin B12 in an amount of about 6 μg to about 18 μg, vitamin B2 in an amount of about 0.9 mg to about 2.7 mg, vitamin B9 in an amount of about 0.5 mg to about 1.5 mg, vitamin E in an amount of about 5 I.U. to about 15 I.U., vitamin A in an amount of about 550 I.U. to about 1650 I.U., vitamin C in an amount of about 6 mg to about 18 mg, vitamin B3 in an amount of about 7.5 mg to about 22.5 mg, iron in an amount of about 13.5 mg to about 40.5 mg, zinc in an amount of about 7.5 mg to about 22.5 mg, copper in an amount of about 1.0 mg to about 3.0 mg, magnesium in an amount of about 2.5 mg to about 7.5 mg, and omega 3 fatty acids in an amount of about 100 mg to about 300 mg.

In another embodiment of the present invention, the first composition and second composition may collectively comprise vitamin D in an amount of about 1000 I.U., twelve carbon chain fatty acid or twelve carbon chain acylglycerol comprising lauric acid in an amount of about 60 mg, iodine in an amount of about 200 μg, vitamin B1 in an amount of about 1.6 mg, vitamin B6 in an amount of about 2.5 mg, vitamin B12 in an amount of about 12 μg, vitamin B2 in an amount of about 1.8 mg, vitamin B9 in an amount of about 1.0 mg, vitamin E in an amount of about 10 I.U., vitamin A in an amount of about 1100 I.U., vitamin C in an amount of about 12 mg, vitamin B3 in an amount of about 15 mg, iron in an amount of about 27 mg, zinc in an amount of about 15 mg, copper in an amount of about 2.0 mg, magnesium in an amount of about 5 mg, and omega 3 fatty acids comprising DHA in an amount of about 200 mg.

In a specific embodiment of the kit of the present invention, the first composition may be in a dosage form selected from the group consisting of a capsule, tablet, caplet, gel caplet (gelcap), syrup, a liquid composition, a concentrated powder, and a concentrated powder admixed with a liquid; and the second composition may be in a dosage form selected from the group consisting of a capsule, tablet, caplet, gel caplet (gelcap), syrup, a liquid composition, a concentrated powder, and a concentrated powder admixed with a liquid.

In another embodiment of the present invention, the kit may be a dietary supplement. In a specific embodiment, the kit may be a prescription prenatal vitamin. In another specific embodiment, the kit may be administered once a day. In another specific embodiment, the kit may be administered twice a day. In another specific embodiment, the first composition and the second composition of the kit may be co-administered at the same time.

One embodiment of the present invention may include administering compositions and kits comprising multiple vitamins, minerals and nutrients for supplementation or for propylactic use as prevention against disease. In one embodiment of the present invention, the methods may comprise administering a composition comprising a twelve carbon chain fatty acid and/or twelve carbon chain acylglycerols, vitamin D, iodine, vitamin B1, vitamin B6, vitamin B12, vitamin B2, vitamin B9, vitamin B3, vitamin E, vitamin A, vitamin C, iron, zinc, copper, magnesium, omega 3 fatty acids and one or more pharmaceutically acceptable carriers to a patient. In a specific embodiment, the patient may be a human. In another specific embodiment, the human may be a woman. In another specific embodiment, the woman may be pregnant, prenatal or breast-feeding.

In another specific embodiment, the methods may comprise administering a composition comprising vitamin D in an amount of about 500 I.U. to about 1500 I.U., twelve carbon chain fatty acid or twelve carbon chain acylglycerols in an amount of about 30 mg to about 300 mg, iodine in an amount of about 100 μg to about 300 μg, vitamin B1 in an amount of about 0.8 mg to about 2.4 mg, vitamin B6 in an amount of about 1.2 mg to about 3.8 mg, vitamin B12 in an amount of about 6 μg to about 18 μg, vitamin B2 in an amount of about 0.9 mg to about 2.7 mg, vitamin B9 an amount of about 0.5 mg to about 1.5 mg, vitamin E in an amount of about 5 I.U. to about 15 I.U., vitamin A in an amount of about 550 I.U. to about 1650 I.U., vitamin C in an amount of about 6 mg to about 18 mg, vitamin B3 in an amount of about 7.5 mg to about 22.5 mg, iron in an amount of about 13.5 mg to about 40.5 mg, zinc in an amount of about 7.5 mg to about 22.5 mg, copper in an amount of about 1.0 mg to about 3.0 mg, magnesium in an amount of about 2.5 mg to about 7.5 mg, and omega 3 fatty acids in an amount of about 100 mg to about 300 mg.

In another specific embodiment, the methods may comprise administering a composition comprising vitamin D in an amount of about 1000 I.U., twelve carbon chain fatty acid or twelve carbon chain acylglycerol comprising lauric acid in an amount of about 60 mg, iodine in an amount of about 200 μg, vitamin B1 in an amount of about 1.6 mg, vitamin B6 in an amount of about 2.5 mg, vitamin B12 in an amount of about 12 μg, vitamin B2 in an amount of about 1.8 mg, vitamin B9 in an amount of about 1.0 mg, vitamin E in an amount of about 10 I.U., vitamin A in an amount of about 1100 I.U., vitamin C in an amount of about 12 mg, vitamin B3 in an amount of about 15 mg, iron in an amount of about 27 mg, zinc in an amount of about 15 mg, copper in an amount of about 2.0 mg, magnesium in an amount of about 5 mg, and omega 3 fatty acids comprising DHA in an amount of about 200 mg. In another embodiment, the methods may administer the composition once a day. In another embodiment, the methods may administer the composition twice a day.

In one embodiment of the present invention, the methods may comprise administering a kit comprising a first composition comprising one or more vitamins, minerals or nutrients selected from the group consisting of vitamin D, twelve carbon chain fatty acid or twelve carbon chain acylglycerol, iodine, vitamin B1, vitamin B6, vitamin B12, vitamin B2, vitamin B9, vitamin B3, vitamin E, vitamin A, vitamin C, iron, zinc, copper, magnesium and omega 3 fatty acids; and one or more pharmaceutically acceptable carriers; and a second composition comprising one or more vitamins, minerals or nutrients selected from the group consisting of vitamin D, twelve carbon chain fatty acid or twelve carbon chain acylglycerol, iodine, vitamin B1, vitamin B6, vitamin B12, vitamin B2, vitamin B9, vitamin B3, vitamin E, vitamin A, vitamin C, iron, zinc, copper, magnesium and omega 3 fatty acids; and one or more pharmaceutically acceptable carriers; wherein the first composition and the second composition collectively comprise vitamin D, lauric acid, iodine, vitamin B1, vitamin B6, vitamin B12, vitamin B2, vitamin B9, vitamin B3, vitamin E, vitamin A, vitamin C, iron, zinc, copper, magnesium and omega 3 fatty acids, and one or more pharmaceutically acceptable carriers.

In another embodiment of the present invention, the methods may comprise administering a kit comprising a first composition and a second composition collectively comprising vitamin D in an amount of about 500 I.U. to about 1500 I.U., twelve carbon chain fatty acid or twelve carbon chain acylglycerol in an amount of about 30 mg to about 300 mg, iodine in an amount of about 100 μg to about 300 μg, vitamin B1 in an amount of about 0.8 mg to about 2.4 mg, vitamin B6 in an amount of about 1.2 mg to about 3.8 mg, vitamin B12 in an amount of about 6 μg to about 18 μg, vitamin B2 in an amount of about 0.9 mg to about 2.7 mg, vitamin B9 in an amount of about 0.5 mg to about 1.5 mg, vitamin E in an amount of about 5 I.U. to about 15 I.U., vitamin A in an amount of about 550 I.U. to about 1650 I.U., vitamin C in an amount of about 6 mg to about 18 mg, vitamin B3 in an amount of about 7.5 mg to about 22.5 mg, iron in an amount of about 13.5 mg to about 40.5 mg, zinc in an amount of about 7.5 mg to about 22.5 mg, copper in an amount of about 1.0 mg to about 3.0 mg, magnesium in an amount of about 2.5 mg to about 7.5 mg, and omega 3 fatty acids in an amount of about 100 mg to about 300 mg.

In another embodiment of the present invention, the methods may comprise administering a kit comprising a first composition and second composition, collectively comprising vitamin D in an amount of about 1000 I.U., twelve carbon chain fatty acid or twelve carbon chain acylglycerol comprising lauric acid in an amount of about 60 mg, iodine in an amount of about 200 μg, vitamin B1 in an amount of about 1.6 mg, vitamin B6 in an amount of about 2.5 mg, vitamin B12 in an amount of about 12 μg, vitamin B2 in an amount of about 1.8 mg, vitamin B9 in an amount of about 1.0 mg, vitamin E in an amount of about 10 I.U., vitamin A in an amount of about 1100 I.U., vitamin C in an amount of about 12 mg, vitamin B3 in an amount of about 15 mg, iron in an amount of about 27 mg, zinc in an amount of about 15 mg, copper in an amount of about 2.0 mg, magnesium in an amount of about 5 mg, and omega 3 fatty acids comprising DHA in an amount of about 200 mg.

In another embodiment, the methods may comprise administering the kits to a patient. In a specific embodiment, the patients may be a human. In another specific embodiment, the human may be a woman. In another embodiment, the woman may be pregnant, prenatal or breast-feeding. In another embodiment, the methods may comprise administering kits once a day or twice a day. In another specific embodiment, the methods may comprise administering a kit wherein the first composition and the second composition are co-administered to a patient.

In another embodiment, the methods may comprise optimizing the level of lauric acid in a lactating woman by administering compositions and kits to a lactating woman. In another embodiment, the methods may comprise optimizing the level of lauric in a prenatal woman by administering compositions and kits to a lactating woman. In another embodiment, the methods may comprise optimizing the level of vitamin D in a prenatal woman by administering the administering compositions and kits to a prenatal woman. In a specific embodiment, the methods may comprise administering compositions that include or kits that collectively include: vitamin D in an amount of about 500 I.U. to about 1500 I.U., twelve carbon chain fatty acid or twelve carbon chain acylglycerols in an amount of about 30 mg to about 300 mg, iodine in an amount of about 100 µg to about 300 µg, vitamin B1 in an amount of about 0.8 mg to about 2.4 mg, vitamin B6 in an amount of about 1.2 mg to about 3.8 mg, vitamin B12 in an amount of about 6 µg to about 18 µg, vitamin B2 in an amount of about 0.9 mg to about 2.7 mg, vitamin B9 an amount of about 0.5 mg to about 1.5 mg, vitamin E in an amount of about 5 I.U. to about 15 I.U., vitamin A in an amount of about 550 I.U. to about 1650 I.U., vitamin C in an amount of about 6 mg to about 18 mg, vitamin B3 in an amount of about 7.5 mg to about 22.5 mg, iron in an amount of about 13.5 mg to about 40.5 mg, zinc in an amount of about 7.5 mg to about 22.5 mg, copper in an amount of about 1.0 mg to about 3.0 mg, magnesium in an amount of about 2.5 mg to about 7.5 mg, and omega 3 fatty acids in an amount of about 100 mg to about 300 mg. In another specific embodiment, the methods may comprise administering compositions that include or kits that collectively include: vitamin D in an amount of about 1000 I.U., twelve carbon chain fatty acid or twelve carbon chain acylglycerol comprising lauric acid in an amount of about 60 mg, iodine in an amount of about 200 µg, vitamin B1 in an amount of about 1.6 mg, vitamin B6 in an amount of about 2.5 mg, vitamin B12 in an amount of about 12 µg, vitamin B2 in an amount of about 1.8 mg, vitamin B9 in an amount of about 1.0 mg, vitamin E in an amount of about 10 I.U., vitamin A in an amount of about 1100 I.U., vitamin C in an amount of about 12 mg, vitamin B3 in an amount of about 15 mg, iron in an amount of about 27 mg, zinc in an amount of about 15 mg, copper in an amount of about 2.0 mg, magnesium in an amount of about 5 mg, and omega 3 fatty acids comprising DHA in an amount of about 200 mg.

DETAILED DESCRIPTION OF THE INVENTION

It is understood that the present invention is not limited to the particular methodologies, protocols, fillers, and excipients, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a vitamin" is a reference to one or more vitamins and includes equivalents thereof known to those skilled in the art and so forth.

Unless defined otherwise, all technical and scientific terms used herein have the same meanings as commonly understood by one of ordinary skill in the art to which this invention belongs. Specific methods, devices, and materials are described, although any methods and materials similar or equivalent to those described herein can be used in the practice or testing of the present invention. All references cited herein are incorporated by reference herein in their entirety.

The term "disease state" as used herein, may comprise any state in which one or more organs or components of an organism malfunction. The term "disease state" may refer to any deterioration of any component of a patient's body and specifically a human patient's body. The term "disease state" may refer to any deficiency of any compound necessary for the maintenance or function of any component of any organism. The term "disease state" may refer to any condition in which a body contains toxins, produced by microorganisms that infect the body or by body cells through faulty metabolism or absorbed from an external source. "Disease states" may be adverse states caused by any diet, any virus, fungi or any bacteria. "Disease states" may comprise disorders associated with pregnant females such as, for example, osteomalacia and preeclampsia and disorders associated with a fetus such as, for example, neural tube defects and various fetal abnormalities. "Disease states" may comprise any pulmonary disorder such as, for example, bronchitis, bronchiectasis, atelectasis, pneunomia, diseases caused by inorganic dusts, diseases caused by organic dusts, any pulmonary fibrosis, and pleurisy. "Disease states" may comprise any hematological/oncological disorder such as, for example, anemia, hemophilia, leukemia, and lymphoma. A "disease state" may comprise any cancer such as, for example, breast cancer, lung cancer, prostate cancer, pancreatic cancer, liver cancer, stomach cancer, testicular cancer, ovarian cancer, skin cancer, cancer of the brain, cancer of the mouth, cancer of the throat, and cancer of the neck. "Disease states" may comprise any disorder of the immune system such as, for example, acquired immune deficiency syndrome (AIDS), AIDS-related complex, infection by any strain of any human immunodeficiency virus (HIV), and other viruses or pathogens such as bacteria, fungi and parasites. A "disease state" may comprise any cardiovascular disorder such as, for example, arterial hypertension, orthostatic hypotension, arteriosclerosis, coronary artery disease, cardiomyopathy, any arrhythmia, any valvular heart disease, endocarditis, pericardial disease, any cardiac tumor, any aneurysm, and any peripheral vascular disorder. "Disease states" may comprise any hepatic/biliary disorder such as, for example, jaundice, hepatic steatosis, fibrosis, cirrhosis, hepatitis, any hepatic granuloma, any liver tumor, cholelithiasis, cholecystitis, and choledocholithiasis. A "disease state" may include a viral infection such as from HIV, herpes virus (HSV-1 and HSV-2), the virus that causes vesicular stomatitis (VSV), measles virus, herpes viridae, human lymprotropic visusess, vesicular stomatitis virus, visna virus, cytomegalovirus, Epstein-Barr virus, influenza virus, pneumonovirus, Sarcoma virus, Syncitial virus and Rubeola virus. A "disease state" may include a fungal infection such as from *Candida albicans* and *Giardia lamblia*. A "disease state" may include a bacterial infection such as from *Staphylococcus, Corynebacerium, Bacillus, Listeria* and *Streptococcus* bacteria, and include species such as *Staphylococcus aureus, bacillus anthracis, Helicobacter pylori* and, *Listeria monocytogenes*, and *Streptococus agalactiae*.

The term "patient," as used herein, comprises any and all organisms and includes the term "subject." "Patient" may refer to a human or any other animal. "Patient" may also refer to a fetus.

The phrase "co-administration" refers to administration of two or more compositions to a patient together, which includes administration at about the same time or within a certain specific or desired time.

The phrase "chewable form" refers to any relatively soft compositions that are chewed in the mouth after oral administration, may have a pleasant taste and mouthfeel, and may quickly break into smaller pieces and may begin to dissolve after chewing such that they can be swallowed substantially as a solution.

The phrase "dissolvable form" refers to any compositions that dissolve into a solution in the mouth. Such compositions, in one embodiment, may dissolve within about 60 seconds or less after placement in the mouth without any chewing.

The term "mouthfeel" refers to non-taste-related aspects of the pleasantness experienced by a person while chewing or swallowing a nutritional supplement. Aspects of mouthfeel include, for example and without limitation, the hardness and brittleness of a composition, whether the composition is chewy, gritty, oily, creamy, watery, sticky, easily dissolved, astringent, effervescent, and the like, and the size, shape, and form of the composition (tablet, powder, gel, etc.).

The phrase "pharmaceutically acceptable," as used herein, refers to those compounds, materials, compositions and/or dosage forms which are, within the scope of sound pharmaceutical/medical judgment, suitable for use in contact with the tissues of human beings and animals without excessive toxicity, irritation, allergic response, or other problem or complication, commensurate with a reasonable benefit/risk ratio. Thus, the phrase "pharmaceutically acceptable carriers," as used herein, refers to such suitable compounds and materials defined above that may be added to the dosage form to assist in satisfactory processing of the dosage form or provide desirable physical characteristics to the dosage form. For example, "pharmaceutically acceptable carriers" may include, but is not limited to, binders, diluents, lubricants, glidants, colorants, emulsifiers, disintegrants, starches, water, oils, alcohols, preservatives, and sugars. In another example, "pharmaceutically acceptable carriers" refers to dosage forms such as capsules, caplets, gel-caps used with, for example, the compositions of the present invention comprising or consisting of omega-3 fatty acids such as docosahexaenoic acid (DHA). Thus, "pharmaceutically acceptable carriers" in gel-caps may be in for example, liquid or oil form, and may include a filler or other appropriate liquid vehicle and may be used with omega-3 fatty acids such as docosahexaenoic acid (DHA) and their equivalents.

The phrase "swallowable form" refers to any compositions that typically do not or are not configured to readily dissolve when placed in the mouth and may be swallowed whole, preferably without any, or with minimal, chewing or discomfort. Such compositions, in one embodiment, may have a shape containing no sharp edges and a smooth, uniform and substantially bubble free outer coating.

The term "dosage form," as used herein, is the form in which the dose is to be administered to the subject or patient. The drug or supplement is generally administered as part of a formulation that includes nonmedical agents. The dosage form has unique physical and pharmaceutical characteristics. Dosage forms, for example, may be solid, liquid or gaseous. "Dosage forms," may include for example, a capsule, tablet, caplet, gel caplet (gelcap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form may be a gelcap.

The term "substantially free of added" as used herein, means free from therapeutically effective amounts of compounds when administered in suggested doses, but may include trace amounts of compounds in non-therapeutically effective amounts. For example, a composition of the present invention that included an inactive ingredient that is a salt or compound including a mineral would still be substantially free of added minerals. For example, trace amounts of titanium dioxide may be provided. Titanium dioxide which is an effective opacifier in powder form, where it is employed as a pigment to provide whiteness and opacity to numerous pharmaceutical products.

As used herein, the terms "inactive," "inert," "excipient," and/or "formulatory" refer to any compound that is an inactive ingredient of a described composition. The definition of "inactive ingredient" as used herein follows that of the U.S. Food and Drug Administration, as defined in 21 C.F.R. 201.3 (b)(8), which is any component of a drug product other than the active ingredient.

By "active ingredient," then, includes any compound intended to furnish pharmacological activity or other direct effect in the diagnosis, cure, mitigation, treatment and/or prevention of disease or a condition. See 21 C.F.R. 210.3(b) (7). Further, "active ingredients" include those compounds of the composition that may undergo chemical change during the manufacture of the composition and be present in the final composition in a modified form intended to furnish an activity or effect. Id. These include the vitamins, minerals and nutrients of the compositions and kits of the present invention.

The term "administrable" defines a composition that is able to be given to a patient Likewise, "administering" refers to the act of giving a composition to a patient or otherwise making such composition available to a patient or the patient taking a composition.

As used herein, the term "about," when located before a dosage amount or dosage range of a specific ingredient, refers to an amount or range closely above and/or closely below the stated amount or range that does not manifestly alter the therapeutic effect of the specific ingredient from the stated amount or range and is meant to encompass at least all equivalents of that amount.

The term "prenatal" supplementation includes optimizing specific nutrients before, during, and after the physiological processes of pregnancy and lactation, which can have profound, positive, and comprehensive impacts on the overall wellness of the developing and newborn child as well as on the safety and health of the mother.

Proper nutrition is essential for maintaining health and preventing diseases. Adequate nutrition is especially critical during, for example, nutritionally volatile or physiologically stressful periods such as those including, by way of example and without limitation, pregnancy, lactation, or any disease state. Vitamin and mineral needs are almost universally increased throughout these periods. Increased needs during physiologically stressful states such as pregnancy, lactation or disease state may result from elevated metabolic demand, increased plasma volume, increased quantities of circulating red blood cells, decreased concentrations of nutrients, and decreased concentrations of nutrient-binding proteins such as, for example and without limitation, serum-ferritin, maltose-binding protein, calmodulin, tocopheryl binding protein, riboflavin binding protein, retinol binding protein, transthyretin, high density lipoprotein-apolipoprotein A1, folic acid binding protein, and 25-hydroxyvitamin D binding protein. Lapido, 72 (Supp.) AMER. J. CLIN. NUTR. 280S-90S (2000). Optimizing specific nutrients before, during, and after the physiological processes of pregnancy and lactation can have profound, positive, and comprehensive impacts on the overall wellness of the developing and newborn child as well as on the safety and health of the mother. Black, 85 (Supp.) BRIT. J. NUTR. S193-97 (2001); Scholl et al., 146 AMER. J. EPIDEM. 134-41 (1997). Nutrients provided to a mother reach the fetus. Specifically, it is established that substrates for growth and development, for example, circulate within the same pathways that carry drugs to and waste products from the fetus. Exchanges of material between mother and fetus occur primarily in the placenta, where villi containing fetal capillaries protrude into sinuses (intervillous spaces). Maternal arterial blood spurts into these spaces, then drains into maternal uterine veins to be returned to the maternal systemic circulation. Solutes in maternal blood cross the epithelial cells and connective tissue of the villi and the endothelium of the fetal capillaries; these solutes are then carried to the fetus by placental veins, which converge into the umbilical vein. THE MERCK MANUAL OF DIAGNOSIS AND THERAPY, (Mark H. Beers, M. D. et al., 18th ed. 2006). The, compositions, kits and methods of the present invention may thus provide the means to optimize good health by utilizing vitamin, mineral, and nutritional supplementation. The compositions, kits and methods of the present invention may be administered to or directed to a subject such as a human or any other organism.

The compositions, kits and methods of the present invention may include vitamin A. Vitamin A is involved in physiological processes that result in cellular differentiation, cellular maturity, and cellular specificity. Thus, vitamin A is an important component of a nutritional supplement for subjects in physiologically stressful states, such as those caused by pregnancy, lactation or disease state. Zile et al., 131(3) J. NUTR. 705-08 (2001). Care should be taken, however, to avoid excess. Indeed, supplemental vitamin A ingestion during pregnancy has been shown in some studies to be teratogenic or deforming to human and animal embryos. G B Mulder et al., 62(4) TERATOLOGY 214-26 (2000). In one embodiment of the present invention, vitamin A may be in a form that is a precursor (pro-vitamin) or metabolite of vitamin A that provides similar nutritional value as vitamin A. For example, the pro-vitamin A carotenoid, may be beta carotene. Beta carotene is converted to other forms of vitamin A, specifically retinol, within the body as needed, thereby avoiding the risk of retinol toxicity. Mayne, FASEB J 10:690-701 (1996). In a specific embodiment, vitamin A may be in one or more of the forms of retinol acetate (also known as retinyl acetate or vitamin A acetate), retinol (vitamin A alcohol), retinol palmitate (also known as retinyl palmitate or vitamin A palmitate), retinoic acid (tretinoin), retinal, beta-cryptoxanthin, alpha-carotene, beta-carotene, gamma-carotene, and provitamin A carotenoids.

In a specific embodiment, vitamin A may be in the form of beta carotene as beta carotene also has powerful anti-oxidant properties. Antioxidants are important during physiologically stressful events for numerous reasons. For example, lipid peroxidation has been associated with over 200 disease processes. Rock et al., 96(7) J. AMER. DIET. ASSOC. 693-702 (1996). Antioxidants are especially important during pregnancy because in the first trimester, establishment of blood flow into the intervillous space is associated with a burst of oxidative stress. The inability to mount an effective antioxidant defense against this burst results in early pregnancy loss. Myatt & Cui, 122, HISTOCHEM. CELL BIOL., 369-82 (2004). Further, oxidative stress has been implicated in the pathophysiology of preeclampsia, a toxemia of pregnancy. Llurba et al., 37(4) FREE RADIC. BIOL. MED. 557-70 (2004). Finally, oxidative stress during pregnancy plays an important role in fetal growth, and healthy antioxidant levels are positively correlated with birth weight and length. Myatt & Cui; Lee et al., 58 EUR. J. CLIN. NUTR., 481-87 (2004).

In a specific embodiment of the compositions, kits and methods of the present invention, vitamin A may be included in amounts ranging from about 550 IU to about 1650 IU. In another specific embodiment, vitamin A may be included in amounts ranging from about 880 IU to about 1320 IU. In another specific embodiment, vitamin A may be included in amounts ranging from about 990 IU to about 1210 IU. In another embodiment, vitamin A may be included in an amount of about 1100 IU.

In another specific embodiment, vitamin A may be included in specific ranges or amounts for each specific form. When provided in their specific forms, the provided numerical range or amount includes the amounts of the specific form and/or compounds that are equivalent to the specific form. For example, vitamin A may be in the form of beta carotene and may be included in the amount of about 1100 IU. Accordingly, in this example, "beta carotene in the amount of about 1100 IU" would include 1000 IU of beta carotene and/or its equivalents and would, for example, include a product having 1100 IU retinol acetate instead of beta carotene.

In another specific embodiment of the compositions, kits and methods of the present invention, vitamin A in the form of beta carotene may be included in amounts ranging from about 550 IU to about 1650 IU. In another specific embodiment, vitamin A in the form of beta carotene may be included in amounts ranging from about 880 IU to about 1320 IU. In another specific embodiment, vitamin A in the form of beta carotene may be included in amounts ranging from about 990 IU to about 1210 IU. In another embodiment, vitamin A in the form of beta carotene may be included in an amount of about 1100 IU. In another specific embodiment of the compositions, kits and methods of the present invention, vitamin A may be included in the form of beta carotene and one or more forms of vitamin A. In a specific embodiment, the compositions, kits and methods of the present invention may include beta carotene and retinol. In another embodiment, the compositions, kits and methods of the present invention may include beta carotene and retinol acetate.

In another embodiment, vitamin A may be present in an amount determined by a measure of mass, as opposed to International Units. One International Unit (IU) of vitamin A is defined as the biological equivalent of about 0.6 µg of beta carotene, or about 0.3 µg of retinol. See REMINGTON, THE SCIENCE AND PRACTICE OF PHARMACY, page 1804($20^{th}$ ed 2000). Accordingly, 550 IU to about 1650 IU is the biological equivalent of about 330 µg to about 990 µg. In another example, about 880 IU to about 1320 IU is the biological equivalent of about 528 µg to about 792 µg. In another example, about 990 IU to about 1210 IU is the biological equivalent of about 594 µg to about 726 µg. In another example, 1100 IU is the biological equivalent of about 660 µg.

The compositions, kits and methods of the present invention may comprise or use one or more B-complex vitamins. This class of vitamins comprises water-soluble nutrients generally not stored in the body. They play roles in a variety of biological processes critical to the health of pregnant women, lactating women, and fetuses such as, for example, the metabolism of homocysteine. The B-complex vitamins that may be included in the compositions, kits and methods of the present invention comprise one or more of vitamin B1, vitamin B2, vitamin B3, vitamin B6, vitamin B9 and vitamin B12.

The compositions, kits and methods of the present invention may comprise or use vitamin B1. Vitamin B1 plays a role in carbohydrate metabolism and neural function. It is a coenzyme for the oxidative decarboxylation of alpha-ketoacids (e.g., alpha-ketoglutarate and pyruvate) and for transketolase, which is a component of the pentose phosphate pathway. NATIONAL RESEARCH COUNCIL, RECOMMENDED DIETARY ALLOWANCES, page 125 (10th ed. 1989) (hereinafter "RDA"). In another specific embodiment, vitamin B1 may be in one or more of the forms of thiamine, thiamine monophosphate, thiamine diphosphate, thiamine triphosphate, acetiamine, allithiamine, prosultiamine and S-acyl derivatives of thiamine such as benfotiamine, fursultiamine and salts and esters thereof.

In another specific embodiment, vitamin B1 may be included in amounts ranging from about 0.8 mg to about 2.4 mg. In another specific embodiment, vitamin B1 may be included in amounts ranging from about 1.3 mg to about 1.9 mg. In another specific embodiment, vitamin B1 may be included in amounts ranging from about 1.4 mg to about 1.75 mg. In another embodiment, vitamin B1 may be included in an amount of about 1.6 mg.

In another specific embodiment, vitamin B1 may be included in specific ranges or amounts for each specific form. When provided in their specific forms, the provided numerical range or amount includes the amounts of the specific form and/or compounds that are equivalent to the specific form. For example, vitamin B1 may be in the form of thiamine mononitrate and may be included in the amount of about 1.6 mg. Accordingly, in this example, "thiamine mononitrate in the amount of about 1.6 mg" would include 1.6 mg of thiamine mononitrate and/or its equivalents and would, for example, include a product having 1.6 mg allithiamine instead of thiamine mononitrate.

The compositions, kits and methods of the present invention may comprise or use vitamin B2. Vitamin B2 is a component of two flavin coenzymes, flavin mononucleotide (FMN) and flavin adenine dinucleotide (FAD). These flavoenzymes are involved in a number of oxidation-reduction reactions including the conversion of pyridoxine and niacin. RDA, supra at 132. Flavoenzymes also play a role in a number of metabolic pathways such as amino acid deamination, purine degradation and fatty acid oxidation and thus help to maintain carbohydrate, amino acid and lipid metabolism.

In a specific embodiment, vitamin B2 may be in one or more of the forms of flavin mononucleotide (FMN), flavin adenine dinucleotide (FAD), riboflavin (also known as 7,8-dimethyl-10-((2R,3R,4S)-2,3,4,5-tetrahydroxypentyl)benzo[g]pteridine-2,4(3H,10H)-dione or lactoflavin) and riboflavin derivatives such as riboflavin-5'-monophosphate, riboflavin-5'-monobutyrate and riboflavin-5'-monopalmitate. In a specific embodiment of the present invention, vitamin B2 may be included in the form of riboflavin.

In another specific embodiment, vitamin B2 may be included in amounts ranging from about 0.9 mg to about 2.7 mg. In another specific embodiment, vitamin B2 may be included in amounts ranging from about 1.5 mg to about 2.2 mg. In another specific embodiment, vitamin B2 may be included in amounts ranging from about 1.6 mg to about 2 mg. In another embodiment, vitamin B2 may be included in an amount of about 1.8 mg.

In another specific embodiment, vitamin B2 in the form of riboflavin may be included in amounts ranging from about 0.9 mg to about 2.7 mg. In another specific embodiment, vitamin B2 in the form of riboflavin may be included in amounts ranging from about 1.5 mg to about 2.2 mg. In another specific embodiment, vitamin B2 in the form of riboflavin may be included in amounts ranging from about 1.6 mg to about 2 mg. In another specific embodiment, vitamin B2 in the form of riboflavin may be included in an amount of about 1.8 mg.

In another specific embodiment, vitamin B2 may be included in specific ranges or amounts for each specific form. When provided in their specific forms, the provided numerical range or amount includes the amounts of the specific form and/or compounds that are equivalent to the specific form. For example, vitamin B2 may be in the form of riboflavin and may be included in the amount of about 1.8 mg. Accordingly, in this example, "riboflavin in the amount of about 1.8 mg" would include 1.8 mg of riboflavin and/or its equivalents and would, for example, include a product having 1.8 mg flavin mononucleotide instead of riboflavin.

The compositions, kits and methods of the present invention may comprise or use vitamin B3. Vitamin B3, or "niacin" is the common name for two compounds: nicotinic acid (also called niacin) and niacinamide (also called nicotinamide). Vitamin B3 is particularly important for maintaining healthy levels and types of fatty acids. It is also required for the synthesis of pyroxidine, riboflavin, and folic acid. RDA, supra at 137. Administration of vitamin B3 also may effect a reduction in total cholesterol (LDL) and very low density lipoprotein (VLDL) levels and an increase in high density lipoprotein (HDL) cholesterol levels. Nicotinamide adenine dinucleotide (NAD) and NAD phosphate (NADP) are active coenzymes of niacin. These coenzymes are involved in numerous enzymatic reactions such as glycolysis, fatty acid metabolism, and steroid synthesis. Henkin et al., 91 AM. J. MED. 239-46 (1991). In a specific embodiment, vitamin B3 may in the forms of niacin (nicotinic acid or pyridine-3-carboxylic acid), and nicotinamide (niacinamide) and salts and esters thereof. In a specific embodiment of the present invention, vitamin B3 may be included in the form of nicotinamide. In another specific embodiment, the present invention may include an equivalent molar amount of niacin.

In another specific embodiment, vitamin B3 may be included in amounts ranging from about 7.5 mg to about 22.5 mg. In another specific embodiment, vitamin B3 may be included in amounts ranging from about 12 mg to about 18 mg. In another specific embodiment, vitamin B3 may be included in amounts ranging from about 13.5 mg to about 16.5 mg. In another embodiment, vitamin B3 may be included in an amount of about 15 mg.

In another specific embodiment, vitamin B3 may be included in specific ranges or amounts for each specific form. When provided in their specific forms, the provided numerical range or amount includes the amounts of the specific form and/or compounds that are equivalent to the specific form. For example, vitamin B3 may be in the form of nicotinamide and may be included in the amount of about 15 mg. Accordingly, in this example, "nicotinamide in the amount of about 15 mg" would include 15 mg of nicotinamide and/or its equivalents and would, for example, include a product having 15 mg niacin instead of nicotinamide.

In another specific embodiment, vitamin B3 in the form of nicotinamide may be included in amounts ranging from about 7.5 mg to about 22.5 mg. In another specific embodiment, vitamin B3 in the form of nicotinamide may be included in amounts ranging from about 12 mg to about 18 mg. In another specific embodiment, vitamin B3 in the form of nicotinamide may be included in amounts ranging from about 13.5 mg to about 16.5 mg. In another embodiment, vitamin B3 in the form of nicotinamide may be included in an amount of about 15 mg.

The compositions, kits and methods of the present invention may comprise or use vitamin B6. The administration of vitamin B6 may reduce the levels of homocysteine. Bostom et al., 49 KIDNEY INT. 147-52 (1996). The active forms of vitamin B6, pyridoxal-5'-phosphate (PLP) and pyridoxamine-5'-phosphate, are coenzymes for numerous enzymes and as such, are important for gluconeogenesis, niacin formation, and erythrocyte metabolism. RDA, supra at 142-43. Vitamin B6 is a coenzyme for both cystathionine synthase and cystathionase, enzymes that catalyze the formation of cysteine from methionine. Homocysteine is an intermediate in this process and elevated levels of plasma homocysteine are recognized as a risk factor for both vascular disease (Robinson et al., 94 CIRCULATION 2743-48 (1996)) and neural tube defects (Locksmith & Duff, 91 OBSTET. GYNECOL. 1027-34 (1998)). In a specific embodiment of the present invention, vitamin B6 may be included in the forms of pyridoxine, 3-hydroxy-4,5-bis(hydroxymethyl)-2-methylpyridine, 5'-deoxypyridoxal, 2-demethylpyridoxal(2-norpyridoxal), 2-propyl-2-norpyridoxal (2'-ethylpyridoxal), 6-methylpyridoxal, 2'-hydroxypyridoxal (2-hydroxymethyl-2-demethylpyridoxal or 2-hydroxymethyl-2-norpyridoxal), 4'-deoxypyridoxine 5'-phosphate, 5'-methylpyridoxal-5'-phosphate, pyridoxal N-oxide 5'-phosphate, Pyridoxal, Pyridoxamine, Pyridoxine-5'-phosphate (PNP), pyridoxal-5'-phosphate (PLP) and pyridoxamine-5'-phosphate (PMP), and their salts and chelates thereof. In a specific embodiment of the present invention, vitamin B6 may be included in the form of pyridoxine hydrochloride.

In another specific embodiment, vitamin B6 may be included in specific ranges or amounts for each specific form. When provided in their specific forms, the provided numerical range or amount includes the amounts of the specific form and/or compounds that are equivalent to the specific form. For example, vitamin B6 may be in the form of pyridoxine hydrochloride and may be included in the amount of about 2.5 mg. Accordingly, in this example, "pyridoxine hydrochloride in the amount of about 2.5 mg" would include 2.5 mg of pyridoxine hydrochloride and/or its equivalents and would, for example, include a product having 2.5 mg pyridoxamine instead of pyridoxine hydrochloride.

In another specific embodiment, vitamin B6 may be included in amounts ranging from about 1.2 mg to about 3.8 mg. In another specific embodiment, vitamin B6 may be included in amounts ranging from about 2.0 mg to about 3.0 mg. In another specific embodiment, vitamin B6 may be included in amounts ranging from about 2.25 mg to about 2.75 mg. In another embodiment, vitamin B6 may be included in an amount of about 2.5 mg.

The compositions, kits and methods of the present invention may comprise or use vitamin B9. Vitamin B9 is a generic name of a B-vitamin that includes multiple compounds with a general structure. For example, vitamin B9 encemposses the term folate, which itself is the generic name for many different forms of this water-soluble vitamin (vitamin B9), which is essential for DNA synthesis and, hence, cell division. Simpson et al., THE JOURNAL OF MATERNAL-FETAL AND NEONATAL MEDICINE, *Micronutrients and women of reproductive potential: required dietary intake and consequences of dietary deficiency or excess. Part I—Folate, Vitamin B12, Vitamin B6*, Epub 1-21, (2010). Indeed, folate encompasess numerous compounds that for example, are based on a pteridine ring, an aminobenzoic acid and one or more glutamic acidresidues. Id. Folic acid (pteroglutamic acid or PGA) is a synthetic form of folate, and the first folate synthesised and used as a supplement. Id. The term folates may also be used in the generic sense to designate any members of the family of pteroylglutamates, or mixtures of them, having various levels of reduction of the pteridine ring, one-carbon substitutions and numbers of glutamate residues. PURE & APPL. CHEM., *IUPAC-IUB Commission on Biochemical Nomenclature (CBN). Nomenclature and Symbols for Folic Acid and Related Compounds*. Arch 59, No. 6: 833-836 (1987).

Vitamin B9, however, is not only defined by its structure, but also by its various functions. Indeed, vitamin B9 is essential for DNA synthesis and, hence, cell division and is required metabolically as a coenzyme in one-carbon transfer reactions. Simpson, supra. This vitamin has demonstrated the ability to prevent neural tube defects such as spina bifida caused by disturbed homocysteine metabolism. Vanderput et al., EXP. BIOL. MED. 243-70 (2001); DeFalco et al., 27 CLIN. EXP. OBSTET. GYNECOL. 188-90 (2000); Eskes, 27 CLIN. EXP. OBSTET. GYNECOL. 157-67 (2000); Locksmith & Duff, supra. Folic acid, a commonly used term synonymous with vitamin B9, is known to reduce the risk of multiple diseases. Clinical trials definitively demonstrated the effectiveness of folic acid supplementation in reducing the number of neural tube defects. Simpson et al., THE JOURNAL OF MATERNAL-FETAL AND NEONATAL MEDICINE, *Micronutrients and women of reproductive potential: required dietary intake and consequences of dietary deficiency or excess. Part I—Folate, Vitamin B12, Vitamin B6*, Epub 1-21, (2010). Indeed, folic acid supplementation in reducing the risk of neural tube defects and other congenital malformations is generally accepted. Pietrzik et al., CLIN PHARMACOKINET 49 (8): 535-548 (2010). Furthermore, evidence is accumulating to support a possible role of folic acid in the reduction in risk of other diseases, including dementia and certain types of cancer. Id. Lastly, folate or folate derivative thereof that increase blood folate levels, thereby reducing homocysteine levels, which is a common way to measure vitamin B9 effectiveness. Id.

Thus, In a specific embodiment of the present invention, vitamin B9 may include numerous forms. In a specific embodiment, vitamin B9 may be included in the form of folic acid. In another embodiment, vitamin B9 may be included one or more of the forms of folic acid, folacin, metafolin, folate and/or one or more natural isomers of folate including (6S)-tetrahydrofolic acid or a polyglutamyl derivative thereof, 5-methyl-(6S)-tetrahydrofolic acid or a polyglutamyl derivative thereof, 5-formyl-(6S)-tetrahydrofolic acid or a polyglutamyl derivative thereof, 10-formyl-(6R)-tetrahydrofolic acid or a polyglutamyl derivative thereof, 5,10-methylene-(6R)-tetrahydrofolic acid or a polyglutamyl derivative thereof, 5,10-methenyl-(6R)-tetrahydrofolic acid or a polyglutamyl derivative thereof and 5-formimino-(6S)-tetrahydrofolic acid or a polyglutamyl derivative thereof and the salts and esters thereof. In another embodiment, vitamin B9 may be in the form of a folate or folate derivative thereof that is eventually converted to 5-methyl-tetrahydrofolic acid in the body and/or is absorbed into the bloodstream as 5-methyl-tetrahydrofolic acid. Folates, such as folic acid and folate, are eventually absorbed in the body and converted to L-5-methyl-tetrahydrofolic acid In another embodiment, vitamin B9 may be in the form of a folate or folate derivative thereof that increases blood folate levels, thereby reducing homocysteine levels.

In another embodiment, vitamin B9 may be in the form of folate or reduced folates with various salts. In a specific embodiment, the folate and reduced folate are selected from the group consisting of D-glucosamine-folate, D-galactosamine-folate, D-glucosamine (6R,S)-tetrahydrofolate, D-glucosamine (6S)-tetrahydrofolate, D-glucosamine (6R)-tetrahydrofolate; D-galactosamine (6R,S)-tetrahydrofolate, D-galactosamine (6S)-tetrahydrofolate, D-galactosamine (6R)-tetrahydrofolate; D-glucosamine 5-methyl-(6R,S)-tetrahydrofolate, D-glucosamine 5-methyl-(6S)-tetrahydrofolate, D-glucosamine 5-methyl-(6R)-tetrahydrofolate; D-galactosamine 5-methyl-(6R,S)-tetrahydrofolate, D-galactosamine 5-methyl-(6S)-tetrahydrofolate, and D-galactosamine 5-methyl-(6R)-tetrahydrofolate.

In another specific embodiment, vitamin B9 may be included in amounts ranging from about 0.5 mg to about 1.5 mg. In another specific embodiment, vitamin B9 may be included in amounts ranging from about 0.8 mg to about 1.2 mg. In another specific embodiment, vitamin B9 may be included in amounts ranging from about 0.9 mg to about 1.1 mg. In another embodiment, vitamin B9 may be included in an amount of about 1.0 mg.

In another specific embodiment, vitamin B9 may be included in specific ranges or amounts for each specific form. When provided in their specific forms, the provided numerical range or amount includes the amounts of the specific form and/or compounds that are equivalent to the specific form. For example, vitamin B9 may be in the form folic acid and may be included in the amount of about 1.0 mg. Accordingly, in this example, "folic acid in the amount of about 1.0 mg" would include 1.0 mg of folic acid and/or its equivalents and would, for example, include a product having 1.0 mg 5-methyl-(6S)-tetrahydrofolic acid instead of folic acid.

In a specific embodiment, vitamin B9 may be in the form of folic acid. In another specific embodiment, vitamin B9 in the form of folic acid may be included in amounts ranging from about 0.5 mg to about 1.5 mg. In another specific embodiment, vitamin B9 in the form of folic acid may be included in amounts ranging from about 0.8 mg to about 1.2 mg. In another specific embodiment, vitamin B9 in the form of folic acid may be included in amounts ranging from about 0.9 mg to about 1.1 mg. In another embodiment, vitamin B9 in the form of folic acid may be included in an amount of about 1.0 mg.

The compositions, kits and methods of the present invention may comprise or use vitamin B12. Vitamin B12 can be converted to the active coenzymes, methylcobalamin and 5'-deoxyadenosylcobalamin. These coenzymes are necessary for folic acid metabolism, conversion of coenzyme A and myelin synthesis. Methylcobalamin also catalyzes the demethylation of a folate cofactor which is involved in DNA synthesis. A lack of demethylation may result in folic acid deficiency. RDA, supra at 159-160. Deoxyadenosylcobalamin is the coenzyme for the conversion of methylmalonyl-CoA to succinyl-CoA, which plays a role in the citric acid cycle. Cobalamin, along with pyridoxine and folic acid, also are implicated in the proper metabolism of homocysteine, a breakdown product of the amino acid methionine, which is correlated with an increased risk of heart disease due to its negative effects on endothelial function. In a specific embodiment of the present invention, vitamin B12 may be in one or more of the forms of cobalamin, methylcobalamin, 5'-deoxyadenosylcobalamin (adenosylcobalamin or cobamamide), cyanocobalamin, hydroxycobalamin and mecobalamin.

In another specific embodiment, vitamin B12 may be included in amounts ranging from about 6 µg to about 18 µg. In another specific embodiment, vitamin B12 may be included in amounts ranging from about 9.6 µg to about 14.4 µg. In another specific embodiment, vitamin B12 may be included in amounts ranging from about 10.8 µg to about 13.2 µg. In another embodiment, vitamin B12 may be included in an amount of about 12 µg.

In another specific embodiment, vitamin B12 may be included in specific ranges or amounts for each specific form. When provided in their specific forms, the provided numerical range or amount includes the amounts of the specific form and/or compounds that are equivalent to the specific form. For example, vitamin B12 may be in the form cyanocobalamin and may be included in the amount of about 12 µg. Accordingly, in this example, "cyanocobalamin in the amount of about 12 µg" would include 12 µg of cyanocobalamin and/or its equivalents and would, for example, include a product having 12 µg methylcobalamin instead of cyanocobalamin.

The compositions, kits and methods of the present invention may comprise or use vitamin C. The major biochemical role of water-soluble vitamin C is as a co-substrate in metal catalyzed hydroxylations. Like beta carotene, vitamin C has antioxidant properties. It interacts directly with superoxide hydroxyl radicals and singlet oxygen, and also provides antioxidant protection for folate and vitamin E, keeping vitamin E in its most potent form. Vitamin C may afford protective effects against preeclampsia by participating in the scavenging of free radicals. Indeed, significantly lower levels of vitamin C have been observed in preeclamptic women than in controls. Woods et al., 185(1) AM. J. OBSTET. GYNECOL. 5-10 (2001); Kharb, 1 EURO. J. OBSTET. GYNECOL. REPROD. BIOL. 37-39 (2000); Milczarek et al., 210 MOL. CELL BIOCHEM. 65-73 (2000). Vitamin C also enhances the absorption of iron. RDA, supra at 115. In addition, vitamin C is required for collagen synthesis, epinephrine synthesis, and bile acid formation. Moreover, vitamin C has been implicated in inhibiting atherosclerosis by being present in extracellular fluid of the arterial wall and potentiating nitric oxide activity, thus normalizing vascular function. In a specific embodiment of the present invention, vitamin C may be included in the forms of ascorbic acid, ascorbates (calcium or sodium ascorbate), dehydroascorbic acid and salts, ascorbyl palmitate, ascorbyl phosphates and salts (such as sodium or magnesium ascorbyl phosphate), ascorbyl tetraisopalmitate, tetrahexyldecyl ascorbate, ascorbyl sulfates and salts, acylated ascorbic acid derivatives (such as 6-O-acyl-2-O-alpha-D-glucopyranosyl-L-ascorbic acids), 6-bromo-6-deoxy-L-ascorbic acid, and ascorbate salts. In a specific embodiment, vitamin C may be included in the form of ascorbic acid.

In another specific embodiment, vitamin C may be included in amounts ranging from about 6 mg to about 18 mg. In another specific embodiment, vitamin C may be included in amounts ranging from about 9.6 mg to about 14.4 mg. In another specific embodiment, vitamin C may be included in amounts ranging from about 10.8 mg to about 13.2 mg. In another embodiment, vitamin C may be included in an amount of about 12 mg.

In another specific embodiment, vitamin C may be included in specific ranges or amounts for each specific form. When provided in their specific forms, the provided numerical range or amount includes the amounts of the specific form and/or compounds that are equivalent to the specific form. For example, vitamin C may be in the form ascorbic acid and may be included in the amount of about 12 mg. Accordingly, in this example, "ascorbic acid in the amount of about 12 mg" would include 12 mg of ascorbic acid and/or its equivalents and would, for example, include a product having 12 mg ascorbyl palmitate instead of ascorbic acid.

In another specific embodiment, vitamin C in the form of ascorbic acid may be included in amounts ranging from about 6 mg to about 18 mg. In another specific embodiment, vitamin C in the form of ascorbic acid may be included in amounts ranging from about 9.6 mg to about 14.4 mg. In another specific embodiment, vitamin C in the form of ascorbic acid may be included in amounts ranging from about 10.8 mg to about 13.2 mg. In another embodiment, vitamin C in the form of ascorbic acid may be included in an amount of about 12 mg.

The compositions, kits and methods of the present invention may comprise or use vitamin D. In another embodiment, the compositions and methods of the present invention may include a beneficially increased supplementation of vitamin D. Vitamin D is a fat-soluble "hormone like" substance important for the maintenance of healthy bones. This vitamin increases the absorption of calcium and phosphorous from the gastrointestinal tract, and improves mineral resorption into bone tissue. The result of this physiological function is a correlation between adequate systemic levels in pregnancy and a long-lasting reduction in osteoporotic fractures throughout the lifespan of the newborn. M F Holick, "Vitamin D," in MODERN NUTRITION IN HEALTH AND DISEASE, p. 313, M E Shils, J A Olsen and M. Shikeeds., Plea and Febiger, Philadelphia, Pa. (1994); M K Javaid et al., LANCET 367(9504): 36-43 (2006).

Moreover, recent research suggests that vitamin D has more positive physiological effects than previous thought. Bischoff-Ferrari H A, 624 ADV EXP MED BIOL. 55-71 (2008); Holick M F, 357 N. ENG. J. MED. 266-81, (2007); Parikin et al., 89(3) J CLIN ENDOCRINOL METAB. 1196-99 (2004). For example, it has recently been determined that vitamin D also has a role in the enhancement of vascular function, defense against cancer, immuno-competence, blood pressure regulation and possessing the ability to enhance cellular insulin sensitivity in the human body. Due to the additional roles that vitamin D plays in the human body, it has recently been determined that higher daily vitamin D intake beyond current recommendations may be associated with better health outcomes. Bischoff-Ferrari H A, supra. Indeed, studies suggest increasing the serum level of 25-hydroxyvitamin D, a beneficial derivative of vitamin D, to a 30 ng/ml serum range. Id. A 30 ng/ml appears to be the most advantageous serum levels in recent studies reviewing patient bone mineral density (BMD), lower extremity function, dental health, risk of falls, admission to nursing home, fractures, cancer prevention and incident hypertension. Id.

Further, studies suggest that an intake of about 1000 IU of vitamin D3 (cholecalciferol) per day for all adults may bring at least 50% of the population up to the 30 ng/ml serum range for 25-hydroxyvitamin D. Id. Current nutritional supplements, however, do not provide a high enough dosage for obtaining such a high serum level of 25-hydroxyvitamin D. Presently, the suggested daily amount of vitamin D, as stated by the U.S. Dietary Reference Intake for adequate intake (AI) of vitamin D for infants, children and men and women aged 19-50 is 200 IU/day. Adequate intake increases to 400 IU/day for men and women aged 51-70 and up to 600 IU/day past the age of 70. Id. Due to these studies, present nutritional supplements may be insufficient to remedy the current U.S. and global epidemic related to vitamin D deficiency.

Indeed, research findings indicate vitamin D status during pregnancy is more important than previous thought. Vitamin D's role continues to expand in for example, infant immunity, neurodevelopment, birth weight, and incidence of asthma. Growing research findings regarding the importance of this hormone-like compound is due, in large part, to the fact that vitamin D receptors have now been identified on nearly every tissue and cell in the human body. H F DeLuca et al., FASEB J 15:2579-2585 (2001); D. Eyles et al., NEUROSCIENCE 118(3):641-653 (2003); C A Mannion et al., CMAJ 174(9): 1273-1277 (2006); B W Hollis et al., CMAJ 174(9):1287-1290 (2006); American Academy of Allergy, Asthma and Immunology Annual Meeting, Miami, Fla. (March 2006). A nutritional supplement that includes a higher dosage amount of vitamin D, as compared to present nutritional supplements and, specifically, prenatal supplements, is therefore currently needed. Thus, one embodiment of the present invention includes compositions, kits and methods that provide a beneficial increased supplementation of vitamin D, specifically, for example prenatal, pregnant or breast feeding women.

The vitamin D of the compositions and methods of the present invention may comprise vitamin D. In a specific embodiment of the present invention, vitamin D may be in one or more the forms of vitamin D3 (also known as calciol or cholecalciferol or colecalciferol), vitamin D2 (also known as calciferol, ergocalciol, ergocalciferol, ercalciol, Deltalin or Viosterol), previtamin D2, ergosterol, calcitriol (also known as 1,25-dihydroxycholecalciferol), 7-dehydrocholesterol, vitamin D1, vitamin D4 (also known as 22-dihydroergocalciferol, 22,23-dihydroercalciol or (24S)-methylcalciol), vitamin D5 (also known as (24S)-Ethylcalciol or sitocalciferol), 7-dehydrositosterol, Lumisterol, 25-hydroxyvitamin D, all steroids that exhibit the biological activity of calciol, 25-fluorocalciol, (3S)-3-amino-3-deoxycalciol, 11α-acetoxycalciol, calcidiol (also known as 25-hydroxycholecalciferol or calcifediol), ercalcitriol, calcitetrol, tacalciol (also known as tachysterol$_3$), (5E)-isocalciol (also known as isovitamin D3), Dihydroercalciol (also known as dihydrotachysterol3), (1S)-Hydroxycalciol (also known as 1α-hydroxycholecalciferol or alfacaleidol), (24R)-Hydroxycalcidiol (also known as 24(R),25-dihydroxycholecalciferol), Ercalcidiol, Ercalcitriol, Ertacalciol, (5E)-(10S)-10,19-Dihydroercalciol (also known as dihydrotachysterol2), (6Z)-Tacalciol (also known as precalciferol or pre-vitamin D), and (22E)-(24R)-Ethyl-22,23-didehydrocalciol also known as vitamin D6.

In one embodiment of the invention, vitamin D may be present in the amount ranging from about 400 IU to about 1600 IU. In another embodiment, vitamin D may be present in the amount ranging from about 750 IU to about 1250 IU. In another embodiment, vitamin D is present in the amount ranging form about 900 IU to about 1100 IU. In another embodiment, vitamin D is present in the amount of about 1000 IU.

In another specific embodiment, vitamin D may be included in specific ranges or amounts for each specific form. When provided in their specific forms, the provided numerical range or amount includes the amounts of the specific form and/or compounds that are equivalent to the specific form. For example, vitamin D may be in the form vitamin D3 and may be included in the amount of about 1000 IU. Accordingly, in this example, "vitamin D3 in the amount of about 30 mg" would include 1000 IU of vitamin D3 and/or its equivalents and would, for example, include a product having 1000 IU mg vitamin D2 instead of vitamin D3.

In another embodiment of the present invention, the vitamin D of the compositions, kits and methods of the present invention may be vitamin D3. In the body, vitamin D3 is produced when its precursor is exposed to ultraviolet irradiation (e.g., sunlight) and then hydroxylated in the liver to form 25-hydroxyvitamin D3, the major form of vitamin D in the circulation. This form of the vitamin may be hydroxylated again in the kidney, yielding 1,25 hydroxyvitamin D3, the most potent form of vitamin D. As noted above, vitamin D3 plays a role in the maintenance of calcium and phosphorus homeostasis, but it is also active in cell differentiation and immune function.

In one embodiment of the invention, vitamin D in the form of vitamin D3 may be present in the amount ranging from about 400 IU to about 1600 IU. In another embodiment, vitamin D in the form of vitamin D3 may be present in the amount ranging from about 750 IU to about 1250 IU. In another embodiment, vitamin D in the form of vitamin D3 may be present in the amount ranging form about 900 IU to about 1100 IU. In another embodiment, vitamin D in the form of vitamin D3 may be present in the amount of about 1000 IU.

In another embodiment, vitamin D may be present in an amount determined by a measure of mass, as opposed to International Units. One International Unit (IU) of vitamin D is defined as the biological equivalent of about 0.025 µg of vitamin D3. See REMINGTON, THE SCIENCE AND PRACTICE OF PHARMACY, page 1800 (20$^{th}$ ed 2000) (hereinafter, "Remington"). Accordingly, 400 IU to about 1600 IU is the biological equivalent of about 10 µg to about 40 µg. In another example, about 750 IU to about 1250 IU is the biological equivalent of about 18.75 µg to about 31.25 µg. In another example, about 900 IU to about 1100 IU is the biological equivalent of about 22.5 µg to about 27.5 µg. In another example, 1000 IU is the biological equivalent of about 25 µg.

The compositions, kits and methods of the present invention may comprise or use vitamin E. Vitamin E is a fat-soluble vitamin antioxidant found in biological membranes where it protects the phospholipid membrane from oxidative stress. Vitamin E inhibits the oxidation of unsaturated fatty acids by trapping peroxyl free radicals. It is also an antiatherogenic agent, and studies have demonstrated a reduced risk of coronary heart disease with increased intake of vitamin E. Stampfer et al., 328 NEW ENG. J. MED. 1444-49 (1993). In addition, vitamin E, like beta carotene and vitamin C, may afford protective effects against preeclampsia by participating in the scavenging of free radicals. As with vitamin C, significantly lower levels of vitamin E have been observed in preeclamptic women than in controls. Woods et al., AM J OBSIET GYNECOL, 185(1):5-10 (2001); Kharb, EURO. J. OBSIET GYNECOL REPROD BIOL, 1:37-39 (2000); Milczarek et al., MOL CELL BIOCHEM, 210:65-73 (2000). In a specific embodiment of the present invention, vitamin E may be included in one or more of the forms of alpha, beta, gamma, and delta tocopherols in its natural or synthetic (dl) forms; alpha, beta, gamma, and delta tocotrienols in its natural or synthetic (dl) forms, dl-alpha tocopheryl derivatives such as dl-alpha tocopheryl esters, dl-alpha-tocopheryl acetate or succinate and d-alpha-tocopheryl acetate or dl-alpha tocopheryl phosphates (such as Ester-E®). In a specific embodiment of the present invention, vitamin E may be included in the form of d-alpha-tocopheryl acetate. In another specific embodiment, vitamin E may be included in the form of an equivalent molar amount of d-alpha tocopheryl succinate.

In another specific embodiment, vitamin E may be included in amounts ranging from about 5 IU to about 15 IU. In another specific embodiment, vitamin E may be included in amounts ranging from about 8 IU to about 12 IU. In another specific embodiment, vitamin E may be included in amounts ranging from about 9 IU to about 11 IU. In another embodiment, vitamin E may be included in an amount of about 10 IU.

In another specific embodiment, vitamin E may be included in specific ranges or amounts for each specific form. When provided in their specific forms, the provided numerical range or amount includes the amounts of the specific form and/or compounds that are equivalent to the specific form. For example, vitamin E may be in the form d-alpha-tocopheryl acetate and may be included in the amount of about 10 IU. Accordingly, in this example, "d-alpha-tocopheryl in the amount of about 10 IU" would include 10 IU of d-alpha-tocopheryl and/or its equivalents and would, for example, include a product having 10 IU alpha-tocotrienol instead of d-alpha-tocopheryl.

The compositions, kits and methods of the present invention may comprise or use iron. A primary function of iron is to carry oxygen to bodily tissues via the hemoglobin part of red blood cells. Supplemental intake of iron is critical to preventing anemia, a disorder associated with a variety of physiological states including, for example, pregnancy. Bothwell, 72(Supp.) AM. J. CLIN. NUTR. 257S-64S (2000). Severe anemia may have adverse effects upon a mother and a fetus. Specifically, significant depression of hemoglobin has been associated with poor pregnancy outcome. Black, supra; Sifakis & Pharmakides, 900 ANN. N.Y. ACAD. SCI. 125-36 (2000). The, compositions, kits and methods of the present invention may include iron in one or more of the forms of elemental iron, in the form of a salt, chelated form, non-chelated form, chelated to an amino acid, carbonyl iron, ferrous gluconate, ferrous fumarate, polysaccharide iron complex, elemental polysaccharide iron, polysaccharide iron, ferrous (II)-bis-glycinate chelate, ferrous asparto glycinate, ferrous bisglycinate, ferrous bisglycinate hydrochloride, ferrous bisglycinate, elemental ferrous bisglycinate, ferrous sulfate, ferronyl (micronized), as Iron Aid, iron protein succinylate, carbonyl iron, Sumalate iron, Heme iron complex, as Ferrochel amino acid chelate, heme iron polypeptide as Proferrin-bovine source, as heme iron polypeptide (bovine source) as sodium iron EDTA (Ferrazone), ferric ammonium citrate, elemental iron, and ferric pyrophosphate.

In a specific embodiment of the present invention, iron may be included in the form of polysaccharide iron complex. In another specific embodiment, iron may be included in the form of an equivalent molar amount of ferrous fumarate. In another specific embodiment, iron may be included in amounts ranging from about 13.5 mg to about 40.5 mg. In another specific embodiment, iron may be included in amounts ranging from about 21.6 mg to about 32.4 mg. In another specific embodiment, iron may be included in amounts ranging from about 24.3 mg to about 29.7 mg. In another embodiment, iron may be included in an amount of about 27 mg.

In another specific embodiment, iron may be included in specific ranges or amounts for each specific form. When provided in their specific forms, the provided numerical range or amount includes the amounts of the specific form and/or compounds that are equivalent to the specific form. For example, iron may be in the form polysaccharide iron complex and may be included in the amount of about 27 mg. Accordingly, in this example, "polysaccharide iron complex in the amount of about 27 mg" would include 27 mg of polysaccharide iron complex and/or its equivalents and would, for example, include a product having 27 mg ferrous fumarate instead of polysaccharide iron complex.

The compositions, kits and methods of the present invention may comprise or use iodine. Iodine provides nutritional benefits as it is an essential component of the thyroid hormones that are involved in the regulation of various enzymes and metabolic processes, such as thyroxine and triiodothyronine. Thyroid hormones play pivotal roles in metabolism. Consequences of deficiency (hypothyroidism) and excess (hyperthyroidism) are well-recognised clinically. Simpson et al., THE JOURNAL OF MATERNAL-FETAL AND NEONATAL MEDICINE, *Micronutrients and women of reproductive potential: required dietary intake and consequences of dietary deficienty or excess. Part II—Vitamin D, Vitamin A, Iron, Zinc, Iodine, Essential Fatty Acids,* 1-2, epub online 2010. Indeed, iodine deficiency disorders (IDD) include mental retardation, hypothyroidism, goiter, cretinism, and varying degrees of other growth and developmental abnormalities which can be a result from inadequate thyroid hormone production from lack of sufficient iodine. Further, iodine is an important element in breast milk for infant nutrition. An adequate concentration of iodine in breast milk is essential to provide for optimal neonatal thyroid hormone stores and to prevent impaired neurological development in breast-fed neonates. In many countries of the world, low iodine content of the breast milk indicates less than optimum maternal and infant iodine nutrition. F. Azizi et al., CLIN ENDOCRINOL;70(5):803-9 (2009). Iodine deficiency, is a major public health problem in nearly all countries, particularly for women during pregnancy and lactation. The National Health and Nutrition Examination survey data also found 14.9% of women aged 15-44 years and 6.9% of pregnant women to have urinary iodine concentrations of only 50 mg/L, indicating iodine intake of less than 100 mg daily. Simpson, supra. The American Thyroid Association thus also recommends that women receive 150 mg iodine supplements daily during pregnancy and during lactation, which is often the upper limit for iodine dosing amounts in prenatal supplments. Id. Regardless of such recommendations, iodine nutrition and supplementation is lacking. For example, in Europe, most women are iodine deficient during pregnancy, with less than 50% receiving iodine supplementation; of 40 countries, only nine met the requirements of iodised salt at the household level to be at least 90% of the DR1. Id. Iodine nutrition of women of childbearing age thus remains inadequate and an area worthy of public health concern. Id. A nutritional supplement that includes a higher dosage amount of iodine, as compared to present nutritional supplements and, specifically, prenatal supplements, is therefore currently needed. Thus, one embodiment of the present invention includes compositions, kits and methods that provide a beneficial increased supplementation of iodine, specifically, for example prenatal, pregnant or breast feeding women.

In a specific embodiment, iodine may be in the forms of elemental iodine, iodized salt, Lugol's iodine, sodium iodide, potassium iodide, potassium iodate, nascent iodine, and Nano-Colloidal Detoxified Iodine. In another specific embodiment, iodine may be present in the amounts ranging from about 100 µg to about 300 µg. In another embodiment, iodine may be present in the amounts ranging from about 160 µg to about 240 µg. In another embodiment, iodine may be present in the amounts ranging from about 180 µg to about 220 µg. In another embodiment, iodine may be present in the amount of about 200 µg.

In another specific embodiment, iodine may be included in specific ranges or amounts for each specific form. When provided in their specific forms, the provided numerical range or amount includes the amounts of the specific form and/or compounds that are equivalent to the specific form. For example, iodine may be in the form potassium iodide and may be included in the amount of about 200 µg. Accordingly, in this example, "potassium iodide in the amount of about 200 µg" would include 200 µg of potassium iodide and/or its equivalents and would, for example, include a product having 200 µg Nano-Colloidal Detoxified Iodine instead of potassium iodide.

The compositions, kits and methods of the present invention may comprise or use magnesium. Magnesium is found primarily in both bone and muscle and is important for over 300 different enzyme reactions. A primary function of magnesium is to bind to phosphate groups in adenosine triphosphate (ATP), thereby forming a complex that assists in the transfer of ATP phosphate. Magnesium also functions within cells as a membrane stabilizer. Magnesium plays roles in nucleic acid synthesis, glycolysis, transcription of DNA and RNA, amino acid activation, membrane transport, transketolase reactions, and protein synthesis. James L. L. Groff et al., ADVANCED NUTRITION AND HUMAN METABOLISM 341 (2d ed. 1996). It is also involved in the formation of cAMP, a cytosolic second messenger that plays a role in cell signaling mechanisms. Magnesium also functions both synergistically and antagonistically with calcium in neuromuscular transmission. RDA, supra at 188. Specifically, magnesium is critical for the maintenance of electrochemical potentials of nerve and muscle membranes and the neuromuscular junction transmissions, particularly important in the heart. Not surprisingly, magnesium deficiency is tied to cardiovascular disease and hypertension. Agus et al., 17 CRIT. CARE CLIN. 175-87 (2001). Indeed, oral magnesium therapy improves endothelial function in patients with coronary disease. Shechter et al., 102 CIRCULATION 2353-58 (2000).

Magnesium is available in a variety of salts and can be included in the compositions, kits and methods of the present invention in either chelated or nonchelated form. In one specific embodiment of the present invention, magnesium may be included in the forms of elemental magnesium, in the form of a salt, in a chelated form, in a non-chelated form, magnesium acetate, magnesium carbonate, magnesium gluconate, magnesium chloride, magnesium citrate, magnesium silicate, magnesium stearate, magnesium sulfate, magnesium oxide, and magnesium chelated to an amino acid (magnesium glycinate, magnesium aspartate).

In another specific embodiment, magnesium may be present in the amounts ranging from about 2.5 mg to about 7.5 mg. In another embodiment, magnesium may be present in the amounts ranging from about 4 mg to about 6 mg. In another embodiment, magnesium may be present in the amounts ranging from about 4.5 mg to about 5.5 mg. In another embodiment, magnesium may be present in the amount of about 5 mg.

In another specific embodiment, magnesium may be included in specific ranges or amounts for each specific form. When provided in their specific forms, the provided numerical range or amount includes the amounts of the specific form and/or compounds that are equivalent to the specific form. For example, magnesium may be in the form magnesium oxide and may be included in the amount of about 5 mg. Accordingly, in this example, "magnesium oxide in the amount of about 5 mg" would include 5 mg of magnesium oxide and/or its equivalents and would, for example, include a product having 5 mg magnesium stearate instead of magnesium oxide.

The compositions, kits and methods of the present invention may comprise or use zinc. Zinc plays a role in numerous metabolic activities such as nucleic acid production, protein synthesis, and development of the immune system. There are more than 200 zinc metalloenzymes including aldolase, alcohol dehydrogenase, RNA polymerase, and protein kinase C. Zima et al., 17 BLOOD PURIF. 182-86 (1999). Zinc stabilizes RNA and DNA structures, forms zinc fingers in nuclear receptors, and is a component of chromatin proteins involved in transcription and replication. Deficiencies of zinc during pregnancy have been shown to contribute to severe fetal abnormalities. Srinivas et al., 68(6) INDIAN J. PEDIATR. 519-22 (2001); Yang et al., 13(4) BIOMED. ENVIRON. SCI. 280-86 (2000); King, 71(Supp.) AM. J. CLIN. NUTR. 1334S-43S (2000). Indeed, the recommended daily allowance for zinc increases during pregnancy. A higher dose of zinc, however, is associated with causing nausea in some patients. Thus, for pregnant women or other patients that are more susceptible to nausea, a conservative amount of zinc that still provides adequate nutritional supplementation is desirable. Zinc is available in many forms and may be included in the kits and methods of the present invention in chelated or nonchelated form.

In a specific embodiment of the present invention, zinc may be provided in one or more of the forms of elemental zinc, in the form of a salt, in a chelated form, in a non-chelated form, zinc acetate, zinc gluconate, zinc picolinate, zinc sulfate and zinc oxide. In a specific embodiment of the present invention, zinc may be included in the form of zinc oxide. In another specific embodiment, zinc may be included in amounts ranging from about 7.5 mg to about 22.5 mg. In another specific embodiment, zinc may be included in amounts ranging from about 12 mg to about 18 mg. In another specific embodiment, zinc may be included in amounts ranging from about 13.5 mg to about 16.5 mg. In another embodiment, zinc may be included in an amount of about 15 mg.

In another specific embodiment, zinc may be included in specific ranges or amounts for each specific form. When provided in their specific forms, the provided numerical range or amount includes the amounts of the specific form and/or compounds that are equivalent to the specific form. For example, zinc may be in the form zinc oxide and may be included in the amount of about 15 mg. Accordingly, in this example, "zinc oxide in the amount of about 15 mg" would include 15 mg of zinc oxide and/or its equivalents and would, for example, include a product having 15 mg zinc sulfate instead of zinc oxide.

The compositions, kits and methods of the present invention may comprise or use copper. Copper is an important component of the process of gene expression. Additionally, one of copper's most vital roles is to help form hemoglobin, which, as previously discussed, carries oxygen to tissues via its iron component. In this respect copper plays a key role in protecting against anemia. Further, deficiencies of copper may lead to neutropenia and bone abnormalities in pregnant and lactating women. Uauy et al., AMER J CLIN NUTR 67:952 S-959S (Supp.) (1998). In addition, a fetus must accumulate copper at a rate of 50 mcg×kg−1×d−1 over the latter half of pregnancy; any deficiency in accumulation may lead to low birth weight and protein-energy malnutrition. Id. Many forms of copper are known to those skilled in the art, including copper oxide (Reade Advanced Materials, Providence, R.I.). In a specific embodiment, copper may be included in the forms of a salt, in a chelated form, in a non-chelated form, cupric oxide, copper sulfate, copper gluconate, copper citrate, cupric acetate, alkaline copper carbonate, and copper salicylate.

In another specific embodiment, copper may be included in amounts ranging from about 1.0 mg to about 3.0 mg. In another specific embodiment, copper may be included in amounts ranging from about 1.6 mg to about 2.4 mg. In another specific embodiment, copper may be included in amounts ranging from about 1.8 mg to about 2.2 mg. In another embodiment, copper may be included in an amount of about 2.0 mg.

In another specific embodiment, copper may be included in specific ranges or amounts for each specific form. When provided in their specific forms, the provided numerical range or amount includes the amounts of the specific form and/or compounds that are equivalent to the specific form. For example, copper may be in the form copper oxide and may be included in the amount of about 2.0 mg. Accordingly, in this example, "copper oxide in the amount of about 2.0 mg" would include 2.0 mg of copper oxide and/or its equivalents and would, for example, include a product having 2.0 mg copper sulfate instead of copper oxide.

The compositions, kits and methods of the present invention may comprise or use omega-3 fatty acids. Omega-3 fatty acids play integral roles in physiological mechanisms that serve to prevent, treat and/or alleviate the occurrence or negative effects of some diseases and has shown multiple health-promoting properties in adults. For example, omega-3 fatty acids are linked to health benefits such as preventing the occurrence of cancer, preventing the occurrence of heart disease, and are helpful in brain health and immune function. Indeed, omega-3 fatty acids include essential fatty acids linked to numerous health benefits, such as docahexaenoic acid (or docosahexaenoic acid, DHA), eicosapentaenoic acid (EPA) and α-linolenic acid (ALA). In another specific embodiment, the compositions, kits and methods of the present invention may comprise or use Docahexaenoic acid (or docosahexaenoic acid, DHA). In another specific embodiment, the compositions, kits and methods of the present invention may comprise or use eicosapentaenoic acid (EPA). In another specific embodiment, the compositions, kits and methods of the present invention may comprise or use α-linolenic acid (ALA).

The omega-3 fatty acid DHA, a major component of fish oil, has been shown to be of particular importance, especially during pregnancy or for lowering blood pressure. Indeed, studies suggest that DHA, but not EPA, reduce ambulatory blood pressure and heart rate in hyperlipidemic men. TA Mori et al., HYPERTENSION. 34:253-260 (1999). The results of this study thus suggest that DHA is the principal fatty acid in fish and fish oils that is responsible for blood pressure and heart rate effects in humans. Id.

Further, DHA is vital for optimal fetal and infant brain/cognitive development, as well as for normal brain function throughout life. F M Rioux, O. Hernell et al., ACTA PAEDIATR 95(2):137-144 (2006). The sleep patterns of infants born to mothers with higher plasma phospholipid DHA suggest greater central nerve system maturity. S R Cheruku, C J Lammi-Keefe et al., AM J CLIN NUTR 76:608-613, 2002. Additionally, children with Attention Deficit Hyperactivity Disorder (ADHD) have been shown to have abnormal levels of DHA. EA Mitchell, M. Manku et al., CLIN PEDIATR 26:406-411 (1986); L J Stevens, J R Burgess et al., PHYSIOL BEHAV 59:915-920 (1996). Studies have indicated a correlation between maternal DHA intake and intelligence quotient in the child. The direct correlation between brain development and systemic DHA status is secondary to the fact that DHA is taken up by the brain in preference to other fatty acids. Adequate DHA levels in pregnancy have also been correlated with optimizing the length of gestation and decreasing the risk of neurodevelopmental psychopathology. These critical findings have prompted the National Institute of Health (NIH) to recommend that pregnant women consume at least 300 mg of omega-3 fatty acids during pregnancy. N. Neurenger et al., NUTR REV 44:285-294 (1986); G. Hornstra et al., AM J CLIN NUTR 71:285 S-291S (2000); I B Helland et al., PEDIATRICS 111:E39-E44 (2003); F. Facchinetti et al., EUR REV MED PHARMACOL SCI 9(1):41-48 (2005); R K McNamara et al., PROSTAGLANDINS LEUKOT ESSENT FATTY ACIDS (29 Aug. 2006).

DHA is also important for the development of the infant retina and improving the visual acuity of the infant. C A Francois, W E Connor et al., AM J CLIN NUTR 77:226-233 (2003). Preterm infants have a more rapid development of visual acuity if fed human milk or formula enriched with DHA, compared to standard formula. M H Jorgensen, K F Michaelsen et al., LIPIDS 31(1):99-105 (1996). An increase in visual acuity has also been observed to develop more rapidly in term infants breast-fed from mothers whose diets are supplemented with DHA. Id.

In addition to the aforementioned benefit of DHA to the developing child, this essential fatty acid has also shown multiple health-promoting properties in adults. These include anti-thrombotic, anti-inflammatory and anti-atherosclerotic activity, all of which reduce the risk of heart disease. M Laidlaw and B J Holub, AM J CLIN NUTR 77:37-42 (2003). Inverse relationships have also been found between systemic levels of omega-3 fatty acids such as DHA and incidence and severity of mood disorders and depression, including post-partum depression. Therefore, introduction of omega-3 during pregnancy has a double benefit, to both child and mother. FB Hu et al., JAMA 287(14):1815-1821 (2002); C. Von Schacky et al., ANN INTERN MED 130:554-562 (1999); G.

Parker et al., AM J PSYCHIATRY 163(6):969-978 (2006); SJ Otto et al., PROSTAGLANDINS LEUKOT ESSENT FATTY ACIDS 69(3):237-243 (2003).

For women, DHA is particularly useful in counteracting the progression of breast cancer. Human breast cancer cells exposed to DHA exhibit an increase in cell death by apoptosis. B A Stoll, BR J NUTR 87(3):193-198, 2002. DHA also inhibits cyclooxygenase-2, which promotes mammary carcinogenesis. Id. DHA supplementation during pregnancy has also been shown to increase the length of gestation by about six days, helping mothers carry to a healthy full term. C M Smuts et al., OBSTETRICS AND GYNECOLOGY 101(3):469-479 (2003).

Intake of omega-3 fatty acids such as DHA not only leads to their incorporation into cell membrane lipids (B A Stoll, B R J NUTR 87(3):193-198 (2002)), but also storage in adipose tissue and secretion in breast milk. C A Francois, W E Connor et al., AM J CLIN NUTR 77:226-233 (2003). Although the human body can derive a limited amount of DHA from another fatty acid known as alpha-linolenic acid, this process is inefficient for optimal needs. A rich dietary source of direct DHA is fish. Id. However, some lactating women are vegetarians, have limited access to fish or simply do not like fish. A further problem with encouraging increased fish intake in pregnancy is that most species contain methyl mercury (MeHg) in various amounts. MeHg is a potent neurotoxin that can increase the risk of retarded cognitive development. This concern prompted both the United States Environmental Protection Agency (2004) and the Food and Drug Administration (2001) to issue advisories recommending that pregnant women modify their fish consumption. These recommendations have resulted in a reduced intake of fish during pregnancy, thus helping to protect against fetal MeHg related harm. However, this has concurrently reduced maternal intake of DHA. In fact, a recent dietary study of over 100 pregnant or nursing women in the United States showed an astonishingly low intake of DHA on average (60-80 mg/day), and a dangerously low percentage (<2) consumed the aforementioned recommended intake of 300 mg/day of DHA as set forth by the NIH. JT Cohen et al., AM J PREV MED, 29:353-365 (2005); U.S. Department of Health and Human Services, U.S. Environmental Protection Agency, "What you need to know about mercury in fish and shellfish," Report EPA-823-F-04-009 (March 2004); E. Oken et al., OBSTET GYNECOL 102:346-351 (2003).

DHA may be obtained in solid form, such as in a whole-cell microbial product, or in liquid form, such as in an oil. An example of DHA in oil form is DHASCO®-T vegetable oil from micro-algae (Martek Biosciences Corporation, Columbia, Md.). In a specific composition, the DHA is DHAgold®, life's DHA™ (DHASCO®), any Algae Oil, Krill Oil and/or vegetarian DHA.

In a specific embodiment of the present invention, the source of DHA may be from one or more of animal, fish, plants, algae or microorganism production.

In another embodiment, the compositions, kits and methods of the present invention may include DHA derived from algae. DHA derived from algae, as opposed to being derived from fish oil, has numerous beneficial effects. First, the DHA from algae does not have the "fishy" smell that can come with DHA from fish oil. Indeed, high doses of DHA from fish oil may result in the patient having an unappealing after taste or a slight "fishy" body odor or "fishy" odor on the patient's breath. Second, DHA derived from algae can be more easily regulated to assure consistency and further remove the risk of added chemicals or other dangers. For example, DHA from algae would not have the risk of being tainted with mercury as opposed to DHA from fish oil. Thus, DHA from algae provides pregnant women and neonate with DHA without this risk and dangers of mercury. In a specific embodiment, the source of DHA may be from algae oil. In another specific embodiment, the source of algae oil may be one or more of microalgae *Schizochytrium* sp, microalgae *Crypthecodinium cohnii*, microalgae *Ulkenia* sp. SAM2179, microalgae *Schizochytrium linacinum* strain SC-1. In another specific embodiment the source of DHA may be Martek Oil C53-O100.

In another specific embodiment, omega-3 fatty acids may be included in amounts ranging from about 100 mg to about 600 mg. In another specific embodiment, omega-3 fatty acids may be included in amounts ranging from about 100 mg to about 300 mg. In another specific embodiment, omega-3 fatty acids may be included in amounts ranging from about 160 mg to about 240 mg. In another specific embodiment, omega-3 fatty acids may be included in amounts ranging from about 180 mg to about 220 mg. In another embodiment, omega-3 fatty acids may be included in an amount of about 200 mg.

In another specific embodiment, omega-3 fatty acids may be included in specific ranges or amounts for each specific form. When provided in their specific forms, the provided numerical range or amount includes the amounts of the specific form and/or compounds that are equivalent to the specific form. For example, omega-3 fatty acids may bwe in the form of DHA and may be included in the amount of about 200 mg. Accordingly, in this example, "DHA in the amount of about 200 mg" would include 200 mg of DHA and/or its equivalents and would, for example, include a product having 200 mg EPA instead of DHA.

In another specific embodiment, omega-3 fatty acids may be in the form of DHA and may be included in amounts ranging from about 100 mg to about 300 mg. In another specific embodiment, omega-3 fatty acids in the form of DHA may be included in amounts ranging from about 160 mg to about 240 mg. In another specific embodiment, omega-3 fatty acids in the form of DHA may be included in amounts ranging from about 180 mg to about 220 mg. In another embodiment, omega-3 fatty acids in the form of DHA may be included in an amount of about 200 mg.

In another embodiment of the present invention, the compositions, kits and methods may comprise a twelve carbon chain fatty acid or twelve carbon chain acylglycerol. Lauric acid, for example, a saturated twelve carbon chain fatty acid, contains many antibacterial, antiviral, and antifungal properties and thus has an overall anti-infectious benefit. Lieberman et al., ALTERNATIVE & COMPLEMENTARY THERAPIES, 310-314 (December, 2006). Lauroleic acid is an example of an unsaturated twelve carbon fatty acid which may also provide similar benefits, and has been described as a natural metabolite of lauric acid in rat hepatocytes and may be present in milk. Legrand et al., LIPIDS 37, 569 (2002). Acylglycerols, which contain one to three fatty acid chains covalently bonded to a glycerol by an ester bond can be precursors or metabolites of fatty acids may also provide multiple antimicrobial properties. For example, monolaurin, a metabolite of lauric acid, possesses antibacterial, antiviral, and antifungal properties, with apparently greater activity than lauric acid. Lieberman et al., ALTERNATIVE & COMPLEMENTARY THERAPIES, 310-314 (December, 2006). In a specific example, the antibacterial activity of medium chain fatty acids and their acylglycerols were studied for antibacterial activity, where it was determined that that the monoacylglycerols were more active than their fatty acids, with monolaurin being the most active Batovska et al., POL. J. MICROBIOL. *Antibacterial study of the medium chain*

*fatty acids and their 1-monoglycerides: individual effects and synergistic relationships,* 58(1): 43-47 (2009).

In addition, a diet that includes twelve carbon chain fatty acids or twelve carbon chain acylglycerols such as lauric acid and monolaurin translates into more of these compounds in mothers milk and thus may provide the overall anti-infectious benefits to an infant. Francois et al., AM J CLIN NUTR, 67(2): 301-8 (1998). Even further, there is evidence that a diet of twelve carbon chain fatty acids or twelve carbon chain acylglycerols heavily influences the blood levels; thus these benefits may be provided to the fetus when provided in a pregnant women's diet. dela Paz et al., PHILLIPINE JOURNAL OF INTERNAL MEDICINE, *The Effect of Virgin Coconut Oil on Lipid Profile and Fasting Blood Sugar: A Phase I Clinical Trial,* 48(2); 1-7 (2010).

In a specific embodiment of the present invention, the twelve carbon chain fatty acid or twelve carbon chain acylglycerol may be in the form of lauric acid, glycerol monolaurate (monolaurin), dilaurin, trilaurin, a twelve carbon chain monoacylglycerol, a twelve carbon chain unsaturated fatty acid, a diacylglycerol comprising at least one twelve carbon chain and a triacylglyceral comprising at least one twelve carbon atom chain.

The twelve carbon chain fatty acid may be saturated or unsaturated. For example, a saturated twelve carbon chain fatty acid (i.e., lauric acid) has the following structure:

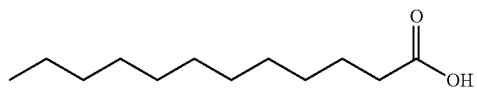

If the twelve carbon chain fatty acid is unsaturated, there may be one or more double bonds on the carbon chain.

Further, the one or more double bonds may be located between the two and the three carbon:

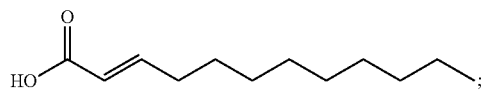

between the three and the four carbon:

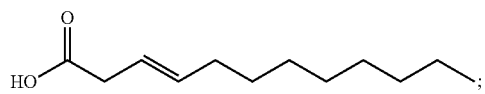

between the four and the five carbon:

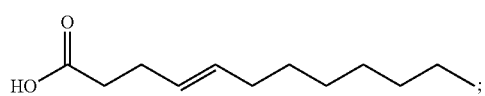

between the five and the six carbon:

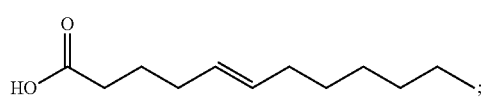

between the six and the seven carbon;

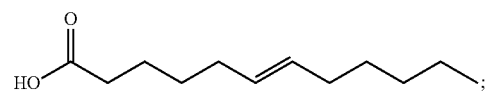

between the seven and the eight carbon:

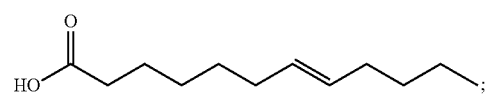

between the eight and the nine carbon:

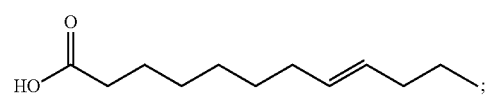

between the nine and the ten carbon:

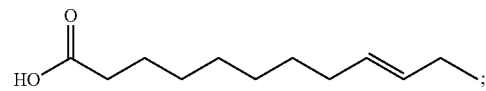

between the ten and the eleven carbon,

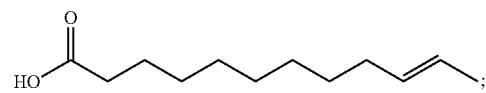

and between the eleven and twelve carbon:

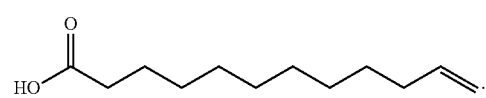

In another embodiment, the double bond carbons may be in either the cis or the trans configuration, or in the Z or the E configuration. The compounds provided direcetly above are all depicted in the trans or Z configuration The unsaturated twelve carbon chain fatty acids may be in the cis or E configuration, for example:

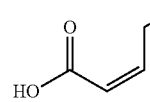

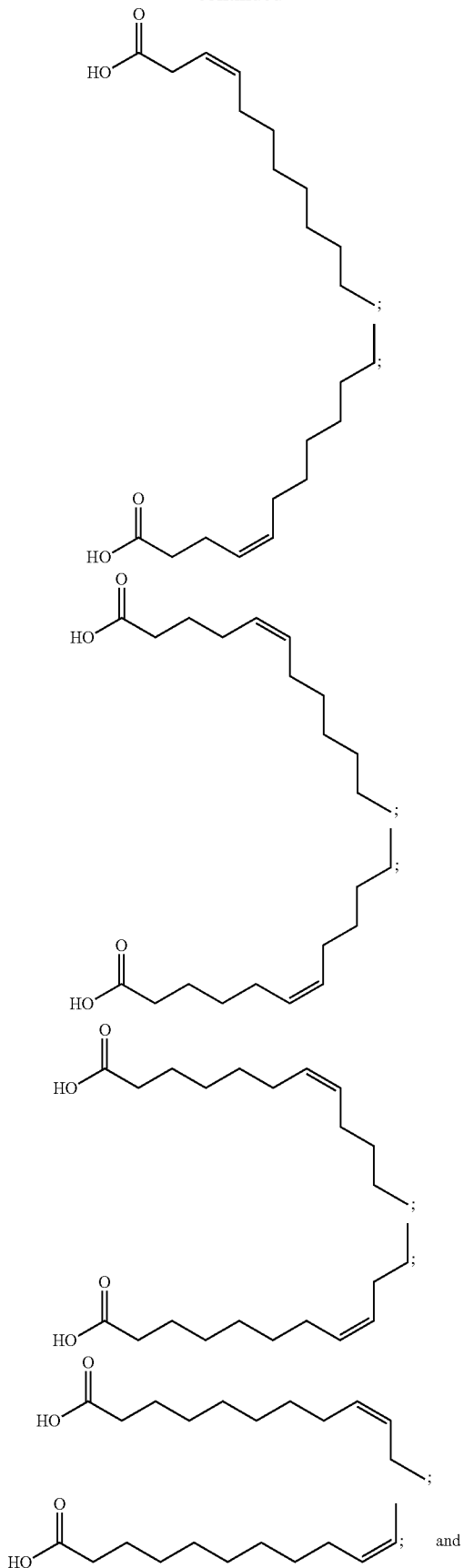

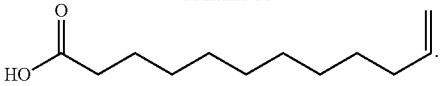

In another example, the twelve carbon chain fatty acid that is unsaturated may be linderic acid. Linderic acid has a double bond between the four and five carbon and has been found as the major fatty acid (47%) in various seed oils Hopkins C Y et al., LIPIDS, 1:118 (1961), In another example, the twelve carbon chain fatty acid that is unsaturated may include lauroleic acid. Lauroleic acid has been described as a natural metabolite of lauric acid in rat hepatocytes, Legrand P et al., LIPIDS 37, 569 (2002), and may be present in milk. In another example, the twelve carbon chain fatty acid may be in any form of 2-dodecenoic acid, 3-dodecenoic acid, 4-dodecenoic acid, 5-dodecenoic acid, 6-dodecenoic acid, 7-dodecenoic acid, 8-dodecenoic acid, 9-dodecenoic acid, 10-dodecenoic acid, and 11-dodecenoic acid, and specifically, these compounds may be in the cis or trans configuration or the E or Z configuration.

In another embodiment of the present invention, the twelve carbon chain acylglycerol may be a twelve carbon chain monoacylglycerol, a diacylglycerol comprising at least one twelve carbon chain and a triacylglycerol comprising at least one twelve carbon atom chain. Possible combinations are depicted below in saturated forms:

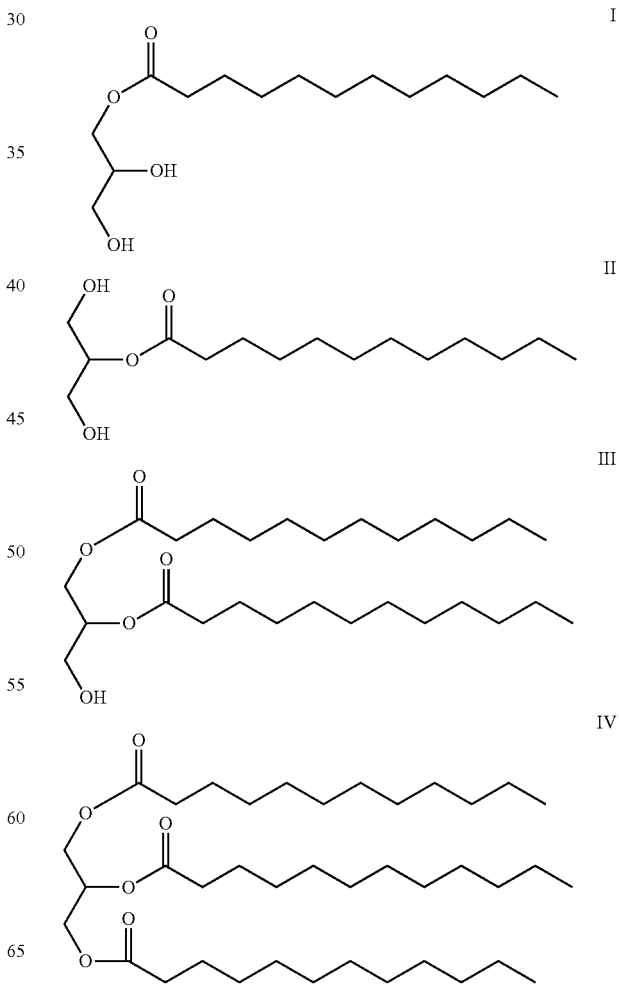

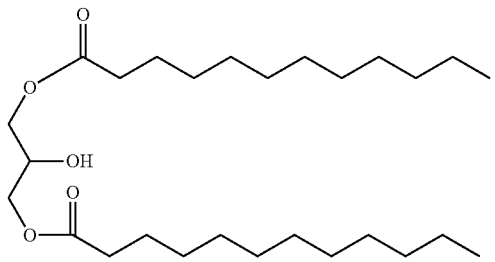

Accordingly, in the specific embodiments, the monoacylglycerol may include the esterified fatty acid on either the 1 carbon of glycerol (compound I) or the 2 carbon of glycerol (compound II). In another specific embodiment, the diacylglycerols may include the esterified fatty acid on the 1 and 2 carbon of glycerol (compound III) or on the 1 and 3 carbon of glycerol (compound V). In a specific embodiment, the monoacylglycerol may be glycerol monolaurate (monolaurin), dilaurin, and trilaurin.

In another embodiment, the acylglycerol may include fatty acids as described above that are esterified with glycerol. The esterified twelve carbon chain fatty acid may be saturated or unsaturated. If the esterified twelve carbon chain fatty acid is unsaturated, there may be one or more double bonds on the carbon chain. Further, the one or more double bonds may be located between the two and the three carbon, between the three and the four carbon, between the four and the five carbon, between the five and the six carbon, between the six and the seven carbon, between the seven and the eight carbon, between the eight and the nine carbon, between the nine and the ten carbon, between the ten and the eleven carbon, and between the eleven and twelve carbon. In another embodiment, the double bond carbons may be in either the cis or the trans configuration, or in the Z or the E configuration. For example, the esterified twelve carbon chain fatty acid that is unsaturated may be linderic acid. In another example, the esterified twelve carbon chain fatty acid that is unsaturated may include lauroleic acid. In another example, the esterified twelve carbon chain fatty acid may be 2-dodecenoic acid, 3-dodecenoic acid, 4-dodecenoic acid, 5-dodecenoic acid, 6-dodecenoic acid, 7-dodecenoic acid, 8-dodecenoic acid, 9-dodecenoic acid, 10-dodecenoic acid, and 11-dodecenoic acid. In a specific embodiment, these compounds may be in the cis or trans formation or the E or Z formation. In another specific embodiment, these fatty acids my esterified on the 1, 2 or 3 carbon of glycerol.

In a specific embodiment, the twelve carbon chain fatty acid or twelve carbon chain acylglycerol may be lauric acid. In another specific embodiment of the present invention, the twelve carbon chain fatty acid or twelve carbon chain acylglycerol, such as lauric acid, is derived from a natural or synthetic source, or derived from a genetically modified or engineered source. In a specific embodiment, the synthetic source is due to chemical modification of a compound to arrive at the twelve carbon chain fatty acid or twelve carbon chain acylglycerol.

In another embodiment, the twelve carbon chain fatty acid or twelve carbon chain acylglycerol may be derived from a genetically modified or engineered source. In a specific embodiment, the twelve carbon chain fatty acid or twelve carbon chain acylglycerol may engineered by introducing a gene donor for the twelve carbon chain fatty acid or twelve carbon chain acylglycerol production into a plant. In one embodiment, the plant may be easy to grow, or easily adapted to extract the twelve carbon chain fatty acid or twelve carbon chain acylglycerol. In a specific embodiment, genes in fatty acid and oil biosynthesis may be cloned. In specific embodiment, these genes may be cloned and introduced into rapeseed. In one embodiment, the twelve carbon chain fatty acid or twelve carbon chain acylglycerol is genetically engineered using rapeseed oil and introducing a gene donor involved in the biosynthesis of the twelve carbon chain fatty acid or twelve carbon chain acylglycerol production. In another embodiment, the California bay laurel tree *Umbellularia californica* may be a gene donor for the twelve carbon chain fatty acid or twelve carbon chain acylglycerol production. In a specific embodiment, the engineered product may be Laurical™. In one specific embodiment, lauric acid and/or monolaurin derived from a genetically modified or engineered source.

In another embodiment of the present invention, the source of the twelve carbon chain fatty acid or twelve carbon chain acylglycerol may be from one or more of the group consisting of algae oil, Martek Algae oil, coconut oil, babassu oil, and palm kernel oil.

In a specific embodiment, the twelve carbon chain fatty acid or twelve carbon chain acylglycerol may be included in amounts ranging from about 30 mg to about 300 mg. In a specific embodiment, the twelve carbon chain fatty acid or twelve carbon chain acylglycerol may be present in an amount of about 60 mg. In a specific embodiment, the source of the twelve carbon chain fatty acid or twelve carbon chain acylglycerol may be coconut oil and algae oil. In another specific embodiment, the source of the twelve carbon chain fatty acid or twelve carbon chain acylglycerol may be coconut oil and algae oil and may be included in amounts ranging from about 30 mg to about 300 mg.

In another specific embodiment, the twelve carbon chain fatty acid or twelve carbon chain acylglycerol may be included in specific ranges or amounts for each specific form. When provided in their specific forms, the provided numerical range or amount includes the amounts of the specific form and/or compounds that are equivalent to the specific form. For example, the twelve carbon chain fatty acid or twelve carbon chain acylglycerol may be in the form lauric acid and may be included in the amount of about 60 mg. Accordingly, in this example, "lauric acid in the amount of about 60 mg" would include 60 mg of lauric acid and/or its equivalents and would, for example, include a product having 60 mg monolaurin instead of lauric acid.

In another specific embodiment, the twelve carbon chain fatty acid or twelve carbon chain acylglycerol may be in the form of lauric acid and is included in amounts ranging from about 30 mg to about 300 mg. In a specific embodiment, the twelve carbon chain fatty acid or twelve carbon chain acylglycerol may be in the form of lauric and is present in an amount of about 60 mg. In a specific embodiment, the source of the twelve carbon chain fatty acid or twelve carbon chain acylglycerol in the form of lauric acid may be coconut oil and/or algae oil and may be included in amounts ranging from a total amount of about 30 mg to about 300 mg.

The compositions, kits and methods of the present invention may include or use a combination of the included vitamins, nutrients and minerals just described. In a specific embodiment, the compositions, kits and methods of the present invention may include a twelve carbon chain fatty acid or twelve carbon chain acylglycerol, vitamin D, iodine, vitamin B1, vitamin B6, vitamin B12, vitamin B2, vitamin B9, vitamin B3, vitamin E, vitamin A, vitamin C, iron, zinc, copper, magnesium, omega 3 fatty acids and one or more pharmaceutically acceptable carriers.

In another embodiment, the vitamins, nutrients and minerals may be included or used in any specific form just described. In a specific embodiment, the twelve carbon chain fatty acid or twelve carbon chain acylglycerol may be lauric acid. In a specific embodiment, the twelve carbon chain fatty acid or twelve carbon chain acylglycerol may be monolaurin. In a specific embodiment, the omega 3 fatty acids may be DHA.

In another embodiment, the compositions, kits and methods of the present invention may include or use a combination of the included vitamins, nutrients and minerals in the ranges or amounts just described.

In a specific embodiment, the compositions, kits and methods of the present invention may include or use vitamin D in an amount of about 500 I.U. to about 1500 I.U., twelve carbon chain fatty acid or twelve carbon chain acylglycerols in an amount of about 30 mg to about 300 mg, iodine in an amount of about 100 μg to about 300 μg, vitamin B1 in an amount of about 0.8 mg to about 2.4 mg, vitamin B6 in an amount of about 1.2 mg to about 3.8 mg, vitamin B12 in an amount of about 6 μg to about 18 μg, vitamin B2 in an amount of about 0.9 mg to about 2.7 mg, vitamin B9 in an amount of about 0.5 mg to about 1.5 mg, vitamin E in an amount of about 5 I.U. to about 15 I.U., vitamin A in an amount of about 550 I.U. to about 1650 I.U., vitamin C in an amount of about 6 mg to about 18 mg, vitamin B3 in an amount of about 7.5 mg to about 22.5 mg, iron in an amount of about 13.5 mg to about 40.5 mg, zinc in an amount of about 7.5 mg to about 22.5 mg, copper in an amount of about 1.0 mg to about 3.0 mg, magnesium in an amount of about 2.5 mg to about 7.5 mg, and omega 3 fatty acids comprising DHA in an amount of about 100 mg to about 300 mg. In a specific embodiment, the composition s, kits and methods of the present invention may include or use vitamin D in an amount of about 1000 I.U., twelve carbon chain fatty acid or twelve carbon chain acylglycerols comprising lauric acid in an amount of about 60 mg, iodine in an amount of about 200 μg, vitamin B1 in an amount of about 1.6 mg, vitamin B6 in an amount of about 2.5 mg, vitamin B12 in an amount of about 12 μg, vitamin B2 in an amount of about 1.8 mg, vitamin B9 in an amount of about 1.0 mg, vitamin E in an amount of about 10 I.U., vitamin A in an amount of about 1100 I.U., vitamin C in an amount of about 12 mg, vitamin B3 in an amount of about 15 mg, iron in an amount of about 27 mg, zinc in an amount of about 15 mg, copper in an amount of about 2.0 mg, magnesium in an amount of about 5 mg, and omega 3 fatty acids comprising DHA in an amount of about 200 mg.

In one embodiment of the present invention, twelve carbon chain fatty acid or twelve carbon chain acylglycerol, vitamin D3, iodine, vitamin B1, vitamin B6, vitamin B12, vitamin B2, vitamin B9, vitamin B3, vitamin E, vitamin A, vitamin C, iron, zinc, copper, magnesium, and omega 3 fatty acids may be provided in one composition. In a specific embodiment, the composition may be in the dosage form of a gelcap. To ensure that all such ingredients may be provided in one gelcap composition, various inactive ingredients and pharmaceutically acceptable carries may be added. In a specific embodiment, a wetting, stabilizing agent may be used for the gelcap composition, In a specific embodiment, the wetting or stabilzing agent is lecithin oil. In another specifice embodiment beeswax may be added. In another specific embodiment, soybean oil may be added.

In another embodiment, the present invention may comprise one or more compositions in a kit. In a specific embodiment, the one or more compositions may include or use a combination of the vitamins, nutrients and minerals just described. In a specific embodiment, the one or more compositions may collectively use or include a twelve carbon chain fatty acid or twelve carbon chain acylglycerol, vitamin D, iodine, vitamin B1, vitamin B6, vitamin B12, vitamin B2, vitamin B9, vitamin B3, vitamin E, vitamin A, vitamin C, iron, zinc, copper, magnesium, omega 3 fatty acids and one or more pharmaceutically acceptable carriers.

In a specific embodiment, the two compositions may collectively use or include a twelve carbon chain fatty acid or twelve carbon chain acylglycerol, vitamin D, iodine, vitamin B1, vitamin B6, vitamin B12, vitamin B2, vitamin B9, vitamin B3, vitamin E, vitamin A, vitamin C, iron, zinc, copper, magnesium, omega 3 fatty acids and one or more pharmaceutically acceptable carriers.

In a specific embodiment, the multiple compositions, kits and methods of the present invention may collectively include or use vitamin D in an amount of about 500 I.U. to about 1500 I.U., twelve carbon chain fatty acid or twelve carbon chain acylglycerols in an amount of about 30 mg to about 300 mg, iodine in an amount of about 100 μg to about 300 μg, vitamin B1 in an amount of about 0.8 mg to about 2.4 mg, vitamin B6 in an amount of about 1.2 mg to about 3.8 mg, vitamin B12 in an amount of about 6 μg to about 18 μg, vitamin B2 in an amount of about 0.9 mg to about 2.7 mg, vitamin B9 in an amount of about 0.5 mg to about 1.5 mg, vitamin E in an amount of about 5 I.U. to about 15 I.U., vitamin A in an amount of about 550 I.U. to about 1650 I.U., vitamin C in an amount of about 6 mg to about 18 mg, vitamin B3 in an amount of about 7.5 mg to about 22.5 mg, iron in an amount of about 13.5 mg to about 40.5 mg, zinc in an amount of about 7.5 mg to about 22.5 mg, copper in an amount of about 1.0 mg to about 3.0 mg, magnesium in an amount of about 2.5 mg to about 7.5 mg, and omega 3 fatty acids comprising DHA in an amount of about 100 mg to about 300 mg.

In a specific embodiment, the multiple compositions, kits and methods of the present invention may collectively include or use vitamin D in an amount of about 1000 I.U., twelve carbon chain fatty acid or twelve carbon chain acylglycerols comprising lauric acid in an amount of about 60 mg, iodine in an amount of about 200 μg, vitamin B1 in an amount of about 1.6 mg, vitamin B6 in an amount of about 2.5 mg, vitamin B12 in an amount of about 12 μg, vitamin B2 in an amount of about 1.8 mg, vitamin B9 in an amount of about 1.0 mg, vitamin E in an amount of about 10 I.U., vitamin A in an amount of about 1100 I.U., vitamin C in an amount of about 12 mg, vitamin B3 in an amount of about 15 mg, iron in an amount of about 27 mg, zinc in an amount of about 15 mg, copper in an amount of about 2.0 mg, magnesium in an amount of about 5 mg, and omega 3 fatty acids comprising DHA in an amount of about 200 mg In a specific embodiment, active ingredients such as twelve carbon chain fatty acid or twelve carbon chain acylglycerols and the vitamins, minerals and nutrients of the present invention, may be included in overages. Adding overages of these compounds may be necessary to meet the amounts claimed on the product label and product insert to ensure that those recited amounts are met throughout the shelf life of the product. Indeed, because of US regulatory requirements that label values reflect minimum contents of these nutrients, deviations in actual nutrient content from label values are usually thought to tend toward overages. Dwyer et al., ANAL BIOANAL CHEM. 389:37-46 (2007). In a specific embodiment, twelve carbon chain fatty acid or twelve carbon chain acylglycerols and one or more of the vitamins, minerals and nutrients may be included in the compositions and methods of the present invention in overages of the recited, specific label amounts of about 100% to about 150% of the label amount, although the overages are dependant on the stability of each ingredient. For example, overages of vitamin D and vitamin B12 may be necessary due to the lack of stability of specific forms. In another example, 5-methyltetrahydrofolate, a form of vitamin B9, is degraded by light, temperature and may degrade during processing and storage. Overages may be larger for some vitamins—particularly those that are less stable and more likely to deteriorate with a long shelf life, those that have other functions (such as antioxidants) in the product itself; for minerals, excess amounts with large overages are probably less likely because of their increased bulk and shelf life stability. Dwyer et al., ANAL BIOANAL CHEM, 389:37-46 (2007). Accordingly, when overages are included for any specific active ingredient, at some point in time, these ingredients with overages will degrade so that they fall within the amounts provided in the specific label. Thus, there is no literal difference between the amounts for active ingredients that include overages, and those amounts listed on the specific label. Furthermore, overages provide an equivalent efficacy of the active ingredient over the shelf life of the product. Accordingly, an active ingredient provided in overage amounts is an insubstantial change and performs substantially the same function, in substantially the same way, and leads to substantially the same result as that same active ingredient in the amounts as provided on the specific label.

In another embodiment, the nutritional supplements may include multiple vitamins, nutrients and minerals in one composition. Providing a single composition multivitamin and multinutrient supplement is an appealing feature because it improves patient compliance. Patients, and specifically for example, pregnant patients, often have nausua, and may have difficulties taking multiple pills. A one pill or one composition nutritional supplement that includes the beneficial vitamins, nutrients and minerals in appropriate dosage amounts would thus be beneficial for improving patient compliance in for example, pregnant women. In a specific embodiment one or more of the compositions may be in the dosage form of a gelcap.

In another specific embodiment, the compositions, kits and methods of the present invention may be in the form of a liquid gelcap which may consist of a filler comprising one or more pharmaceutically active materials dissolved or dispersed in an appropriate liquid vehicle encapsulated in a gelatin shell generally comprising gelatin together with a plasticizer such as glycerin or sorbitol. The filler material may comprise, for example, polyethylene glycols. See, for example, U.S. Pat. Nos. 4,780,316; 5,419,916; 5,641,512; and 6,589,536 which are expressly incorporated by reference herein.

A liquid gelcap has numerous advantages. First, it retains many of the advantages of consumer acceptance and is easier to swallow due to the outer coating being a soft and elastic gelatin shell. Also, liquid compositions are well suited for encapsulation within a soft gelatin shell, creating flexibility that further assists in the capsule being easier to swallow. The active drug contained in the liquid form also has advantages in dispersing the drug to the active site. For example, the active drug does not first have to dissolve in the gastrointestinal tract, thereby facilitating absorption of the pharmacologically active substance. See, for example, U.S. Pat. No. 6,689,382 which is expressly incorporated by reference herein. Other formulations take advantage of the liquid form by creating a sustained release gelatin capsule, thereby permitting the delivery of the drug in a controlled fashion. See, for example, U.S. Pat. Nos. 5,324,280 and 6,929,803, which are expressly incorporated by reference herein. Many shell and fill formulations are discussed in "Advances in Softgel Formulation Technology", M. S. Patel, F. S. S. Morton and H. Seager, Manufacturing Chemists, July 1989; "Soft Elastic Gelatin Capsules: A Unique Dosage Form", William R. Ebert, Pharmaceutical Technology, October 1977; and "Soft gelatin capsules: a solution to many tableting problems", H. Seager, Pharmaceutical Technology, September 1985.

In a specific embodiment, the present invention may comprise kits or compositions in the dosage form of a soft-gel gelcap. A soft-gel is a one-piece, sealed, soft gelatin shell that contains a solution, a suspension, or a semi-solid paste. Soft-gels are predominantly used to contain liquids wherein the active ingredients are present in the dissolved or suspended state. Soft-gels have been widely known and used for many years and for a variety of purposes. Because soft-gels have properties that are quite different from two-piece, hard shell capsules, the soft-gels are capable of retaining a liquid fill material. Soft-gels are often used to encapsulate consumable materials, including vitamins, dietary supplements, pharmaceuticals, and the like, in a liquid vehicle or carrier. Soft-gels arc a unique dosage form that can provide distinct advantages over more traditional dosage forms such as tablets, hard-shell capsules, and liquids. These advantages include patient compliance and consumer preference, improved bioavailability, speed of product development in many cases, shortened manufacturing time, enhanced drug stability due to less exposure of the active ingredient to oxygen, excellent dose uniformity, and product differentiation.

In another embodiment, the nutritional supplements may include multiple vitamins, nutrients and minerals in more than one composition. In a specific embodiment, various active ingredients may be incorporated into multiple compositions as a kit. In one example, fat soluble compounds such as omega 3 fatty acids, twelve carbon chain fatty acid or twelve carbon chain acylglycerols, may be included in one composition, whereas water soluble vitamins such as B-complex vitamins and vitamin C may be separated into another composition. In another example, the multiple compositions may be separated due to size or the large dosage amounts of specific ingredients. In another example, the nutritional supplementation of a multivitamin may not be adequate in one composition. Accordingly, all the active ingredients may be divided into a total of two compositions, three compositions, four compositions and five composition. In one embodiment, each composition may have equal amounts of each active ingredient. In another embodiment, compositions may have unequal amounts of various active ingredients, or merely supplemental amounts of specific active ingredients.

In another specific embodiment, the composition, kits and methods may be used as a dietary supplement. In another embodiment, the composition, kits and methods may be used as a prescription prenatal vitamin. In another embodiment, the compositions, kits and methods of the present invention, may be administered to a patient, such as a woman during pregnancy, prenatal or who is breast-feeding. In another embodiment, the compositions, kits and methods of the present invention may be utilized or administered, once a day, twice a day, three times a day, four times a day and five times a day. When multiple compositions are provided in a kit, the compositions may be co-administered at the same or administered separately.

The compositions, kits and methods of the present invention may be used or utilized in one or more dosage forms. In a specific embodiment, the dosage form more be a capsule, tablet, caplet, gel caplet (gelcap), syrup, a liquid composition, a concentrated powder, and a concentrated powder admixed with a liquid. The kits may comprise multiple compositions utilizing multiple dosage forms.

The ingredients of the present invention may thus be combined into a composition which may be in the form of capsule, tablet, caplet, gel caplet (gelcap), syrup, a liquid composition, a concentrated powder, and a concentrated powder admixed with a liquid, and which may be administered alone or in suitable combination with other components. For example, the composition of the present invention may be administered in one or more caplets or gel caps as practical for ease of administration. Each of the vitamins, nutrients and minerals is commercially available, and can be blended to form a single composition or can form multiple compositions, which may be co-administered. In a specific embodiment one or more of the compositions may be in the dosage form of a gelcap.

To prepare the compositions of the present invention, each of the active ingredients may be combined in intimate admixture with a suitable carrier according to conventional compounding techniques. The carrier may take a wide variety of forms depending upon the form of the preparation desired for administration, e.g., oral, sublingual, nasal, topical patch, or parenteral.

In preparing the composition in oral dosage form, any of the usual media may be utilized. For liquid preparations (e.g., suspensions, elixirs, and solutions), media containing, for example water, oils, alcohols, flavoring agents, preservatives, coloring agents and the like may be used. Pharmaceutical acceptable carriers such as starches, sugars, diluents, granulating agents, lubricants, binders, disintegrating agents and the like may be used to prepare oral solids (e.g., powders, caplets, pills, tablets, capsules, and lozenges). Controlled release forms may also be used. Because of their ease in administration, caplets, tablets, pills, and capsules represent the most advantageous oral dosage unit form, in which case solid carriers are employed. If desired, tablets may be sugar coated or enteric coated by standard techniques. All of these pharmaceutical carriers and formulations are well known to those of ordinary skill in the art. See, e.g., WADE & WALLER, HANDBOOK OF PHARMACEUTICAL EXCIPIENTS (2nd ed. 1994).

In a specific mode of administration, the dosage forms, may be swallowable, chewable or dissolvable.

Swallowable compositions are well known in the art and are those that do not readily dissolve when placed in the mouth and may be swallowed whole without any chewing or discomfort. In a specific embodiment of the present invention the swallowable compositions may have a shape containing no sharp edges and a smooth, uniform and substantially bubble free outer coating.

To prepare the swallowable compositions of the present invention, each of the active ingredients may be combined in intimate admixture with a suitable carrier according to conventional compounding techniques. In a specific embodiment of the swallowable compositions of the present invention, the surface of the compositions may be coated with a polymeric film. Such a film coating has several beneficial effects. First, it reduces the adhesion of the compositions to the inner surface of the mouth, thereby increasing the patient's ability to swallow the compositions. Second, the film may aid in masking the unpleasant taste of certain drugs. Third, the film coating may protect the compositions of the present invention from atmospheric degradation. Polymeric films that may be used in preparing the swallowable compositions of the present invention include vinyl polymers such as polyvinylpyrrolidone, polyvinyl alcohol and acetate, cellulosics such as methyl and ethyl cellulose, hydroxyethyl cellulose and hydroxylpropyl methylcellulose, acrylates and methacrylates, copolymers such as the vinyl-maleic acid and styrene-maleic acid types, and natural gums and resins such as zein, gelatin, shellac and acacia Pharmaceutical carriers and formulations for swallowable compounds are well known to those of ordinary skill in the art. See generally, e.g., WADE & WALLER, HANDBOOK OF PHARMACEUTICAL EXCIPIENTS (2nd ed. 1994).

Chewable compositions are those that have a palatable taste and mouthfeel, are relatively soft and quickly break into smaller pieces and begin to dissolve after chewing such that they are swallowed substantially as a solution.

In order to create chewable compositions, certain ingredients should be included to achieve the attributes just described. For example, chewable compositions should include ingredients that create pleasant flavor and mouthfeel and promote relative softness and dissolvability in the mouth. The following discussion describes ingredients that may help to achieve these characteristics.

Chewable compositions preferably have a pleasant or palatable flavor and a pleasant mouthfeel. A variety of ingredients can be included in the compositions of the present invention to enhance mouthfeel.

In the chewable compositions of the present invention, sugars such as white sugar, corn syrup, sorbitol (solution), maltitol (syrup), oligosaccharide, isomaltooligosaccharide, sucrose, fructose, lactose, glucose, lycasin, xylitol, lactitol, erythritol, mannitol, isomaltose, dextrose, polydextrose, dextrin, compressible cellulose, compressible honey, compressible molasses and mixtures thereof may be added to improve mouthfeel and palatability. Further, by way of example and without limitation, fondant or gums such as gelatin, agar, arabic gum, guar gum, and carrageenan may be added to improve the chewiness of the compositions. Fatty materials that may be included in the present invention include, by way of example and without limitation, vegetable oils (including palm oil, palm hydrogenated oil, corn germ hydrogenated oil, castor hydrogenated oil, cotton-seed oil, olive oil, peanut oil, palm olein oil, and palm stearin oil), animal oils (including refined oil and refined lard whose melting point ranges from 30° to 42° C.), Cacao fat, margarine, butter, and shortening.

Alkyl polysiloxanes (commercially available polymers sold in a variety of molecular weight ranges and with a variety of different substitution patterns) also may be used in the present invention to enhance the texture, the mouthfeel, or both of the chewable nutritional supplement compositions described herein. By "enhance the texture" it is meant that the alkyl polysiloxane improves one or more of the stiffness, the brittleness, and the chewiness of the chewable supplement, relative to the same preparation lacking the alkyl polysiloxane. By "enhance the mouthfeel" it is meant that the alkyl polysiloxane reduces the gritty texture of the supplement once it has liquefied in the mouth, relative to the same preparation lacking the alkyl polysiloxane.

Alkyl polysiloxanes generally comprise a silicon and oxygen-containing polymeric backbone with one or more alkyl groups pending from the silicon atoms of the back bone. Depending upon their grade, they can further comprise silica gel. Alkyl polysiloxanes are generally viscous oils. Exemplary alkyl polysiloxanes that can be used in the swallowable, chewable or dissolvable compositions of the present invention include, by way of example and without limitation, monoalkyl or dialkyl polysiloxanes, wherein the alkyl group is independently selected at each occurrence from a $C_1$-$C_6$-alkyl group optionally substituted with a phenyl group. A specific alkyl polysiloxane that may be used is dimethyl polysiloxane (generally referred to as simethicone). More specifically, a granular simethicone preparation designated simethicone GS may be used. Simethicone GS is a preparation which contains 30% simethicone USP. Simethicone USP contains not less than about 90.5% by weight $(CH_3)_3$—$Si\{OSi(CH_3)_2\}CH_3$ in admixture with about 4.0% to about 7.0% by weight $SiO_2$.

Chewable compositions should begin to break and dissolve in the mouth shortly after chewing begins such that the compositions can be swallowed substantially as a solution. The dissolution profile of chewable compositions may be enhanced by including rapidly water-soluble fillers and excipients. Rapidly water-soluble fillers and excipients preferably dissolve within about 60 seconds of being wetted with saliva. Indeed, it is contemplated that if enough water-soluble excipients are included in the compositions of the present invention, they may become dissolvable rather than chewable composition forms. Examples of rapidly water soluble fillers suitable for use with the present invention include, by way of example and without limitation, saccharides, amino acids and the like. Disintegrants also may be included in the compositions of the present invention in order to facilitate dissolution. Disentegrants, including permeabilising and wicking agents, are capable of drawing water or saliva up into the compositions which promotes dissolution from the inside as well as the outside of the compositions. Such disintegrants, permeabilising and/or wicking agents that may be used in the present invention include, by way of example and without limitation, starches, such as corn starch, potato starch, pregelatinized and modified starches thereof, cellulosic agents, such as Ac-di-sol, montrnorrilonite clays, cross-linked PVP, sweeteners, bentonite, microcrystalline cellulose, croscarmellose sodium, alginates, sodium starch glycolate, gums, such as agar, guar, locust bean, karaya, pectin, Arabic, xanthan and tragacanth, silica with a high affinity for aqueous solvents, such as colloidal silica, precipitated silica, maltodextrins, beta-cyclodextrins, polymers, such as carbopol, and cellulosic agents, such as hydroxymethylcellulose, hydroxypropylcellulose and hydroxyopropylmethylcellulose.

Finally, dissolution of the compositions may be facilitated by including relatively small particles sizes of the ingredients used.

In addition to those described above, any appropriate fillers and excipients may be utilized in preparing the swallowable, chewable and/or dissolvable compositions of the present invention so long as they are consistent with the objectives described herein. For example, binders, are substances used to cause adhesion of powder particles in granulations. Such compounds appropriate for use in the present invention include, by way of example and without limitation, acacia, compressible sugar, gelatin, sucrose and its derivatives, maltodextrin, cellulosic polymers, such as ethylcellulose, hydroxypropylcellulose, hydroxypropylmethyl cellulose, carboxymethylcellulose sodium and methylcellulose, acrylic polymers, such as insoluble acrylate ammoniomethacrylate copolymer, polyacrylate or polymethacrylic copolymer, povidones, copovidones, polyvinylalcohols, alginic acid, sodium alginate, starch, pregelatinized starch, guar gum, polyethylene glycol and others known to those of ordinary skill in the art.

Diluents also may be included in the compositions of the present invention in order to enhance the granulation of the compositions. Diluents can include, by way of example and without limitation, microcrystalline cellulose, sucrose, dicalcium phosphate, starches, lactose and polyols of less than 13 carbon atoms, such as mannitol, xylitol, sorbitol, maltitol and pharmaceutically acceptable amino acids, such as glycin, and their mixtures.

Lubricants are substances used in composition formulations that reduce friction during composition compression. Lubricants that may be used in the present invention include, by way of example and without limitation, stearic acid, calcium stearate, magnesium stearate, zinc stearate, talc, mineral and vegetable oils, benzoic acid, poly(ethylene glycol), glyceryl behenate, stearyl futmarate, and others known to those of ordinary skill in the art.

Glidants improve the flow of powder blends during manufacturing and minimize composition weight variation. Glidants that may be used in the present invention include, by way of example and without limitation, silicon dioxide, colloidal or fumed silica, magnesium stearate, calcium stearate, stearic acid, cornstarch, talc and others known to those of ordinary skill in the art.

Colorants also may be included in the nutritional supplement compositions of the present invention. As used herein, the term "colorant" includes compounds used to impart color to pharmaceutical preparations. Such compounds include, by way of example and without limitation, FD&C Red No. 3, FD&C Red No. 20, FD&C Yellow No. 6, FD&C Blue No. 2, D&C Green No. 5, FD&C Orange No. 5, D&C Red No. 8, caramel, and ferric oxide, red and others known to those of ordinary skill in the art Coloring agents also can include pigments, dyes, tints, titanium dioxide, natural coloring agents, such as grape skin extract, beet red powder, beta carotene, annato, carmine, turneric, paprika and others known to those of ordinary skill in the art. It is recognized that no colorant is required in the nutritional supplement compositions described herein.

If desired, the compositions of the present invention may be sugar coated or enteric coated by standard techniques. The unit dose forms may be individually wrapped, packaged as multiple units on paper strips or in vials of any size, without limitation. The swallowable, chewable or dissolvable compositions of the present invention may be packaged in unit dose, rolls, bulk bottles, blister packs and combinations thereof, without limitation.

The swallowable, chewable or dissolvable compositions of the present invention may be prepared using conventional methods and materials known in the pharmaceutical art. For example, U.S. Pat. Nos. 5,215,754 and 4,374,082 relate to methods for preparing swallowable compositions. U.S. Pat. No. 6,495,177 relates to methods to prepare chewable nutritional supplements with improved mouthfeel. U.S. Pat. No. 5,965,162, relates to kits and methods for preparing multi-vitamin comestible units which disintegrate quickly in the mouth, especially when chewed. Further, all pharmaceutical carriers and formulations described herein are well known to those of ordinary skill in the art, and determination of workable proportions in any particular instance will generally be within the capability of the person skilled in the art. Details concerning any of the excipients of the invention may be found in WADE & WALLER, HANDBOOK OF PHARMACEUTICAL EXCIPIENTS (2nd ed. 1994). AU active ingredients, fillers and excipients are commercially available from companies such as Aldrich Chemical Co., FMC Corp, Bayer, BASF, Alexi Fres, Witco, Mallinckrodt, Rhodia, ISP, and others.

A specific embodiment of the present invention may comprise kits or swallowable compositions packaged in blister packs. Blister packs as packaging for swallowable compositions are well known to those of ordinary skill in the art. Blister packs may be made of a transparent plastic sheet which as been formed to carry a matrix of depression or blisters. One or more swallowable compositions are received in each depression or blister. A foil or plastic backing is then adhered across the plane of the sheet sealing the swallowable compositions in their respective blisters. Examples of materials used for the blister packs include, but are not limited to, aluminum, paper, polyester, PVC, and polypropylene. Alternative materials are known to those of ordinary skill in the art. To remove a swallowable composition, the depression material is pressed in and the composition is pushed through the backing material. Multiple blister packs may be placed in an outer package, often a box or carton for sale and distribution.

Another specific embodiment of the present invention may comprise kits or swallowable compositions packaged in bottles. The bottle may be glass or plastic in form with a pop or screw top cap. Bottle packaging for compositions in swallowable form are well known to those of ordinary skill in the art.

Additionally, the unit dose forms may be individually wrapped, packaged as multiple units on paper strips or in vials of any size, without limitation. The swallowable, chewable or dissolvable compositions of the invention may be packaged in unit dose, rolls, bulk bottles, blister packs and combinations thereof, without limitation.

Other objectives, features and advantages of the present invention will become apparent from the following specific examples. The specific examples, while indicating specific embodiments of the invention, are provided by way of illustration only. Accordingly, the present invention also includes those various changes and modifications within the spirit and scope of the invention that may become apparent to those skilled in the art from this detailed description. The invention will be further illustrated by the following non-limiting examples.

Without further elaboration, it is believed that one skilled in the art, using the preceding description, can utilize the present invention to the fullest extent. The following examples are illustrative only, and not limiting of the remainder of the disclosure in any way whatsoever.

EXAMPLE 1

A composition of the following formulation was prepared in gel-cap form, including the appropriate excipients, by standard methods known to those of ordinary skill in the art:
- Vitamin A (Beta Carotene) . . . 1100 IU
- Vitamin C . . . 12 mg
- Vitamin D (Vitamin D3) . . . 1000 IU
- Vitamin E . . . 10 IU
- Vitamin B1 . . . 1.6 mg
- Vitamin B2 (Riboflavin) . . . 1.8 mg
- Vitamin B3 (Niacinamide) . . . 15 mg
- Vitamin B6 . . . 2.5 mg
- Vitamin B9 (Folic Acid) . . . 1 mg
- Vitamin B12 . . . 12 µg
- Iron . . . 27 mg
- Magnesium . . . 5 mg
- Zinc . . . 15 mg
- Copper 2.0 mg
- Iodine . . . 200 µg
- Lauric Acid . . . 60 mg
- DHA . . . 200 mg

EXAMPLE 2

In another example, various active ingredients may be incorporated into multiple compositions as a kit. In this non-limiting example, a first composition of the following formulation is prepared in caplet form, including the appropriate excipients, by standard methods known to those of ordinary skill in the art:
- Vitamin A (Beta Carotene) . . . 1100 IU
- Vitamin C . . . 12 mg
- Vitamin D (Vitamin D3) . . . 1000 IU
- Vitamin E . . . 10 IU
- Vitamin B1 . . . 1.6 mg
- Vitamin B2 (Riboflavin) . . . 1.8 mg
- Vitamin B3 (Niacinamide) . . . 15 mg
- Vitamin B6 . . . 2.5 mg
- Vitamin B9 (Folic Acid) . . . 1 mg
- Vitamin B12 . . . 12 µg
- Iron . . . 27 mg
- Magnesium . . . 5 mg
- Zinc . . . 15 mg
- Copper . . . 2.0 mg
- Iodine . . . 200 µg A second composition of the following formulation is prepared in gel-cap form by standard methods known to those of ordinary skill in the art:
- Lauric Acid . . . 60 mg
- DHA . . . 200 mg

EXAMPLE 3

In another example, various active ingredients may be divided into multiple compositions or a kit. In this non limiting example, the active ingredients of the composition of Example 1 may be divided into multiple compositions or kits. In this non limiting example, a first composition of the following formulation is prepared in gel-cap form, including the appropriate excipients, by standard methods known to those of ordinary skill in the art:
- Vitamin A (Beta Carotene) . . . 550 IU
- Vitamin C . . . 6.0 mg
- Vitamin D (Vitamin D3) . . . 500 IU
- Vitamin E . . . 5 IU
- Vitamin B1 . . . 0.8 mg
- Vitamin B2 (Riboflavin) . . . 0.9 mg
- Vitamin B3 (Niacinamide) . . . 7.5 mg
- Vitamin B6 . . . 1.25 mg
- Vitamin B9 (Folic Acid) . . . 0.5 mg
- Vitamin B12 . . . 6.0 µg
- Iron . . . 13.5 mg
- Magnesium . . . 2.5 mg
- Zinc . . . 7.5 mg
- Copper . . . 1.0 mg
- Iodine . . . 100 µg
- Lauric Acid . . . 30 mg
- DHA . . . 100 mg A second composition of the following formulation is prepared in gel-cap form by standard methods known to those of ordinary skill in the art:
- Vitamin A (Beta Carotene) . . . 550 IU
- Vitamin C . . . 6.0 mg
- Vitamin D (Vitamin D3) . . . 500 IU
- Vitamin E . . . 5 IU
- Vitamin B1 . . . 0.8 mg
- Vitamin B2 (Riboflavin) . . . 0.9 mg
- Vitamin B3 (Niacinamide) . . . 7.5 mg
- Vitamin B6 . . . 1.25 mg
- Vitamin B9 (Folic Acid) . . . 0.5 mg
- Vitamin B12 . . . 6.0 µg
- Iron . . . 13.5 mg
- Magnesium . . . 2.5 mg
- Zinc . . . 7.5 mg
- Copper . . . 1.0 mg
- Iodine . . . 100 µg
- Lauric Acid . . . 30 mg
- DHA . . . 100 mg

EXAMPLE 4

A study is undertaken to evaluate the effectiveness of the compositions of the present invention in the treatment of patients. The objective of the study is to determine whether oral intake of the compositions results in an improvement of the nutritional status of patients with regard to the specific vitamins and minerals contained in the administered compositions.

A double-blind, placebo controlled study is conducted over a six-month period. A total of 120 subjects (60 pregnant women entering the second trimester of pregnancy and 60 lactating women), aged 20-35 years, are chosen for the study. An initial assessment of the nutritional status of each woman is conducted. Vitamin A and vitamin B6 are measured using high performance liquid chromatography. Erythrocyte transketolase activity is used to measure vitamin B1 levels. Vitamin B2 levels are determined by assessment of erythrocyte glutathione reductase activity. Vitamin B3 levels are assessed by measuring urinary excretion of N' methylnicotinamide and its pyridone. Vitamin B9 is measured by radioimmunoassay (RIA), specifically The Solid Phase No Biol Folic Acid Kit (Diagnostic Products, Los Angeles, Calif.). Vitamin B12 is measured by RIA using human intrinsic factor as a binder. Vitamin C levels are measured by spectrophotometric and colorimetric methods. Vitamin D is measured using an extraction double-antibody RIA (Dia Sorin, Inc., Stillwater, Minn.). The peroxide hemolysis test is used to determine vitamin E status. Iron levels are measured using standard spectrophotometry. Iodine levels are measured by HPLC. Lauric acid levels and other fatty acids and acylglycerols are measured by reverse phase HPLC. Magnesium levels are measured by absorbance of a magnesium chelate with xylidl blue at 660 nM. Zinc levels are assessed using flame atomic absorption spectrometry (Perkins Elmer 460, Norwalk, Conn.). DHA is measured and quantified using gas chromatography procedures.

Additionally, total serum homocysteine levels are determined by extraction on the Multi-Prep® gravity series GVSA-100 column, a strong anion exchange gravity flow column, and measurement by gas chromatography/mass spectrometry. Biochemical Diagnostics, Austin, Tex.

The 120 subjects are separated into four separate groups of 30 women. In a first group comprising only pregnant women and in a second group comprising only lactating women, each subject is administered one dosage form of the composition as described in Example 1 once a day. In a third group comprising only pregnant women and in a fourth group comprising only lactating women, each subject is administered one placebo dosage form once a day. Thus, dosage form administration occurs every 24 hours. No other nutritional supplements are taken by the subjects during the assessment period.

An assessment of the nutritional status of each woman is conducted utilizing the methods described above at one month intervals for a six month period. The data is evaluated using multiple linear regression analysis and a standard t-test. In each analysis, the baseline value of the outcome variable is included in the model as a covariant. Treatment by covariant interaction effects is tested by the method outlined by Weigel & Narvaez, 12 CONTROLLED CLINICAL TRIALS 378-94 (1991). If there are no significant interaction effects, the interaction terms are removed from the model. The regression model assumptions of normality and homogeneity of variance of residuals are evaluated by inspection of the plots of residuals versus predicted values. Detection of the temporal onset of effects is done sequentially by testing for the presence of significant treatment effects at 1, 2, 3, 4, 5, and 6 months, proceeding to the earlier time in sequence only when significant effects have been identified at each later time period. Changes from the baseline within each group are evaluated using paired t-tests. In addition, analysis of variance is performed on all baseline measurements and measurable subject characteristics to assess homogeneity between groups. All statistical procedures are conducted using the Statistical Analysis System (SAS Institute Inc., Cary, N.C.). An alpha level of 0.05 is used in all statistical tests.

An unexpected statistically significant improvement in the nutritional status of vitamin, mineral, and nutrient levels measured is observed in the treated subjects over the controls upon completion of the study. Specifically, homocysteine levels in women receiving supplements remain unelevated. Therefore, the study confirms that oral administration of the compositions of the present invention is effective in improving the nutritional status of patients. Other unexpected results relate to the observation that the length of gestation is increased by approximately six days in women receiving supplements, due to DHA intake, and their homocysteine levels are not elevated, due to folic acid intake, leading to a better prognosis regarding risk of neural tube defects in their infants.

EXAMPLE 5

A study is undertaken testing supplementation of iodine, vitamin D and the fatty acid lauric acid. A study is conducted over a three-month period. A total of 120 subjects (pregnant women entering the second trimester of, aged 20-35 years, are chosen for the study) An initial assessment of the nutritional status of each woman for iodine, vitamin D and lauric acid is conducted as provided in Example 4.

In the first group, each subject is administered 1 gelcap daily, with the composition as described in Example 1. In the second group, each subject is administered 1 one caplet daily that includes the following ingredients in the listed amounts (control):

| Ingredient | Amount |
| --- | --- |
| Vitamin A (acetate) | 1100 IU |
| Beta Carotene | 600 IU |
| Vitamin $B_1$ (thiamine mononitrate) | 1.6 mg |
| Vitamin $B_2$ (riboflavin) | 1.8 mg |
| Vitamin $B_3$ (niacinamide) | 15 mg |
| Vitamin $B_6$ (pyridoxine hydrochloride) | 2.5 mg |
| Vitamin $B_9$ (folic acid) | 1000 µg |
| Vitamin $B_{12}$ (cyanocobalamin) | 5 µg |
| Vitamin C (ascorbic acid) | 60 mg |
| Vitamin D (cholecalciferol) | 400 IU |
| Vitamin E (d-alpha-tocopheryl acetate) | 30 IU |
| Iron (polysaccharide complex) | 29 mg |
| Magnesium (magnesium oxide) | 25 mg |
| Zinc (zinc oxide) | 15 mg |

An assessment of nutritional status for each subject is measured at one-month intervals for a six month period. Specifically, in regard to vitamin D deficiency, the serum levels of 25-hydroxyvitamin D are measured to assess if they meet levels as high as 30 ng/ml or are increasing towards a level of 30 ng/ml. The data is evaluated using multiple linear regression analysis and a standard students t-test. In each analysis the baseline value of the outcome variable is included in the model as a covariant. Treatment by covariant interaction effects is tested by the method outlined by Weigel & Narvaez, 12 CONTROLLED CLINICAL TRIALS 378-94 (1991). If there are no significant interaction effects, the interaction terms are removed from the model. The regression model assumptions of normality and homogeneity of variance of residuals are evaluated by inspection of the plots of residuals versus predicted values. Detection of the temporal onset of effects is done sequentially by testing for the presence of significant treatment effects at 16, 12, and 8 weeks, proceeding to the earlier time in sequence only when significant effects have been identified at each later time period. Changes from the baseline within each group are evaluated using paired t-tests. In addition, analysis of variance is performed on all baseline measurements and measurable subject characteristics to assess homogeneity between groups. All statistical procedures are conducted using the Statistical Analysis System (SAS Institute Inc., Cary, N.C.). An alpha level of 0.05 is used in all statistical tests.

A statistically significant improvement in the nutritional status is preferably observed in the treated subjects who were administered the composition of Example 1 over treated subjects who are administered the controls. Specifically, in regard to vitamin D supplementation, the tested serum levels of 25-hydroxyvitamin D are preferably in the range of 30 ng/ml for treated subjects. Specifically, in regard to lauric acid supplementation, the milk content of subjects shows an increased milk content of lauric acid over time in terms of percentage of overall fatty acid content; whereas the control shows no increased lauric acid content. Specifically, in regard to iodine content, serum levels show an increased level of iodide levels; whereas the control shows not increased iodide serum level.

While specific embodiments of the present invention have been described, other and further modifications and changes may be made without departing from the spirit of the invention. All further and other modifications and changes are included that come within the scope of the invention as set forth in the claims. The disclosure of each publication cited above is expressly incorporated by reference in its entirety to the same extent as if each were incorporated by reference individually.

EXAMPLE 6

A study is undertaken testing the fatty acid composition in women's milk after nutritional supplementation with fatty acids including lauric acid. Fifty women will partake in the study. Lactating women aged 19-43 y participate in the study during the first 6 months of lactation. The women remain in the study for about 10 weeks including a 2-wk washout period between consumption of the test fatty acids. The diets of the subjects remain constant during the study. The Diet Habit Survey indicates that there is no significant differences in cholesterol-saturated fat, carbohydrate, fish, or total scores. Subjects consume the coconut oil composition once in 2-wk intervals. A 40 g coconut oil composition is consumed in the morning by each patient in place of breakfast. Subjects collect milk samples once in the morning before consuming the test formula; once at each of the following time points after consuming the formula: 6, 10, 14, and 24 h; and once daily for 4-7 days. The results of this study show an acute response, especially within the first 24 hr. Ingestion of the formula containing 40 g coconut oil increases the milk content of lauric acid over time ($P<0.001$). Lauric acid is increased from 3.9% of fatty acids at baseline to 9.2% at 10 h and 9.6% at 14 hr. See Francois et al., AM J CLIN NUTR, 67(2): 301-8 (1998).

EXAMPLE 7

Fourteen lactating women drink two test formulas, each containing a different fat: menhaden oil, and coconut oil. The subjects collect a midfeeding milk sample before consuming the breakfast test formula and additional samples at 6, 10, 14, and 24 h and then once daily for 4-7 d. Fatty acids of special interest included eicosapentaenoic and docosahexaenoic acids from menhaden oil, and lauric acid from coconut oil. Each of these fatty acids increases significantly in human milk within 6 hrs of consumption of the test formulas ($P<0.001$). Maximum increases occur 14 hrs after coconut oil (lauric acid), and menhaden oil (eicosapentaenoic acid); and 24 hrs after menhaden oil (docosahexaenoic acid). Surprisingly, lauric acid remains significantly elevated in milk ($P<0.05$) for only about 10-24 hrs, whereas docosahexaenoic acid and eicosapentaenoic acid remain significantly elevated in milk for 2 days and three days respectively. These data support the hypothesis that there is a rapid transfer of dietary fatty acids from chylomicrons into human milk. These data also surprisingly support that lauric acid significantly increases in milk for only up to about 24 hr. Accordingly, a daily source or daily supplementation of lauric acid for a lactating patient to retain a high level of lauric acid in human milk is suggested.

What is claimed is:

1. A composition consisting vitamin D in an amount of about 1000 I.U., lauric acid in an amount of about 60 mg, iodine in an amount of about 200 µg, vitamin B1 in an amount of about 1.6 mg, vitamin B6 in an amount of about 2.5 mg, vitamin B12 in an amount of about 12 µg, vitamin B2 in an amount of about 1.8 mg, vitamin B9 in an amount of about 1.0 mg, vitamin E in an amount of about 10 I.U., vitamin A in an amount of about 1100 I.U., vitamin C in an amount of about 12 mg, vitamin B3 in an amount of about 15 mg, iron in an amount of about 27 mg, zinc in an amount of about 15 mg, copper in an amount of about 2.0 mg, magnesium in an amount of about 5 mg, and docosahexaenoic acid (DHA) in an amount of about 200 mg, and one or more pharmaceutically acceptable carriers.

2. The composition of claim 1, wherein the source of said lauric acid is from one or more of the group consisting of algae oil, Martek Algae oil, coconut oil, babassu oil, and palm kernel oil.

3. The composition of claim 1, wherein said lauric acid is derived from a natural or synthetic source or is genetically engineered.

4. The composition of claim 1, wherein said composition is provided in the dosage form of a gelcap.

5. The composition of claim 1, wherein said composition is a dietary supplement or a prescription prenatal vitamin.

* * * * *

UNITED STATES PATENT AND TRADEMARK OFFICE
CERTIFICATE OF CORRECTION

PATENT NO.         : 8,168,611 B1
APPLICATION NO.    : 13/248428
DATED              : May 1, 2012
INVENTOR(S)        : Philippe Perrin, Guillaume Herry and Cecile Boyer-Joubert Page 1 of 1

It is certified that error appears in the above-identified patent and that said Letters Patent is hereby corrected as shown below:

In the Claims:

Column 52, Claim 1, Line 32 insert after consisting --of--.

Signed and Sealed this
Eighteenth Day of June, 2013

Teresa Stanek Rea
*Acting Director of the United States Patent and Trademark Office*